US009045727B2

(12) United States Patent
Compans et al.

(10) Patent No.: US 9,045,727 B2
(45) Date of Patent: Jun. 2, 2015

(54) VIRUS-LIKE PARTICLES, METHODS OF PREPARATION, AND IMMUNOGENIC COMPOSITIONS

(75) Inventors: Richard L. Compans, Atlanta, GA (US); Chinglai Yang, Decatur, GA (US); Qizhi Yao, Houston, TX (US); Sang-moo Kang, Norcross, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 1328 days.

(21) Appl. No.: 11/397,830

(22) Filed: Apr. 4, 2006

(65) Prior Publication Data

US 2006/0216702 A1 Sep. 28, 2006

Related U.S. Application Data

(63) Continuation-in-part of application No. 10/514,462, filed as application No. PCT/US03/15930 on May 19, 2003, now abandoned.

(60) Provisional application No. 60/381,557, filed on May 17, 2002, provisional application No. 60/454,115, filed on Mar. 11, 2003, provisional application No. 60/454,139, filed on Mar. 11, 2003, provisional application No. 60/454,584, filed on Mar. 14, 2003, provisional application No. 60/468,318, filed on May 6, 2003, provisional application No. 60/471,246, filed on May 16, 2003.

(51) Int. Cl.
*A61K 39/12* (2006.01)
*C12Q 1/70* (2006.01)
*C12N 7/00* (2006.01)
*A61K 39/21* (2006.01)
*C07K 14/005* (2006.01)
*A61K 39/00* (2006.01)

(52) U.S. Cl.
CPC . *C12N 7/00* (2013.01); *A61K 39/12* (2013.01); *A61K 39/21* (2013.01); *A61K 2039/5258* (2013.01); *C07K 14/005* (2013.01); *C07K 2319/01* (2013.01); *C12N 2740/15022* (2013.01); *C12N 2740/16023* (2013.01); *C12N 2740/16222* (2013.01); *C12N 2760/12022* (2013.01)

(58) Field of Classification Search
CPC .................................. C07K 14/005; C12N 7/00
See application file for complete search history.

(56) References Cited

U.S. PATENT DOCUMENTS

| 4,009,258 | A | 2/1977 | Kilbourne |
|---|---|---|---|
| 4,666,829 | A | 5/1987 | Glenner et al. |
| 5,298,244 | A | 3/1994 | Redmond et al. |
| 5,580,773 | A | 12/1996 | Kang et al. |
| 5,618,536 | A | 4/1997 | Lowy |
| 5,714,374 | A | 2/1998 | Arnold |
| 5,830,877 | A | 11/1998 | Carson et al. |
| 5,843,451 | A | 12/1998 | Compans et al. |
| 6,001,634 | A | 12/1999 | Palese et al. |
| 6,077,662 | A * | 6/2000 | Compans et al. ................. 435/5 |
| 6,099,847 | A * | 8/2000 | Tobin et al. ............... 424/208.1 |
| 6,153,201 | A | 11/2000 | Rose et al. |
| 6,171,591 | B1 | 1/2001 | Hall |
| 6,207,646 | B1 | 3/2001 | Krieg et al. |
| 6,420,160 | B1 | 7/2002 | Bloch |
| 6,572,863 | B1 | 6/2003 | Rovinski et al. |
| 6,599,508 | B1 | 7/2003 | Gissmann et al. |
| 6,602,705 | B1 | 8/2003 | Barnett et al. |
| 6,710,173 | B1 | 3/2004 | Binley et al. |
| 6,719,978 | B2 | 4/2004 | Schiller et al. |
| 6,740,323 | B1 | 5/2004 | Selby et al. |
| 6,783,939 | B2 | 8/2004 | Olmstead et al. |
| 7,556,940 | B2 | 7/2009 | Galarza et al. |
| 7,579,007 | B2 * | 8/2009 | Mosca ....................... 424/204.1 |
| 7,682,618 | B2 * | 3/2010 | Bavari et al. ............... 424/204.1 |
| 7,795,017 | B2 | 9/2010 | Robinson |
| 2001/0016199 | A1 | 8/2001 | Johnston |
| 2002/0106798 | A1* | 8/2002 | Robinson et al. ............. 435/456 |
| 2003/0044429 | A1* | 3/2003 | Aderem et al. ............ 424/234.1 |
| 2005/0186621 | A1 | 8/2005 | Galarza |
| 2006/0088909 | A1 | 4/2006 | Compans |
| 2006/0216702 | A1 | 9/2006 | Compans |
| 2010/0047266 | A1 | 2/2010 | Haynes |
| 2010/0196419 | A1 | 8/2010 | Compans |
| 2012/0052082 | A1 | 3/2012 | Compans |

FOREIGN PATENT DOCUMENTS

| WO | 9850071 | 12/1998 |
|---|---|---|
| WO | 0032229 | 8/2000 |
| WO | 02087614 | 7/2002 |

OTHER PUBLICATIONS

Machuca et al. Intervirology 1999, vol. 42, p. 37-42.*
Doan et al. Reviews in Medical Virology, 2005, vol. 15, p. 75-88.*
AIDS Research and Human Retroviruses, 2000, vol. 16, p. 227-236 in IDS of Aug. 9, 2007.*
Pushko Journal of Virology, 2001, vol. 75, p. 11677-11685 in IDS of Jun. 7, 2007.*
Deml et al. Virology, 1997, vol. 235, p. 10-25.*
Zhou et al. (Virology, 1998, vol. 246, p. 83-94).*
Latham et al. (Journal of Virology, Jul. 2001, p. 6154-6165).*
Salmons et al., Construction of Retrovial Vectors for Targeted Delivery and Expression of Therapeutic Genes. Leukemia. 1995, vol. 9, Suppl. 1, pp. S53-S60.

(Continued)

*Primary Examiner* — Agnieszka Boesen
(74) *Attorney, Agent, or Firm* — Emory Patent Group

(57) ABSTRACT

Briefly described, virus-like particles, methods of preparing virus-like particles, immunogenic compositions that include virus-like particles, and methods of eliciting an immune response using immunogenic compositions that include virus-like particles are described herein. A virus-like particle (VLP) can include a viral core protein that can self assemble into the VLP core and at least one viral surface envelope glycoprotein expressed on the surface of the VLP. The VLP can also optionally include at least one adjuvant molecule expressed on the surface of the VLP.

13 Claims, 19 Drawing Sheets

(56) References Cited

OTHER PUBLICATIONS

Pushko et al. Individual and Bivalent Vaccines Based on Alphavirus Replicons Protect Guinea Pigs Against Infection With Lassa and Ebola viruses. Journal of virology. Dec. 2001, vol. 75, No. 23, pp. 11677-11685.

Kang et al. Mucosal immunization with virus-like particles of simian immunodeficiency virus conjugated with cholera toxin subunit B. journal of Virology. Sep. 2003, vol. 77, No. 18, pp. 9823-9830.

Schmitt et al. Requirements for budding of paramyxovirus simian virus 5 virus-like particles. Journal of Virology. Apr. 2002, vol. 76, No. 8, pp. 3952-3964.

Noda et al. Ebola virus VP40 drives the formation of virus-like filamentous particles along with GP. Journal of Virology. May 2002, vol. 76, No. 10, pp. 4855-4865.

Rabu et al. Chimeric Newcastle disease virus nucleocapsid with parts of viral hemagglutinin-neuraminidase and fusion proteins. Acta Virology. 2002, vol. 46, No. 4, pp. 211217.

Godeke et al. Assembly of spikes into coronavirus particles is mediated by the carboxy-terminal domain of the spike protein. Journal of Virology. 2000, vol. 74, No. 3, pp. 1566-1571.

Guo, et al., Enhancement of mucosal immune responses by chimeric influenza HA/SHIV virus-like particles; Science Direct; Virology; 313; 2003; pp. 502-513.

Yao, et al., Virus-like particle and DNA-based candidate AIDS vaccines; Vaccine; vol. 21; 2003; pp. 638-643.

Kang, et al., Enhancement of Mucosal Immunization with Virus-Like Particles of Simian Immunodefiency Virus; Journal of Virology; vol. 77, No. 6; Mar. 2003; pp. 3615-3623.

Akira, et al., Toll-Like Receptor Signalling, Nature Reviews/Immunology, vol. 4, Jul. 2004, pp. 499-511.

Deml, et al., Increased Incorporation of Chimeric Human Immunodeficiency Virus type 1 gp 120 Proteins into Pr55gag Virus-like Particles by an Epstein-Barr Virus gp220/350-Derived Transmembrane Domain, Virology 235, 10-25 (1997) Article No. VY978669, pp. 10-25.

Latham, Formation of Wild-Type and Chimeric Influenza Virus-Like Particles following Simultaneous Expression of Only Four Structural Proteins, Journal of Virology, vol. 75, No. 13, Jul. 2001, pp. 6154-6165.

Kang, et al., Development of HIV/AIDS Vaccine Using Chimeric gag-env Virus-Like Particles, Biol. Chem., vol. 380, pp. 353-364, Mar. 1999.

EPO Supplemental Search Report, dated Jul. 9, 2007.

Yao, Qizhi, et al. "Production and characterization of simian-human immunodeficiency virus-like particles" Aids Research and Human Retroviruses, vol. 16, No. 3, Feb. 10, 2000, pp. 227-236.

Latham, et al., "Formation of wild-type and chimeric influenza virus-like paricles following simultaneous expression of only four structural proteins," Journal of Virology, The American Society for Microbiology, US., vol. 75, No. 13, Jul. 2001, pp. 6154-6165.

McGettigan, James, et al., "Rabies virus-based vectors expressing human immunodifiency virus type 1 (HIV-1) envelope protein induce a strong, cross-reactive cytotoxic T-lymphocyte response against envelope proteims from different HIV-1 isolates," Journal of Virology, vol. 75, No. 9, May 2001, pp. 4430-4434.

Schnell, Matthias J., et al. "Recombinant rabies virus as potential live-viral vaccines for HIV-1" Proceedings of the National Academy of Sciences of the United States of America, vol. 97, No. 7, Mar. 28, 2000, pp. 3544-3549.

Yamshchikov, G.V. et al. "Assembly of SIV Virus-like particles containing envelope proteins using a baculovirus pxpression system," Virology, Academic Press, Orlando, US, vol. 214, No. 1 Dec. 1995, pp. 50-58.

Guo, L., et al., "Enhancement of Mucosal immune response by chimeric influenza HA/SHIV virus-like particles" Virology, Academic Press, Orlando, US, vol. 313, No. 2, Sep. 1, 2003, pp. 502-513.

McGettigan James, P., et al., "Expression and immunogenicity of human immunodeficiency virus type 1 Gag expressed by a replication-competent rhabdovirus-based vaccine vector", Journal of Virology, vol. 75, No. 18, Sep. 2001, pp. 8724-8732.

Garnier, Laurence, et al., Incorporation of pseudorabies virus gD into human immunodeficiency virus type 1 Gag particles produced in baculovirus-infected cells; Journal of Virology, vol. 69, No. 7,m 1995, pp. 4060-4068.

Neumann, Gabriele, et al., "Plasmid-Driven Formation of influenza Virus-Like Particles", Journal of Virology, Jan. 2000, vol. 74, No. 1, pp. 547-551.

Wang et al., J Virol., 2008, 82(23):11813-23 entitled "Incorporation of membrane-anchored flagellin into influenza virus-like particles enhances the breadth of immune responses".

Skountzou et al., J Virol., 2007, 81(3):1083-94, entitled "Incorporation of glycosylphosphatidylinositol-anchored granulocyte-macrophage colony-stimulating factor or CD40 ligand enhances immunogenicity of chimeric simian immunodeficiency virus-like particles".

Poloso et al., Molecular Immunology, 2001, 38:803-816 entitled GPI-anchoring of GM-CSF results in active membrane.

Kim et al., "Virus-like Particles Containing Multiple M2 Extracellular Domains" Molecular Therapy vol. 21 No. 2, 485-492 2013.

Kim et al.,(2) "Multiple heterologous M2 extracellular domains presented on virus-like particles confer broader and stronger M2 immunity than live influenza A virus infection" Antiviral Research, 99(3), 2013, pp. 328-335.

Wang et al., "Nanoclusters self-assembled from conformation-stabilized influenza M2e as broadly cross-protective influenza vaccines" Nanomedicine. 2013.

Wang et al.,(2) "Virus-Like Particles Containing the Tetrameric Ectodomain of Influenza Matrix Protein 2 and Flagellin Induce Heterosubtypic Protection in Mice" BioMed Research International vol. 2013, Article ID 686549.

Wang et al. "Enhanced Influenza Virus-Like Particle Vaccines Containing the Extracellular Domain of Matrix Protein 2 and a Toll-Like Receptor Ligand" Clin Vaccine Immunol, 2012, 19(8):1119-25.

Song et al., "Influenza virus-like particles containing M2 induce broadly cross protective immunity." PLoS One. 2011, 6 (1):e14538.

Wang et al., "Intranasal immunization with influenza VLPs incorporating membrane-anchored flagellin induces strong heterosubtypic protection." PLoS One. 2010, 5(11):e13972.

Quan et al., "Virus-like particle vaccine induces protective immunity against homologous and heterologous strains of influenza virus." J Virol. 2007, 81(7):3514-24.

Galarza et al., Virus-like particle vaccine conferred complete protection against a lethal influenza virus challenge. Viral Immunol. 2005, 18(2):365-72.

Hanko, et al., "Flagellin is an Effective Adjuvant for Immunization Against Lethal Respiratory Challenge with Yersinia Pestis," Infection and Immunity, 2006, 74(2):1113-110.

Koutski et al., "A Controlled Trial of a Human Papillomavirus Type 16 Vaccine" N Engl J Med 2002, 347:1645-1651.

Leclerc et al., Proteasome-Independent Major Histocompatibility Complex Class I Cross-Presentation Mediated by Papaya Mosaic Virus-Like Particles Leads to Expansion of Specific Human T Cells, J Virol, 2007, 81(3):1319-1326.

Revaz et al. "Humoral and cellular immune responses to airway immunization of mice with human papillomavirus type 16 virus-like particles and mucosal adjuvants" Antivir. Res., 2007, 76 (1):75-85.

Skountzou et al., "Incorporation of Glycosylphosphatidylinositol-Anchored Granulocyte-Macrophage Colony-Stimulating Factor or CD40 Ligand Enhances Immunogenicity of Chimeric Simian Immunodeficiency Virus-Like Particles" J. Virol. 2007, 81(3):1083-1094.

Brightet al., Influenza virus-like particles elicit broader immune responses than whole virion inactivated influenza virus or recombinant hemagglutinin Vaccine, 2007, 25:3871-3878.

Matassov et al. "A novel intranasal virus-like particle (VLP) vaccine designed to protect against the pandemic 1918 influenza A virus (H1N1)" Viral Immunol. 2007, 20(3):441-52.

Puchko et al., Influenza virus-like particles comprised of the HA, NA, and M1 proteins of H9N2 influenza virus induce protective immune responses in BALB/c mice. Vaccine, 2005, 23:5751-5759.

Kang et al., Influenza vaccines based on virus-like particles Virus Res. 2009,143(2):140-6.

(56) References Cited

OTHER PUBLICATIONS

Ogushi et al., "*Salmonella enteritidis* FliC (flagella filament protein) induces human beta-defensin-2 mRNA production by Caco-2 cells." J Biol Chem. 2001, 276(32):30521-6.

Zhou et al., "Membrane-anchored incorporation of a foreign protein in recombinant influenza virions" Virology. 1998, 246(1):83-94.

Gomez et al. "Influenza virus matrix protein is the major driving force in virus budding" Virol. 2000, 74(24):11538-47.

Latham "Formation of wild-type and chimeric influenza virus-like particles following simultaneous expression of only four structural proteins" Virol. 2001, 75(13):6154-65.

Yao et al., Production and characterization of simian—human immunodeficiency virus-like particles. AIDS Res Hum Retroviruses. 2000, 16(3):227-36.

Salmons et al. Construction of retroviral vectors for targeted delivery and expression of therapeutic genes. Leukemia. 1995, vol. 9, suppl. 1, pp. S53-S60.

McGettigan et al., Rabies Virus-Based Vectors Expressing Human Immunodeficiency Virus Type 1 (HIV-1) Envelope Protein Induce a Strong, Cross-Reactive Cytotoxic T-Lymphocyte Response against Envelope Proteins from Different HIV-1 Isolates J. Virol. 2001 vol. 75 No. 9 4430-4434.

Schnell et al., Recombinant rabies virus as potential live-viral vaccines for HIV-1.Proc Natl Acad Sci U S A. 2000,28;97(7):3544-9.

Yamshchikov et al., Assembly of SIV virus-like particles containing envelope proteins using a baculovirus expression system. Virology. 1995 ,214(1):50-8.

Guo et al., Enhancement of mucosal immune responses by chimeric influenza HA/SHIV virus-like particles. Virology. 2003, 313(2):502-13.

McGettigan et al.,Expression and Immunogenicity of Human Immunodeficiency Virus Type 1 Gag Expressed by a Replication-Competent Rhabdovirus-Based Vaccine VectorJ. Virol. 2001 vol. 75 No. 18 8724-8732.

Garnier et al., Incorporation of pseudorabies virus gD into human immunodeficiency virus type 1 Gag particles produced in baculovirus-infected cells. J Virol. 1995, 69(7):4060-8.

Pushko et al. Individual and bivalent vaccines based on alphavirus replicons protect guinea pigs against infection with Lassa and Ebola viruses. J Virol. 2001, 75(23):11677-85.

McGuigan et al. Recombinant-expressed virus-like particle pseudotypes as an approach to vaccine development. Vaccine. 1993; vol. 11, No. 6, pp. 675-678.

Kang et al. Mucosal immunization with virus-like particles of simian immunodeficiency virus conjugated with cholera toxin subunit B. J Virol. 2003, vol. 77, No. 18, pp. 9823-9830.

Schmitt et al. Requirements for budding of paramyxovirus simian virus 5 virus-like particles. Journal of Virology. 2002, vol. 76, No. 8, pp. 3952-3964.

Noda et al. Ebola virus VP40 drives the formation of virus-like filamentous particles along with GP. J Virol. 2002, vol. 76, No. 10, pp. 4855-4865.

Rabu et al. Chimeric Newcastle disease virus nucleocapsid with parts of viral hemagglutinin-neuraminidase and fusion proteins. Acta Virology. 2002, vol. 46, No. 4, pp. 211-217.

McInerney et al. Analysis of the ability of five adjuvants to enhance immune responses to a chimeric plant virus displaying an HIV-1 peptide. Vaccine. 1999, vol. 17, No. 11-12, pp. 1359-1368.

Godeke et al. Assembly of spikes into corona virus particles is mediated by the carboxyterminal domain of the spike protein. Journal of Virology. 2000, vol. 74, No. 3, pp. 1566-1571.

\* cited by examiner

| Label | Extracellular domain | TM | C-tail |
|---|---|---|---|
| HIV Env | HIV | HIV | |
| HIV Env-T(MMTV) | HIV | MMTV | |
| HIV Env-TC(MMTV) | HIV | MMTV | MMTV |
| HIV Env-T(Gp64) | HIV | Gp64 | |
| HIV Env-TC(Gp64) | HIV | Gp64 | Gp64 |
| HIV Env-T(LFV) | HIV | LFV | |
| HIV Env-TC (LFV) | HIV | LFV | LFV |
| HIV Env-T(HA) | HIV | HA | |
| HIV Env-TC(HA) | HIV | HA | HA |

SEQUENCE LISTING

```
<160> NUMBER OF SEQ ID NOS: 11

<210> SEQ ID NO 1
<211> LENGTH: 847
<212> TYPE: PRT
<213> ORGANISM: HIV SF162 Envelope Protein

<400> SEQUENCE: 1

Met Arg Val Lys Gly Ile Arg Lys Asn Tyr Gln His Leu Trp Arg Gly
1               5                   10                  15
```

```
Gly Thr Leu Leu Leu Gly Met Leu Met Ile Cys Ser Ala Val Glu Lys
             20                  25                  30

Leu Trp Val Thr Val Tyr Tyr Gly Val Pro Val Trp Lys Glu Ala Thr
         35                  40                  45

Thr Thr Leu Phe Cys Ala Ser Asp Ala Lys Ala Tyr Asp Thr Glu Val
 50                  55                  60

His Asn Val Trp Ala Thr His Ala Cys Val Pro Thr Asp Pro Asn Pro
 65                  70                  75                  80

Gln Glu Ile Val Leu Glu Asn Val Thr Glu Asn Phe Asn Met Trp Lys
                 85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

His Cys Thr Asn Leu Lys Asn Ala Thr Asn Thr Lys Ser Ser Asn Trp
130                 135                 140

Lys Glu Met Asp Arg Gly Glu Ile Lys Asn Cys Ser Phe Lys Val Thr
145                 150                 155                 160

Thr Ser Ile Arg Asn Lys Met Gln Lys Glu Tyr Ala Leu Phe Tyr Lys
                165                 170                 175

Leu Asp Val Val Pro Ile Asp Asn Asp Asn Thr Ser Tyr Lys Leu Ile
            180                 185                 190

Asn Cys Asn Thr Ser Val Ile Thr Gln Ala Cys Pro Lys Val Ser Phe
        195                 200                 205

Glu Pro Ile Pro Ile His Tyr Cys Ala Pro Ala Gly Phe Ala Ile Leu
210                 215                 220

Lys Cys Asn Asp Lys Lys Phe Asn Gly Ser Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Gly Val Val Ile Arg Ser
            260                 265                 270

Glu Asn Phe Thr Asp Asn Ala Lys Thr Ile Ile Val Gln Leu Lys Glu
        275                 280                 285

Ser Val Glu Ile Asn Cys Thr Arg Pro Asn Asn Asn Thr Arg Lys Ser
290                 295                 300

Ile Thr Ile Gly Pro Gly Arg Ala Phe Tyr Ala Thr Gly Asp Ile Ile
305                 310                 315                 320

Gly Asp Ile Arg Gln Ala His Cys Asn Ile Ser Gly Glu Lys Trp Asn
                325                 330                 335

Asn Thr Leu Lys Gln Ile Val Thr Lys Leu Gln Ala Gln Phe Gly Asn
            340                 345                 350

Lys Thr Ile Val Phe Lys Gln Ser Ser Gly Gly Asp Pro Glu Ile Val
        355                 360                 365

Met His Ser Phe Asn Cys Gly Gly Glu Phe Phe Tyr Cys Asn Ser Thr
370                 375                 380

Gln Leu Phe Asn Ser Thr Trp Asn Asn Thr Ile Gly Pro Asn Asn Thr
385                 390                 395                 400

Asn Gly Thr Ile Thr Leu Pro Cys Arg Ile Lys Gln Ile Ile Asn Arg
                405                 410                 415

Trp Gln Glu Val Gly Lys Ala Met Tyr Ala Pro Pro Ile Arg Gly Gln
            420                 425                 430
```

-continued

```
Ile Arg Cys Ser Ser Asn Ile Thr Gly Leu Leu Thr Arg Asp Gly
            435                 440                 445
Gly Lys Glu Ile Ser Asn Thr Thr Glu Ile Phe Arg Pro Gly Gly Gly
450                 455                 460
Asp Met Arg Asp Asn Trp Arg Ser Glu Leu Tyr Lys Tyr Lys Val Val
465                 470                 475                 480
Lys Ile Glu Pro Leu Gly Val Ala Pro Thr Lys Ala Lys Arg Arg Val
                485                 490                 495
Val Gln Arg Glu Lys Arg Ala Val Thr Leu Gly Ala Met Phe Leu Gly
            500                 505                 510
Phe Leu Gly Ala Ala Gly Ser Thr Met Gly Ala Arg Ser Leu Thr Leu
        515                 520                 525
Thr Val Gln Ala Arg Gln Leu Leu Ser Gly Ile Val Gln Gln Gln Asn
    530                 535                 540
Asn Leu Leu Arg Ala Ile Glu Ala Gln Gln His Leu Leu Gln Leu Thr
545                 550                 555                 560
Val Trp Gly Ile Lys Gln Leu Gln Ala Arg Val Leu Ala Val Glu Arg
                565                 570                 575
Tyr Leu Lys Asp Gln Gln Leu Leu Gly Ile Trp Gly Cys Ser Gly Lys
            580                 585                 590
Leu Ile Cys Thr Thr Ala Val Pro Trp Asn Ala Ser Trp Ser Asn Lys
        595                 600                 605
Ser Leu Asp Gln Ile Trp Asn Asn Met Thr Trp Met Glu Trp Glu Arg
    610                 615                 620
Glu Ile Asp Asn Tyr Thr Asn Leu Ile Tyr Thr Leu Ile Glu Glu Ser
625                 630                 635                 640
Gln Asn Gln Gln Glu Lys Asn Glu Gln Glu Leu Leu Glu Leu Asp Lys
                645                 650                 655
Trp Ala Ser Leu Trp Asn Trp Phe Asp Ile Ser Lys Trp Leu Trp Tyr
            660                 665                 670
Ile Lys Ile Phe Ile Met Ile Val Gly Gly Leu Val Gly Leu Arg Ile
        675                 680                 685
Val Phe Thr Val Leu Ser Ile Val Asn Arg Val Arg Gln Gly Tyr Ser
    690                 695                 700
Pro Leu Ser Phe Gln Thr Arg Phe Pro Ala Pro Arg Gly Pro Asp Arg
705                 710                 715                 720
Pro Glu Gly Ile Glu Glu Gly Gly Glu Arg Asp Arg Asp Arg Ser
                725                 730                 735
Ser Pro Leu Val His Gly Leu Leu Ala Leu Ile Trp Asp Asp Leu Arg
            740                 745                 750
Ser Leu Cys Leu Phe Ser Tyr His Arg Leu Arg Asp Leu Ile Leu Ile
        755                 760                 765
Ala Ala Arg Ile Val Glu Leu Leu Gly Arg Arg Gly Trp Glu Ala Leu
    770                 775                 780
Lys Tyr Trp Gly Asn Leu Leu Gln Tyr Trp Ile Gln Glu Leu Lys Asn
785                 790                 795                 800
Ser Ala Val Ser Leu Phe Asp Ala Ile Ala Ile Ala Val Ala Glu Gly
                805                 810                 815
Thr Asp Arg Ile Ile Glu Val Ala Gln Arg Ile Gly Arg Ala Phe Leu
            820                 825                 830
His Ile Pro Arg Arg Ile Arg Gln Gly Phe Glu Arg Ala Leu Leu
        835                 840                 845
```

```
<210> SEQ ID NO 2
<211> LENGTH: 1067
<212> TYPE: PRT
<213> ORGANISM: RVFV Glycoprotein a.a.

<400> SEQUENCE: 2

Met Ala Gly Ile Ala Met Thr Val Leu Pro Ala Leu Ala Val Phe Ala
1               5                   10                  15

Leu Ala Pro Val Val Phe Ala Glu Asp Pro His Leu Arg Asn Arg Pro
            20                  25                  30

Gly Lys Gly His Asn Tyr Ile Asp Gly Met Thr Gln Glu Asp Ala Thr
        35                  40                  45

Cys Lys Pro Val Thr Tyr Ala Gly Ala Cys Ser Ser Phe Asp Val Leu
    50                  55                  60

Leu Glu Lys Gly Lys Phe Pro Leu Phe Gln Ser Tyr Ala His His Arg
65                  70                  75                  80

Thr Leu Leu Glu Ala Val His Asp Thr Ile Ile Ala Lys Ala Asp Pro
                85                  90                  95

Pro Ser Cys Asp Leu Gln Ser Ala His Gly Asn Pro Cys Met Lys Glu
            100                 105                 110

Lys Leu Val Met Lys Thr His Cys Pro Asn Asp Tyr Gln Ser Ala His
        115                 120                 125

Tyr Leu Asn Asn Asp Gly Lys Met Ala Ser Val Lys Cys Pro Pro Lys
130                 135                 140

Tyr Gly Leu Thr Glu Asp Cys Asn Phe Cys Arg Gln Met Thr Gly Ala
145                 150                 155                 160

Ser Leu Lys Lys Gly Ser Tyr Pro Leu Gln Asp Leu Phe Cys Gln Ser
                165                 170                 175

Ser Glu Asp Asp Gly Ser Lys Leu Lys Thr Lys Met Lys Gly Val Cys
            180                 185                 190

Glu Val Gly Val Gln Ala His Lys Lys Cys Asp Gly Gln Leu Ser Thr
        195                 200                 205

Ala His Glu Val Val Pro Phe Ala Val Phe Lys Asn Ser Lys Lys Val
    210                 215                 220

Tyr Leu Asp Lys Leu Asp Leu Lys Thr Glu Glu Asn Leu Leu Pro Asp
225                 230                 235                 240

Ser Phe Val Cys Phe Glu His Lys Gly Gln Tyr Lys Gly Thr Met Asp
                245                 250                 255

Ser Gly Gln Thr Lys Arg Glu Leu Lys Ser Phe Asp Ile Ser Gln Cys
            260                 265                 270

Pro Lys Ile Gly Gly His Gly Ser Lys Lys Cys Thr Gly Asp Ala Ala
        275                 280                 285

Phe Cys Ser Ala Tyr Glu Cys Thr Ala Gln Tyr Ala Asn Ala Tyr Cys
    290                 295                 300

Ser His Ala Asn Gly Ser Gly Ile Val Gln Ile Gln Val Ser Gly Val
305                 310                 315                 320

Trp Lys Lys Pro Leu Cys Val Gly Tyr Glu Arg Val Val Val Lys Arg
                325                 330                 335

Glu Leu Ser Ala Lys Pro Ile Gln Arg Val Glu Pro Cys Thr Thr Cys
            340                 345                 350

Ile Thr Lys Cys Glu Pro His Gly Leu Val Val Arg Ser Thr Gly Phe
        355                 360                 365

Lys Ile Ser Ser Ala Val Ala Cys Ala Ser Gly Val Cys Val Thr Gly
    370                 375                 380
```

```
Ser Gln Ser Pro Ser Thr Glu Ile Thr Leu Lys Tyr Pro Gly Ile Ser
385                 390                 395                 400

Gln Ser Ser Gly Gly Asp Ile Gly Val His Met Ala His Asp Asp Gln
            405                 410                 415

Ser Val Ser Ser Lys Ile Val Ala His Cys Pro Pro Gln Asp Pro Cys
            420                 425                 430

Leu Val His Gly Cys Ile Val Cys Ala His Gly Leu Ile Asn Tyr Gln
            435                 440                 445

Cys His Thr Ala Leu Ser Ala Phe Val Val Phe Val Phe Ser Ser
        450                 455                 460

Ile Ala Ile Ile Cys Leu Ala Val Leu Tyr Arg Val Leu Lys Cys Leu
465                 470                 475                 480

Lys Ile Ala Pro Arg Lys Val Leu Asn Pro Leu Met Trp Ile Thr Ala
            485                 490                 495

Phe Ile Arg Trp Ile Tyr Lys Lys Met Val Ala Arg Val Ala His Asn
            500                 505                 510

Ile Asn Gln Val Asn Arg Glu Ile Gly Trp Met Glu Gly Gln Leu
515                 520                 525

Val Leu Gly Asn Pro Ala Pro Ile Pro Arg His Ala Pro Ile Pro Arg
530                 535                 540

Tyr Ser Thr Tyr Leu Met Leu Leu Leu Ile Val Ser Tyr Ala Ser Ala
545                 550                 555                 560

Cys Ser Glu Leu Ile Gln Ala Ser Ser Arg Ile Thr Thr Cys Ser Thr
                565                 570                 575

Glu Gly Val Asn Thr Lys Cys Arg Leu Ser Gly Thr Ala Leu Ile Arg
            580                 585                 590

Ala Gly Ser Val Gly Ala Glu Ala Cys Leu Met Leu Lys Gly Val Lys
        595                 600                 605

Glu Asp Gln Thr Lys Phe Leu Lys Ile Lys Thr Val Ser Ser Glu Leu
610                 615                 620

Ser Cys Arg Glu Gly Gln Ser Tyr Trp Thr Gly Ser Ile Ser Pro Lys
625                 630                 635                 640

Cys Leu Ser Ser Arg Arg Cys His Leu Val Gly Glu Cys His Val Asn
            645                 650                 655

Arg Cys Leu Ser Trp Arg Asp Asn Glu Thr Ser Ala Glu Phe Ser Phe
            660                 665                 670

Val Gly Glu Ser Thr Thr Met Arg Glu Asn Lys Cys Phe Glu Gln Cys
        675                 680                 685

Gly Gly Trp Gly Cys Gly Cys Phe Asn Val Asn Pro Ser Cys Leu Phe
    690                 695                 700

Val His Thr Tyr Leu Gln Ser Val Arg Lys Glu Ala Leu Arg Val Phe
705                 710                 715                 720

Asn Cys Ile Asp Trp Val His Lys Leu Thr Leu Glu Ile Thr Asp Phe
            725                 730                 735

Asp Gly Ser Val Ser Thr Ile Asp Leu Gly Ala Ser Ser Ser Arg Phe
            740                 745                 750

Thr Asn Trp Gly Ser Val Ser Leu Ser Leu Asp Ala Glu Gly Ile Ser
        755                 760                 765

Gly Ser Asn Ser Phe Ser Phe Ile Glu Ser Pro Ser Lys Gly Tyr Ala
        770                 775                 780

Ile Val Asp Glu Pro Phe Ser Glu Ile Pro Arg Gln Gly Phe Leu Gly
785                 790                 795                 800

Glu Ile Arg Cys Asn Ser Glu Ser Ser Val Leu Ser Ala His Glu Ser
```

Cys Leu Arg Ala Pro Asn Leu Ile Ser Tyr Lys Pro Met Ile Asp Gln
                 805                 810                 815
820

Leu Glu Cys Thr Thr Asn Leu Ile Asp Pro Phe Val Phe Glu Arg
        835                 840                 845

Gly Ser Leu Pro Gln Thr Arg Asn Asp Lys Thr Phe Ala Ala Ser Lys
850                 855                 860

Gly Asn Arg Gly Val Gln Ala Phe Ser Lys Gly Ser Val Gln Ala Asp
865                 870                 875                 880

Leu Thr Leu Met Phe Asp Asn Phe Glu Val Asp Phe Val Gly Ala Ala
                885                 890                 895

Val Ser Cys Asp Ala Ala Phe Leu Asn Leu Thr Gly Cys Tyr Ser Cys
                900                 905                 910

Asn Ala Gly Ala Arg Val Cys Leu Ser Ile Thr Ser Thr Gly Thr Gly
                915                 920                 925

Ser Leu Ser Ala His Asn Lys Asp Gly Ser Leu His Ile Val Leu Pro
930                 935                 940

Ser Glu Asn Gly Thr Lys Asp Gln Cys Gln Ile Leu His Phe Thr Val
945                 950                 955                 960

Pro Glu Val Glu Glu Phe Met Tyr Ser Cys Asp Gly Asp Glu Arg
                965                 970                 975

Pro Leu Leu Val Lys Gly Thr Leu Ile Ala Ile Asp Pro Phe Asp Asp
                980                 985                 990

Arg Arg Glu Ala Gly Gly Glu Ser Thr Val Val Asn Pro Lys Ser Gly
                995                 1000                1005

Ser Trp Asn Phe Phe Asp Trp Phe Ser Gly Leu Met Ser Trp Phe
    1010                1015                1020

Gly Gly Pro Leu Lys Thr Ile Leu Leu Ile Cys Leu Tyr Val Ala
    1025                1030                1035

Leu Ser Ile Gly Leu Phe Phe Leu Leu Ile Tyr Leu Gly Arg Thr
    1040                1045                1050

Gly Leu Ser Lys Met Trp Leu Ala Ala Thr Lys Lys Ala Ser
    1055                1060                1065

<210> SEQ ID NO 3
<211> LENGTH: 853
<212> TYPE: PRT
<213> ORGANISM: HIV 89.6 Envelope Glycoprotein

<400> SEQUENCE: 3

Met Arg Val Lys Glu Ile Arg Lys Asn Trp Gln His Leu Arg Gly Gly
1               5                   10                  15

Ile Leu Leu Leu Gly Met Leu Met Ile Cys Ser Ala Ala Lys Glu Lys
                20                  25                  30

Thr Trp Val Thr Ile Tyr Tyr Gly Val Pro Val Trp Arg Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asn Met Val Asp Gln Met His Glu Asp Ile Ile Ser Leu Trp Asp
                100                 105                 110

-continued

Glu Ser Leu Lys Pro Cys Val Lys Leu Thr Pro Leu Cys Val Thr Leu
            115                 120                 125

Asn Cys Thr Asn Leu Asn Ile Thr Lys Asn Thr Thr Asn Pro Thr Ser
130                 135                 140

Ser Ser Trp Gly Met Met Glu Lys Gly Glu Ile Lys Asn Cys Ser Phe
145                 150                 155                 160

Tyr Ile Thr Thr Ser Ile Arg Asn Lys Val Lys Lys Glu Tyr Ala Leu
                165                 170                 175

Phe Asn Arg Leu Asp Val Val Pro Ile Glu Asn Thr Asn Asn Thr Lys
                180                 185                 190

Tyr Arg Leu Ile Ser Cys Asn Thr Ser Val Ile Thr Gln Ala Cys Pro
            195                 200                 205

Lys Val Ser Phe Gln Pro Ile Pro Ile His Tyr Cys Val Pro Ala Gly
210                 215                 220

Phe Ala Met Leu Lys Cys Asn Asn Lys Thr Phe Asn Gly Ser Gly Pro
225                 230                 235                 240

Cys Thr Asn Val Ser Thr Val Gln Cys Thr His Gly Ile Arg Pro Val
                245                 250                 255

Val Ser Thr Gln Leu Leu Leu Asn Gly Ser Leu Ala Glu Glu Asp Ile
            260                 265                 270

Val Ile Arg Ser Glu Asn Phe Thr Asp Asn Ala Lys Thr Ile Ile Val
            275                 280                 285

Gln Leu Asn Glu Ser Val Val Ile Asn Cys Thr Arg Pro Asn Asn Asn
290                 295                 300

Thr Arg Arg Arg Leu Ser Ile Gly Pro Gly Arg Ala Phe Tyr Ala Arg
305                 310                 315                 320

Arg Asn Ile Ile Gly Asp Ile Arg Gln Ala His Cys Asn Ile Ser Arg
                325                 330                 335

Ala Lys Trp Asn Asn Thr Leu Gln Gln Ile Val Ile Lys Leu Arg Glu
            340                 345                 350

Lys Phe Arg Asn Lys Thr Ile Ala Phe Asn Gln Ser Ser Gly Gly Asp
            355                 360                 365

Pro Glu Ile Val Met His Ser Phe Asn Cys Gly Gly Glu Phe Phe Tyr
370                 375                 380

Cys Asn Thr Ala Gln Leu Phe Asn Ser Thr Trp Asn Val Thr Gly Gly
385                 390                 395                 400

Thr Asn Gly Thr Glu Gly Asn Asp Ile Ile Thr Leu Gln Cys Arg Ile
                405                 410                 415

Lys Gln Ile Ile Asn Met Trp Gln Lys Val Gly Lys Ala Met Tyr Ala
            420                 425                 430

Pro Pro Ile Thr Gly Gln Ile Arg Cys Ser Ser Asn Ile Thr Gly Leu
            435                 440                 445

Leu Leu Thr Arg Asp Gly Gly Asn Ser Thr Glu Thr Glu Thr Glu Ile
450                 455                 460

Phe Arg Pro Gly Gly Gly Asp Met Arg Asp Asn Trp Arg Ser Glu Leu
465                 470                 475                 480

Tyr Lys Tyr Lys Val Val Arg Ile Glu Pro Ile Gly Val Ala Pro Thr
                485                 490                 495

Arg Ala Lys Arg Arg Thr Val Gln Arg Glu Lys Arg Ala Val Gly Ile
            500                 505                 510

Gly Ala Val Phe Leu Gly Phe Leu Gly Ala Ala Gly Ser Thr Met Gly
            515                 520                 525

Ala Ala Ser Val Thr Leu Thr Val Gln Ala Arg Leu Leu Leu Ser Gly

```
                530              535              540
Ile Val Gln Gln Gln Asn Asn Leu Leu Arg Ala Ile Glu Ala Gln Gln
545              550              555              560

His Met Leu Gln Leu Thr Val Trp Gly Ile Lys Gln Leu Gln Ala Arg
                565              570              575

Val Leu Ala Leu Glu Arg Tyr Leu Arg Asp Gln Gln Leu Met Gly Ile
                580              585              590

Trp Gly Cys Ser Gly Lys Leu Ile Cys Thr Thr Ser Val Pro Trp Asn
                595              600              605

Val Ser Trp Ser Asn Lys Ser Val Asp Asp Ile Trp Asn Asn Met Thr
610              615              620

Trp Met Glu Trp Glu Arg Glu Ile Asp Asn Tyr Thr Asp Tyr Ile Tyr
625              630              635              640

Asp Leu Leu Glu Lys Ser Gln Thr Gln Gln Glu Lys Asn Glu Lys Glu
                645              650              655

Leu Leu Glu Leu Asp Lys Trp Ala Ser Leu Trp Asn Trp Phe Asp Ile
                660              665              670

Thr Asn Trp Leu Trp Tyr Ile Arg Leu Phe Ile Met Ile Val Gly Gly
                675              680              685

Leu Ile Gly Leu Arg Ile Val Phe Ala Val Leu Ser Ile Val Asn Arg
690              695              700

Val Arg Gln Gly Tyr Ser Pro Leu Ser Phe Gln Thr Leu Leu Pro Ala
705              710              715              720

Ser Arg Gly Pro Asp Arg Pro Glu Gly Thr Glu Glu Glu Gly Gly Glu
                725              730              735

Arg Asp Arg Asp Arg Ser Gly Pro Leu Val Asn Gly Phe Leu Ala Leu
                740              745              750

Phe Trp Val Asp Leu Arg Asn Leu Cys Leu Phe Leu Tyr His Leu Leu
                755              760              765

Arg Asn Leu Leu Leu Ile Val Thr Arg Ile Val Glu Leu Leu Gly Arg
770              775              780

Arg Gly Trp Glu Ala Leu Lys Tyr Trp Trp Asn Leu Leu Gln Tyr Trp
785              790              795              800

Ser Gln Glu Leu Lys Asn Ser Ala Val Ser Leu Leu Asn Ala Thr Ala
                805              810              815

Ile Ala Val Ala Glu Gly Thr Asp Arg Val Ile Lys Ile Val Gln Arg
                820              825              830

Ala Cys Arg Ala Ile Arg Asn Ile Pro Thr Arg Ile Arg Gln Gly Leu
                835              840              845

Glu Arg Ala Leu Leu
850

<210> SEQ ID NO 4
<211> LENGTH: 507
<212> TYPE: PRT
<213> ORGANISM: RVFV GC

<400> SEQUENCE: 4

Cys Ser Glu Leu Ile Gln Ala Ser Ser Arg Ile Thr Thr Cys Ser Thr
1               5                10               15

Glu Gly Val Asn Thr Lys Cys Arg Leu Ser Gly Thr Ala Leu Ile Arg
                20               25               30

Ala Gly Ser Val Gly Ala Glu Ala Cys Leu Met Leu Lys Gly Val Lys
                35               40               45
```

```
Glu Asp Gln Thr Lys Phe Leu Lys Ile Lys Thr Val Ser Ser Glu Leu
 50                  55                  60
Ser Cys Arg Glu Gly Gln Ser Tyr Trp Thr Gly Ser Ile Ser Pro Lys
 65                  70                  75                  80
Cys Leu Ser Ser Arg Cys His Leu Val Gly Glu Cys His Val Asn
                 85                  90                  95
Arg Cys Leu Ser Trp Arg Asp Asn Glu Thr Ser Ala Glu Phe Ser Phe
                100                 105                 110
Val Gly Glu Ser Thr Thr Met Arg Glu Asn Lys Cys Phe Glu Gln Cys
                115                 120                 125
Gly Gly Trp Gly Cys Gly Cys Phe Asn Val Asn Pro Ser Cys Leu Phe
            130                 135                 140
Val His Thr Tyr Leu Gln Ser Val Arg Lys Glu Ala Leu Arg Val Phe
145                 150                 155                 160
Asn Cys Ile Asp Trp Val His Lys Leu Thr Leu Glu Ile Thr Asp Phe
                165                 170                 175
Asp Gly Ser Val Ser Thr Ile Asp Leu Gly Ala Ser Ser Arg Phe
                180                 185                 190
Thr Asn Trp Gly Ser Val Ser Leu Ser Leu Asp Ala Glu Gly Ile Ser
            195                 200                 205
Gly Ser Asn Ser Phe Ser Phe Ile Glu Ser Pro Ser Lys Gly Tyr Ala
            210                 215                 220
Ile Val Asp Glu Pro Phe Ser Glu Ile Pro Arg Gln Gly Phe Leu Gly
225                 230                 235                 240
Glu Ile Arg Cys Asn Ser Glu Ser Ser Val Leu Ser Ala His Glu Ser
                245                 250                 255
Cys Leu Arg Ala Pro Asn Leu Ile Ser Tyr Lys Pro Met Ile Asp Gln
                260                 265                 270
Leu Glu Cys Thr Thr Asn Leu Ile Asp Pro Phe Val Val Phe Glu Arg
            275                 280                 285
Gly Ser Leu Pro Gln Thr Arg Asn Asp Lys Thr Phe Ala Ala Ser Lys
            290                 295                 300
Gly Asn Arg Gly Val Gln Ala Phe Ser Lys Gly Ser Val Gln Ala Asp
305                 310                 315                 320
Leu Thr Leu Met Phe Asp Asn Phe Glu Val Asp Phe Val Gly Ala Ala
                325                 330                 335
Val Ser Cys Asp Ala Ala Phe Leu Asn Leu Thr Gly Cys Tyr Ser Cys
                340                 345                 350
Asn Ala Gly Ala Arg Val Cys Leu Ser Ile Thr Ser Thr Gly Thr Gly
            355                 360                 365
Ser Leu Ser Ala His Asn Lys Asp Gly Ser Leu His Ile Val Leu Pro
            370                 375                 380
Ser Glu Asn Gly Thr Lys Asp Gln Cys Gln Ile Leu His Phe Thr Val
385                 390                 395                 400
Pro Glu Val Glu Glu Phe Met Tyr Ser Cys Asp Gly Asp Glu Arg
                405                 410                 415
Pro Leu Leu Val Lys Gly Thr Leu Ile Ala Ile Asp Pro Phe Asp Asp
                420                 425                 430
Arg Arg Glu Ala Gly Gly Glu Ser Thr Val Val Asn Pro Lys Ser Gly
            435                 440                 445
Ser Trp Asn Phe Phe Asp Trp Phe Ser Gly Leu Met Ser Trp Phe Gly
            450                 455                 460
Gly Pro Leu Lys Thr Ile Leu Leu Ile Cys Leu Tyr Val Ala Leu Ser
```

```
            465                 470                 475                 480
Ile Gly Leu Phe Phe Leu Leu Ile Tyr Leu Gly Arg Thr Gly Leu Ser
                    485                 490                 495
Lys Met Trp Leu Ala Ala Thr Lys Lys Ala Ser
            500                 505

<210> SEQ ID NO 5
<211> LENGTH: 527
<212> TYPE: PRT
<213> ORGANISM: RVFV GN

<400> SEQUENCE: 5

Glu Asp Pro His Leu Arg Asn Arg Pro Gly Lys Gly His Asn Tyr Ile
1               5                   10                  15

Asp Gly Met Thr Gln Glu Asp Ala Thr Cys Lys Pro Val Thr Tyr Ala
            20                  25                  30

Gly Ala Cys Ser Ser Phe Asp Val Leu Leu Glu Lys Gly Lys Phe Pro
        35                  40                  45

Leu Phe Gln Ser Tyr Ala His His Arg Thr Leu Leu Glu Ala Val His
    50                  55                  60

Asp Thr Ile Ile Ala Lys Ala Asp Pro Pro Ser Cys Asp Leu Gln Ser
65                  70                  75                  80

Ala His Gly Asn Pro Cys Met Lys Glu Lys Leu Val Met Lys Thr His
                85                  90                  95

Cys Pro Asn Asp Tyr Gln Ser Ala His Tyr Leu Asn Asn Asp Gly Lys
            100                 105                 110

Met Ala Ser Val Lys Cys Pro Pro Lys Tyr Gly Leu Thr Glu Asp Cys
        115                 120                 125

Asn Phe Cys Arg Gln Met Thr Gly Ala Ser Leu Lys Lys Gly Ser Tyr
    130                 135                 140

Pro Leu Gln Asp Leu Phe Cys Gln Ser Ser Glu Asp Asp Gly Ser Lys
145                 150                 155                 160

Leu Lys Thr Lys Met Lys Gly Val Cys Glu Val Gly Val Gln Ala His
                165                 170                 175

Lys Lys Cys Asp Gly Gln Leu Ser Thr Ala His Glu Val Val Pro Phe
            180                 185                 190

Ala Val Phe Lys Asn Ser Lys Lys Val Tyr Leu Asp Lys Leu Asp Leu
        195                 200                 205

Lys Thr Glu Glu Asn Leu Leu Pro Asp Ser Phe Val Cys Phe Glu His
    210                 215                 220

Lys Gly Gln Tyr Lys Gly Thr Met Asp Ser Gly Gln Thr Lys Arg Glu
225                 230                 235                 240

Leu Lys Ser Phe Asp Ile Ser Gln Cys Pro Lys Ile Gly Gly His Gly
                245                 250                 255

Ser Lys Lys Cys Thr Gly Asp Ala Ala Phe Cys Ser Ala Tyr Glu Cys
            260                 265                 270

Thr Ala Gln Tyr Ala Asn Ala Tyr Cys Ser His Ala Asn Gly Ser Gly
        275                 280                 285

Ile Val Gln Ile Gln Val Ser Gly Val Trp Lys Lys Pro Leu Cys Val
    290                 295                 300

Gly Tyr Glu Arg Val Val Val Lys Arg Glu Leu Ser Ala Lys Pro Ile
305                 310                 315                 320

Gln Arg Val Glu Pro Cys Thr Thr Cys Ile Thr Lys Cys Glu Pro His
                325                 330                 335
```

-continued

```
Gly Leu Val Val Arg Ser Thr Gly Phe Lys Ile Ser Ser Ala Val Ala
            340                 345                 350

Cys Ala Ser Gly Val Cys Val Thr Gly Ser Gln Ser Pro Ser Thr Glu
        355                 360                 365

Ile Thr Leu Lys Tyr Pro Gly Ile Ser Gln Ser Ser Gly Gly Asp Ile
    370                 375                 380

Gly Val His Met Ala His Asp Asp Gln Ser Val Ser Ser Lys Ile Val
385                 390                 395                 400

Ala His Cys Pro Pro Gln Asp Pro Cys Leu Val His Gly Cys Ile Val
                405                 410                 415

Cys Ala His Gly Leu Ile Asn Tyr Gln Cys His Thr Ala Leu Ser Ala
            420                 425                 430

Phe Val Val Val Phe Val Phe Ser Ser Ile Ala Ile Ile Cys Leu Ala
        435                 440                 445

Val Leu Tyr Arg Val Leu Lys Cys Leu Lys Ile Ala Pro Arg Lys Val
    450                 455                 460

Leu Asn Pro Leu Met Trp Ile Thr Ala Phe Ile Arg Trp Ile Tyr Lys
465                 470                 475                 480

Lys Met Val Ala Arg Val Ala His Asn Ile Asn Gln Val Asn Arg Glu
                485                 490                 495

Ile Gly Trp Met Glu Gly Gly Gln Leu Val Leu Gly Asn Pro Ala Pro
            500                 505                 510

Ile Pro Arg His Ala Pro Ile Pro Arg Tyr Ser Thr Tyr Leu Met
        515                 520                 525

<210> SEQ ID NO 6
<211> LENGTH: 26
<212> TYPE: PRT
<213> ORGANISM: N-terminus of the SIV Env Glyocoprotein-41 TM domain

<400> SEQUENCE: 6

Tyr Ile Gln Tyr Gly Val Tyr Ile Val Val Gly Val Ile Leu Leu Arg
1               5                   10                  15

Ile Val Ile Tyr Ile Val Gln Met Leu Ala
            20                  25

<210> SEQ ID NO 7
<211> LENGTH: 232
<212> TYPE: PRT
<213> ORGANISM: extracellular coding domain of the FL gene

<400> SEQUENCE: 7

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
        35                  40                  45

Leu Thr Asp His Leu Leu Lys Asp Tyr Pro Val Thr Val Ala Val Asn
    50                  55                  60

Leu Gln Asp Glu Lys His Cys Lys Ala Leu Trp Ser Leu Phe Leu Ala
65                  70                  75                  80
```

```
Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Leu Leu Leu
            180                 185                 190

Leu Leu Leu Leu Leu Leu Pro Leu Thr Leu Val Leu Leu Ala Ala Ala
        195                 200                 205

Trp Gly Leu Arg Trp Gln Arg Ala Arg Arg Gly Glu Leu His Pro
    210                 215                 220

Gly Val Pro Leu Pro Ser His Pro
225                 230
```

<210> SEQ ID NO 8
<211> LENGTH: 164
<212> TYPE: PRT
<213> ORGANISM: SIV mac239 Env cytoplasmic domain

<400> SEQUENCE: 8

```
Lys Leu Arg Gln Gly Tyr Arg Pro Val Phe Ser Ser Pro Pro Ser Tyr
1               5                   10                  15

Phe Gln Gln Thr His Ile Gln Gln Asp Pro Ala Leu Pro Thr Arg Glu
                20                  25                  30

Gly Lys Glu Arg Asp Gly Gly Glu Gly Gly Gly Asn Ser Ser Trp Pro
            35                  40                  45

Trp Gln Ile Glu Tyr Ile His Phe Leu Ile Arg Gln Leu Ile Arg Leu
        50                  55                  60

Leu Thr Trp Leu Phe Ser Asn Cys Arg Thr Leu Leu Ser Arg Val Tyr
65                  70                  75                  80

Gln Ile Leu Gln Pro Ile Leu Gln Arg Leu Ser Ala Thr Leu Gln Arg
                85                  90                  95

Ile Arg Glu Val Leu Arg Thr Glu Leu Thr Tyr Leu Gln Tyr Gly Trp
            100                 105                 110

Ser Tyr Phe His Glu Ala Val Gln Ala Val Trp Arg Ser Ala Thr Glu
        115                 120                 125

Thr Leu Ala Gly Ala Trp Gly Asp Leu Trp Glu Thr Leu Arg Arg Gly
    130                 135                 140

Gly Arg Trp Ile Leu Ala Ile Pro Arg Arg Ile Arg Gln Gly Leu Glu
145                 150                 155                 160

Leu Thr Leu Leu
```

<210> SEQ ID NO 9
<211> LENGTH: 23
<212> TYPE: PRT
<213> ORGANISM: tPA signal peptide

<400> SEQUENCE: 9

Met Asp Ala Met Lys Arg Gly Leu Cys Cys Val Leu Leu Leu Cys Gly

Ala Val Phe Val Ser Ala Arg
        20

<210> SEQ ID NO 10
<211> LENGTH: 40
<212> TYPE: PRT
<213> ORGANISM: GPI-anchoring seq. access no. x52645

<400> SEQUENCE: 10

Leu Ala Val Ser Thr Ile Ser Ser Phe Phe Pro Gly Tyr Gln Val
1               5                   10                  15

Ser Phe Cys Leu Val Met Val Leu Phe Ala Val Asp Thr Gly Leu
            20                  25                  30

Tyr Phe Ser Val Lys Thr Asn Ile
        35                  40

<210> SEQ ID NO 11
<211> LENGTH: 300
<212> TYPE: PRT
<213> ORGANISM: C3d sequence

<400> SEQUENCE: 11

Thr Val Ile Ala Val His Tyr Leu Asp Gln Thr Glu Gln Trp Glu Lys
1               5                   10                  15

Phe Gly Ile Glu Lys Arg Gln Glu Ala Leu Glu Leu Ile Lys Lys Gly
            20                  25                  30

Tyr Thr Gln Gln Leu Ala Phe Lys Gln Pro Ser Ser Ala Tyr Ala Ala
        35                  40                  45

Phe Asn Asn Arg Pro Pro Ser Thr Trp Leu Thr Ala Tyr Val Val Lys
    50                  55                  60

Val Phe Ser Leu Ala Ala Asn Leu Ile Ala Ile Asp Ser His Val Leu
65                  70                  75                  80

Cys Gly Ala Val Lys Trp Leu Ile Leu Glu Lys Gln Lys Pro Asp Gly
                85                  90                  95

Val Phe Gln Glu Asp Gly Pro Val Ile His Gln Glu Met Ile Gly Gly
            100                 105                 110

Phe Arg Asn Ala Lys Glu Ala Asp Val Ser Leu Thr Ala Phe Val Leu
        115                 120                 125

Ile Ala Leu Gln Glu Ala Arg Asp Ile Cys Glu Gly Gln Val Asn Ser
    130                 135                 140

Leu Pro Gly Ser Ile Asn Lys Ala Gly Glu Tyr Ile Glu Ala Ser Tyr
145                 150                 155                 160

Met Asn Leu Gln Arg Pro Tyr Thr Val Ala Ile Ala Gly Tyr Ala Leu
                165                 170                 175

Ala Leu Met Asn Lys Leu Glu Glu Pro Tyr Leu Gly Lys Phe Leu Asn
            180                 185                 190

Thr Ala Lys Asp Arg Asn Arg Trp Glu Glu Pro Asp Gln Gln Leu Tyr
        195                 200                 205

Asn Val Glu Ala Thr Ser Tyr Ala Leu Leu Ala Leu Leu Leu Leu Lys
    210                 215                 220

Asp Phe Asp Ser Val Pro Pro Val Val Arg Trp Leu Asn Glu Gln Arg
225                 230                 235                 240

Tyr Tyr Gly Gly Gly Tyr Gly Ser Thr Gln Ala Thr Phe Met Val Phe
                245                 250                 255

Gln Ala Leu Ala Gln Tyr Gln Thr Asp Val Pro Asp His Lys Asp Leu

```
                    260                 265                 270
Asn Met Asp Val Ser Phe His Leu Pro Ser Arg Ser Ser Ala Thr Thr
            275                 280                 285

Phe Arg Leu Leu Trp Glu Asn Gly Asn Leu Leu Arg
            290                 295                 300
```

VIRUS-LIKE PARTICLES, METHODS OF PREPARATION, AND IMMUNOGENIC COMPOSITIONS

CROSS-REFERENCE TO RELATED APPLICATION

This application is a continuation-in-part of U.S. application Ser. No. 10/514,462, filed Nov. 12, 2004, which is a 371 U.S.C. of International Patent Application No. PCT/US2003/015930, filed on May 19, 2003, which claims the benefit of priority to U.S. Provisional application Ser. No. 60/381,557, filed May 17, 2002, entitled Chimeric Virus-Like Particales as Vaccine Antigens, and U.S. Provisional application Ser. No. 60/454,115 filed Mar. 11, 2003, and entitled Rift Valley Fever Virus-Like Particale Vaccine, and U.S. Provisional application Ser. No. 60/454,139, filed Mar. 11, 2003 and entitled Targeting HIV Virus-like Particales To Dendritic Cells, and; U.S. Provisional application Ser. No. 60/454,584, filed Mar. 14, 2003, and entitled Rift Valley Fever Virus-Like Particle Vaccine, and; U.S. Provisional application Ser. No. 60/468,318, filed May 6, 2003, and entitled Ebola Virus Virus-Like Particles and U.S. Provisional application Ser. No. 60/471,246, filed May 16, 2003, and entitled Stabilizing Virus Envelope Protein Conformation for Inducing Neutralizing Antibody Responses by Treatment with Peptide Corresponding to the Helical Regions (also termed Heptad Repeat Regions) of the Viral Envelope Protein; which applications are entirely incorporated herein by reference in their entireties.

STATEMENT REGARDING FEDERALLY SPONSORED RESEARCH OR DEVELOPMENT

This invention was made with government support under grant numbers 1R21 AI53514, 1R21 AI44409, and 5R21 awarded by the National Institute of Health. The government has certain rights in the invention.

TECHNICAL FIELD

The present disclosure is generally related to virus-like particles, methods of preparing virus-like particles, immunogenic compositions that include virus-like particles, and methods of eliciting an immune response using immunogenic compositions that include virus-like particles.

BACKGROUND

Virus-like particles (VLPs) closely resemble mature virions, but they do not contain viral genomic material (e.g., viral genomic RNA). Therefore, VLPs are nonreplicative in nature, which make them safe for administration in the form of an immunogenic composition (e.g., vaccine). In addition, VLPs can express envelope glycoproteins on the surface of the VLP, which is the most physiological configuration. Moreover, since VLPs resemble intact virions and are multivalent particulate structures, VLPs may be more effective in inducing neutralizing antibodies to the envelope glycoprotein than soluble envelope antigens. Further, VLPs can be administered repeatedly to vaccinated hosts, unlike many recombinant vaccine approaches. An example of a VLP vaccine is the baculovirus-derived recombinant human papillomavirus type (HPV-16) L1 VLP, which was manufactured by Novavax, Inc.

Therefore, VLPs can be used to overcome problems encountered in previous attempts to create vaccines for various viruses such as human immunodeficiency virus (HIV), Ebola virus, severe acute respiratory syndrome (SARS), coronavirus, and Rift Valley Fever virus (RVFV).

SUMMARY

Briefly described, embodiments of the present disclosure include novel types of virus-like particles, methods of preparing virus-like particles, immunogenic compositions that include virus-like particles, and methods of eliciting an immune response using immunogenic compositions that include virus-like particles. One exemplary embodiment of a novel type of virus-like particle includes a virus-like particle (VLP) that includes a viral core protein that can self-assemble into the VLP core and at least one viral surface envelope glycoprotein expressed on the surface of the VLP. The viral protein and at least one of the viral surface envelope glycoprotein(s) are from different viruses. Another exemplary embodiment of a VLP includes a VLP having a viral core protein that can self assemble into a VLP core; at least one viral surface envelope glycoprotein expressed on the surface of the VLP; and at least one adjuvant molecule expressed on the surface of the VLP.

Another representative embodiment of the present disclosure includes an immunogenic composition. The immunogenic composition includes a pharmacologically acceptable carrier and at least one of the VLPs described above. Further, another representative embodiment of the present disclosure includes a method of generating an immunological response in a host by administering an effective amount of one or more of the immunogenic compositions described above to the host. Furthermore, another representative embodiment of the present disclosure includes a method of treating a condition by administering to a host in need of treatment an effective amount of one or more of the immunogenic compositions described above.

Still another representative embodiment of the present disclosure includes methods of determining exposure of a host to a virus. An exemplary method, among others, includes the steps of: contacting a biological fluid of the host with one or more of the VLPs discussed above, wherein the VLP is of the same virus type to which exposure is being determined, under conditions which are permissive for binding of antibodies in the biological fluid with the VLP; and detecting binding of antibodies within the biological fluid with the VLP, whereby exposure of the host to the virus is determined by the detection of antibodies bound to the VLP.

Still another representative embodiment of the present disclosure includes methods of making VLPs. An exemplary method, among others, includes the steps of: providing a viral core protein expression vector; providing a viral surface envelope surface glycoprotein expression vector; providing a membrane-anchored adjuvant molecule expression vector; and introducing into a cell the viral core protein expression vector, the viral surface envelope surface glycoprotein expression vector, and the adjuvant molecule expression vector and allowing for expression of the viral surface envelope surface glycoprotein and the adjuvant molecule, whereby the VLP is formed by the cells.

Another embodiment of a method of making VLPs includes the steps of: providing one or more expression vectors including polynucleotide sequences encoding for a viral core protein, at least one viral surface envelope glycoprotein, and at least one adjuvant molecule; introducing the one or more expression vectors into a host cell; and expressing the viral core protein, the at least one viral surface envelope glycoprotein, and the at least one adjuvant molecule, whereby the VLP is formed by the cell.

Other systems, methods, features, and advantages of the present disclosure will be or will become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3 illustrates some representative structural changes that can be made to another representative viral surface envelope glycoprotein.

FIGS. 5A through 5B illustrate graphs measuring various characteristics of a number of VLPs that were intranasally introduced into mice. In FIGS. 5A through 5D, "V" represents SHIV VLPs, "HA/V" represents HA/SHIV VLPs, "V+CT" represents SHIV VLPs (10 μg)+CT (10 μg), and "N" represents a negative control (PBS). In addition, the number in parentheses indicates the "μg's" of VLPs used for the immunization of the mice.

FIG. 5A illustrates a graph measuring serum IgG levels specific to HIV envelope glycoproteins. FIG. 5B illustrates a graph measuring splenocytes producing IFN-γ determined by ELISPOT assay. FIG. 5C illustrates a graph measuring HIV envelope glycoprotein-specific IgA in vaginal wash. FIG. 5D illustrates a graph measuring HIV envelope glycoprotein-specific IgA in fecal extracts.

FIG. 6 illustrates a schematic diagram of modified HIV envelope glycoproteins having the transmembrane and/or cytoplasmic domains of the HIV envelope glycoprotein replaced with the transmembrane and/or cytoplasmic domains of the MMTV envelope glycoprotein (MMTV), the baculovirus glycoprotein Gp64 (Gp64), the Lassa Fever virus glycoprotein (LFV), or the influenza surface glycoprotein HA (HA).

FIG. 7 also illustrates a schematic diagram of a modified HIV envelope glycoprotein having the signal peptide domain the HIV envelope glycoprotein replaced with the signal peptide domain of the mellitin protein.

FIG. 8A illustrates a Western blot analysis of VLPs. For characterization of SIV Gag and HIV Env incorporated into the sucrose gradient purified VLPs, VLPs were run on 8% SDS PAGE gel, and the Western blot was probed with monkey anti-SHIV 89.6 sera. FIG. 8B is a bar graph illustrating the HIV Env content in SHIV VLPs. Quantitative estimation of Env in VLPs was performed using ELISA plates coated with anti-HIV-1 Env C5 domain specific antibody (5 μg/ml). The amount of HIV Env was quantitatively determined using human patient antibody. Control: HIV Env-negative SIV Gag VLPs, WT: SHIV VLPs with wild type HIV Env 89.6, dV1V2: SHIV VLPs with dV1V2 mutant HIV Env, 3G: SHIV VLPs with 3G mutant HIV Env, 3G-dV2-1G: SHIV VLPs with 3G-dV2-1G mutant HIV Env.

FIG. 9A is a bar graph illustrating the HIV Env-specific total IgG antibody. The production of serum IgG against the HIV Env protein after the primary injection as well as after $1^{st}$ boost and $2^{nd}$ boost were measured using an ELISA. Mice were immunized with 50 μg of VLPs, 3 times at 4 weeks intervals. Results are expressed as the arithmetic mean 629±SD of 100-fold diluted serum samples from 6 mice per group. Error bars indicate standard deviation (SD). FIG. 9B is a bar graph illustrating the V3 loop peptide specific total IgG antibody. After the $2^{nd}$ boost immunization, total IgG antibody binding to the V3 loop peptide (100 fold-diluted sera) was determined using an ELISA. Pre-imm: Sera taken before immunization. The immunization groups are the same as those described in FIGS. 8A and B. Statistical significant differences are shown between 3G-dV2-1G and WT (**: $P<0.001$) and between WT and dV1V2 or 3G (*: $P<0.05$).

FIG. 10A: IgG1, FIG. 10B: IgG2a, FIG. 10C: IgG2b, FIG. 10D: IgG3 and FIG. 10E: IgA. Immunization groups are as described in FIG. 8.

FIG. 11A illustrates neutralization activity against HIV 89.6; FIG. 11C illustrates neutralization activity against HIV IIIB. The immunization groups are the same as those described in FIG. 8.

FIG.12A: IFN-γ, FIG. 12B: TNF-a, FIG. 12C: IL-4, and FIG. 12D: IL-10. The immunization groups are the same as those described in FIG. 8.

FIGS. 13A and 13B illustrate the concentrations of IFN-γ ELISA and IL-6 ELISA, respectively. The culture supernatants were harvested on day 3 after stimulation with an HIV Env 89.6 peptide and used to determine cytokines IFN-γ and IL-6 using ELISA. For FIGS. 13C, 13D, and 13E, cytokines (IL-2, 4, 5, respectively) were determined by ELISPOT in stimulation with an HIV Env 89.6 peptide. The spots for cytokine-producing cells from the spleen were counted and expressed based on $1.5 \times 10^6$ cells. Bars indicate standard deviations from six mice per group. The immunization groups are the same as those described in FIG. 8. Statistically significant differences are indicated between WT and mutants as * ($P<0.05$).

FIG. 14A illustrates unlabeled SHIV 89.6 VLPs with DC-enriched splenocytes; FIG. 14B illustrates CFSE-labeled SHIV 89.6 VLPs with DC-enriched splenocytes; and FIG. 14A illustrates CFSE-labeled VLPs containing 3G-dV2-1G Env with DC-enriched splenocytes.

FIG. 15A illustrates a Western blot analysis of RVFV VLPs. The VLPs were analyzed by SDS-PAGE (5 ug per lane) followed by Western blot using antibodies against the SIV Gag protein or monoclonal antibodies against the RVFV GN protein. Lanes 1, GP-Gag VLP; 2, SIV-Gag VLP; M, molecular weight marker. FIG. 15B presents graphs illustrating the amount of RVFV glycoproteins in VLPs. VLPs were lysed in lysis buffer and then coated onto a microtiter plate (1 ug per well). The levels of RVFV glycoproteins in VLPs were compared by ELISA using mouse sera against RVFV as the primary antibody and HRP-conjugated rabbit-anti-mouse IgG as the secondary antibody. The control wells were coated with 1 ug of SIV Gag VLPs. A standard curve was constructed by coating the microtiter plate with serial dilutions of purified RVFV GN-histag proteins mixed with 1 ug SIV Gag VLPs for calculating the amount of RVFV glycoproteins in VLPs.

FIG. 16 illustrates RVFV GP-SIV Gag VLPs absorbed on a carbon grid and stained with 1% uranyl acetate followed by examination under a transmission electron microscope. For the VLPs illustrated in FIG. 16B, RVFV GP-Gag VLPs were absorbed onto a carbon grid, followed by incubation with monoclonal antibodies against RVFV GN, washing, and then incubation with gold particle-conjugated anti-mouse secondary antibody. The grid was washed again and the VLPs were stained with 1% uranyl acetate followed by examination under a transmission electron microscope. Arrows indicate labeling gold particles on the surface of VLPs.

FIG. 17A illustrates detection of RVFV GN and SIV Gag proteins by Western blot using antibodies against RVFV GN or SIV Gag. 10 ul of each fraction (1 to 6 from top to bottom) were loaded per lane as indicated. Lanes M, molecular weight marker. FIG. 17B illustrates a comparison of the amounts of RVFV GP and SIV Gag proteins in each fraction by ELISA. A Microtiter plate was coated with 10 ul of each fraction per well and the levels of RVFV GP and SIV Gag proteins in each fraction were compared by ELISA using antibodies against RVFV or SIV Gag respectively. The controls wells (fractions 7) were coated with 10 ug of Ebola VP40 VLPs.

FIG. 18C illustrates neutralization of MP12 by individual serum samples from each group after the third immunization.

FIG. 19A is an illustration of a schematic diagram of GN-MuC and GC-MuC chimeric proteins in which the cytoplasmic tails of the GN and GC proteins were replaced with the MuLV Env cytoplasmic tail. FIGS. 19B and 19C illustrate the expression and release of MuLV Gag and chimeric GN-MuC and GC-MuC proteins in Sf9 cells by recombinant baculoviruses by Western Blot and ELISA, respectively. For FIG. 19B, lane 1 shows GN-MuC+GC-MuC+MuLV-Gag; lane 2 shows GN-MuC+GC-MuC; lane 3 shows MuLV-Gag; and lane M shows the molecular weight marker.

DETAILED DESCRIPTION

Embodiments of the present disclosure provide for virus-like particles, methods of using the virus-like particles, and methods of making virus-like particles that can be used in immunogenic compositions to treat conditions in a host, and the immunogenic compositions that include virus-like particles. The virus-like particles can be used to enhance immune responses (e.g., antibody production, cytotoxic T cell activity, and cytokine activity). In particular, virus-like particles can act as a prophylactic as a vaccine to prevent viral infections such as those caused by, for example, the human immunodeficiency virus (HIV), the Corona virus, the Influenza virus, the Paramyxovirus, the Herpesvirus, the Ebola virus, the Rift Valley Fever virus, the Hantaan Virus, the Lassa fever virus, and the Flavivirus.

Figure 1:
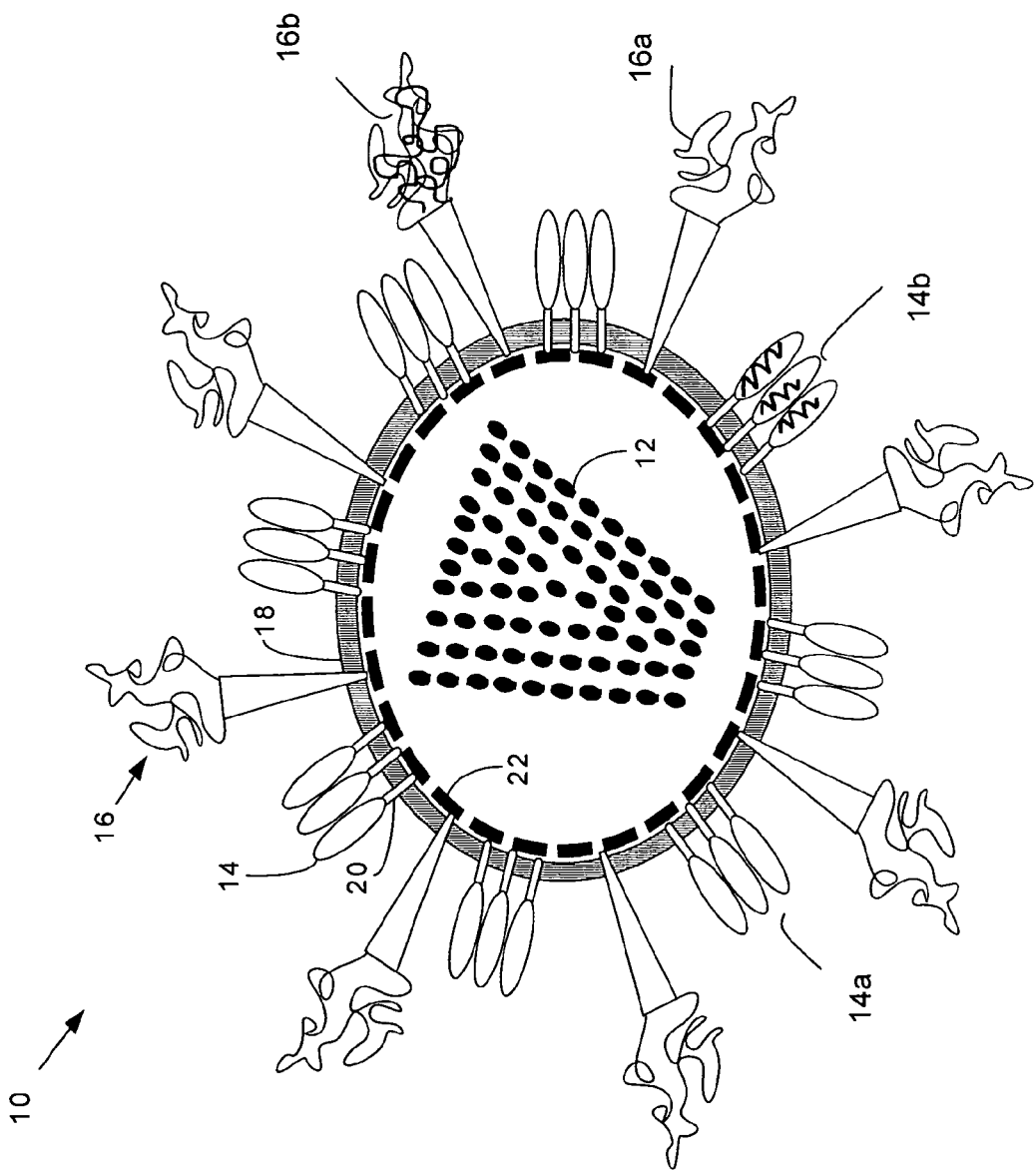
FIG. 1 illustrates a representative virus-like particle (VLP).

In general, the virus-like particle ("VLP") 10 includes at least a viral core protein 12 (hereinafter "viral protein") and at least one viral surface envelope glycoprotein 14 (e.g., type 1 (14a) or type 2 (14b) viral surface envelope glycoproteins, and so on), as shown in FIG. 1. In addition, the VLP can include at least one adjuvant molecule 16. The adjuvant molecules 16 can include more than one type of adjuvant molecule (e.g. 16a and 16b, and so on). Furthermore, the VLP can include a lipid membrane 18, viral glycoprotein transmembrane unit 20, and a matrix protein 22. In particular, chimeric VLPs are VLPs having at least one viral surface envelope glycoprotein 14 incorporated into the VLP 10, wherein the viral core protein 12 and at least one viral surface envelope glycoprotein 14 are from different viruses. Thus, chimeric VLPs also include VLPs wherein there are more than one type of viral surface envelope glycoprotein 14, 14a and/or 14b, and wherein one or both of 14a and 14b are from a different virus than the viral core protein 12. Furthermore, phenotypically mixed VLPs include VLPs having at least one adjuvant molecule 16 incorporated into the VLP, where at least one of the adjuvant molecule(s) 16 have an origin different from that of the viral core protein 12 and/or the viral surface envelope glycoprotein 14. Phenotypically mixed VLPs also include VLPs wherein there are more than one type of adjuvant molecule 16, 16a and 16b, and wherein one or both of 16a and 16b are from a different source from each other. Phenotypically mixed VLPs also include VLPs wherein the source of one or more adjuvant molecules (16a and/or 16b) is different from the source of at least one viral surface envelope glycoprotein 14 and/or from the viral core protein 12.

Viral proteins 12 include proteins that are capable of self-assembling into the VLP (Freed, E. O., *J. Virol.*, 76, 4679-87, (2002)). In particular, the viral core proteins 12 can include, but are not limited to, a viral Gag protein, in particular, a retrovirus gag protein [e.g. a HIV Gag viral protein (e.g., HIV-1 NL43 Gag (GenBank serial number AAA44987)), a simian immunodeficiency virus (SIV) Gag viral protein (e.g., SIVmac239 Gag (GenBank serial number CAA68379)), or a murine leukemia virus (MuLV) Gag viral protein (e.g., MuLV Gag (GenBank serial number S70394))], a retrovirus matrix protein, a rhabdovirus matrix protein M protein [e.g., a vesicular stomatis virus (VSV) M protein (e.g., VSV Matrix protein (GenBank serial number NP041714))], a filovirus viral core protein (e.g., an Ebola VP40 viral protein (e.g., Ebola virus VP40 (GenBank serial number AAN37506))), a Rift Valley Fever virus N protein (e.g., RVFV N Protein (GenBank serial number NP049344)), a coronavirus M, E and NP protein (e.g., GenBank serial number NP040838 for NP protein, NP 040835 for M protein, CAC39303 for E protein of Avian Infections Bronchitis Virus and NP828854 for E protein of the SARS virus)), a bunyavirus N protein (GenBank serial number AAA47114)), an influenza M1 protein, a paramyxovirus M protein, an arenavirus Z protein (e.g., a Lassa Fever Virus Z protein), and combinations thereof. Appropriate surface glycoproteins and/or viral RNA may be included to form the VLP 10.

In general, the viral protein 12 sequence and the corresponding polynucleotide sequence can be found in GenBank and the access numbers can be obtained online at National Center for Biotechnology Information (NCBI). In addition, the sequences identified for the viral proteins 12 above are only illustrative examples of representative viral proteins 12. Furthermore, variants that are substantially homologous to the above referenced viral proteins 12 and viral proteins 12 having conservative substitutions of the above referenced viral proteins 12 can also be incorporated into VLPs 10 of the present disclosure to enhance the immunogenic characteristics of VLPs.

The viral surface envelope glycoprotein 14, or at least at portion of the viral surface envelope glycoprotein 14, is disposed (e.g., expressed) on the surface of the VLP. The viral surface envelope glycoprotein 14 is disposed on the surface of the VLP so that it can interact with target molecules or cells (e.g., the interaction between the HIV surface envelope glycoprotein and the B cell receptor to activate HIV envelope glycoprotein specific antibody producing B cells) to produce immunogenic responses (e.g., antibody production).

The viral surface envelope glycoproteins 14 can include, but are not limited to, a retrovirus glycoprotein (e.g., a human immunodeficiency virus (HIV) envelope glycoprotein (e.g., HIVSF162 envelope glycoprotein (SEQ ID NO: 1, GenBank serial number M65024)), a simian immunodeficiency virus (SIV) envelope glycoprotein (e.g., SIVmac239 envelope glycoprotein (GenBank serial number M33262)), a simian-human immunodeficiency virus (SHIV) envelope glycoprotein (e.g., SHIV-89.6p envelope glycoprotein (GenBank serial number U89134)), a feline immunodeficiency virus (FIV) envelope glycoprotein (e.g., feline immunodeficiency virus envelope glycoprotein (GenBank serial number L00607)), a feline leukemia virus envelope glycoprotein (e.g., feline leukemia virus envelope glycoprotein (GenBank serial number M12500)), a bovine immunodeficiency virus envelope glycoprotein (e.g., bovine immunodeficiency virus envelope glycoprotein (GenBank serial number NC001413)), a bovine leukemia virus envelope glycoprotein (GenBank serial number AF399703), a equine infectious anemia virus envelope glycoprotein (e.g., equine infectious anemia virus envelope glycoprotein (GenBank serial number NC001450)), a human T-cell leukemia virus envelope glycoprotein (e.g., human T-cell leukemia virus envelope glycoprotein (GenBank serial number AF0033817)), and a mouse mammary tumor virus envelope glycoprotein (MMTV)), a bunyavirus glycoprotein (e.g., a Rift Valley Fever virus (RVFV) glycoprotein, (e.g., RVFV envelope glycoprotein (SEQ ID NO: 2, GenBank serial number M11157))), an arenavirus glycoprotein (e.g., a Lassa fever virus glycoprotein (GenBank serial number AF333969))), a filovirus glycoprotein (e.g., an Ebola virus glycoprotein (GenBank serial number NC002549)), a corona virus glycoprotein (GenBank serial number SARS coronavirus spike protein AAP13567), an influenza virus glycoprotein (GenBank serial number V01085)), a paramyxovirus glycoprotein (GenBank serial number NC002728 for Nipah virus F and G proteins), a rhabdovirus glycoprotein (GenBank serial number NP049548)) (e.g., a Vesicular Stomatitis Virus (VSV) glycoprotein), an alphavirus glycoprotein (GenBank serial number AAA48370 for Venezuelan equine encephalomyelitis (VEE)), a flavivirus glycoprotein (GenBank serial number NC001563 for West Nile virus) (e.g., a Hepatitis C Virus glycoprotein), a Herpes Virus glycoprotein (e.g., a cytomegalovirus glycoprotein), and combinations thereof.

In general, the viral surface envelope glycoprotein 14 sequence and the corresponding polynucleotide sequence can be found in GenBank and the access numbers can be obtained online at NCBI. In addition, the sequences identified for the viral surface envelope glycoproteins 14 above are only illustrative examples of representative viral surface envelope glycoproteins 14. Further, variants that are substantially homologous to the above referenced viral surface envelope glycoproteins 14 and viral surface envelope glycoproteins 14 having conservative substitutions of the above referenced viral surface envelope glycoproteins 14 can also be incorporated into VLPs 10 of the present disclosure to enhance the immunogenic characteristics of VLPs.

In one embodiment, the HIV envelope glycoprotein can be modified and/or truncated to improve the immunogenic properties of the VLP. For example, the VLP can be conformationally changed by hydrostatic pressure-induced techniques.

In another embodiment, the HIV envelope glycoprotein can be modified to expose neutralizing epitopes in the HIV envelope glycoprotein by removing obstructing structural features such as, but not limited to, glycosylation sites, the V1 loop, the V2 loop, and the V3 loop. By eliminating these obstructing features, the immunogenic properties of the VLP that includes such modified glycoproteins can be enhanced.

Figure 2:
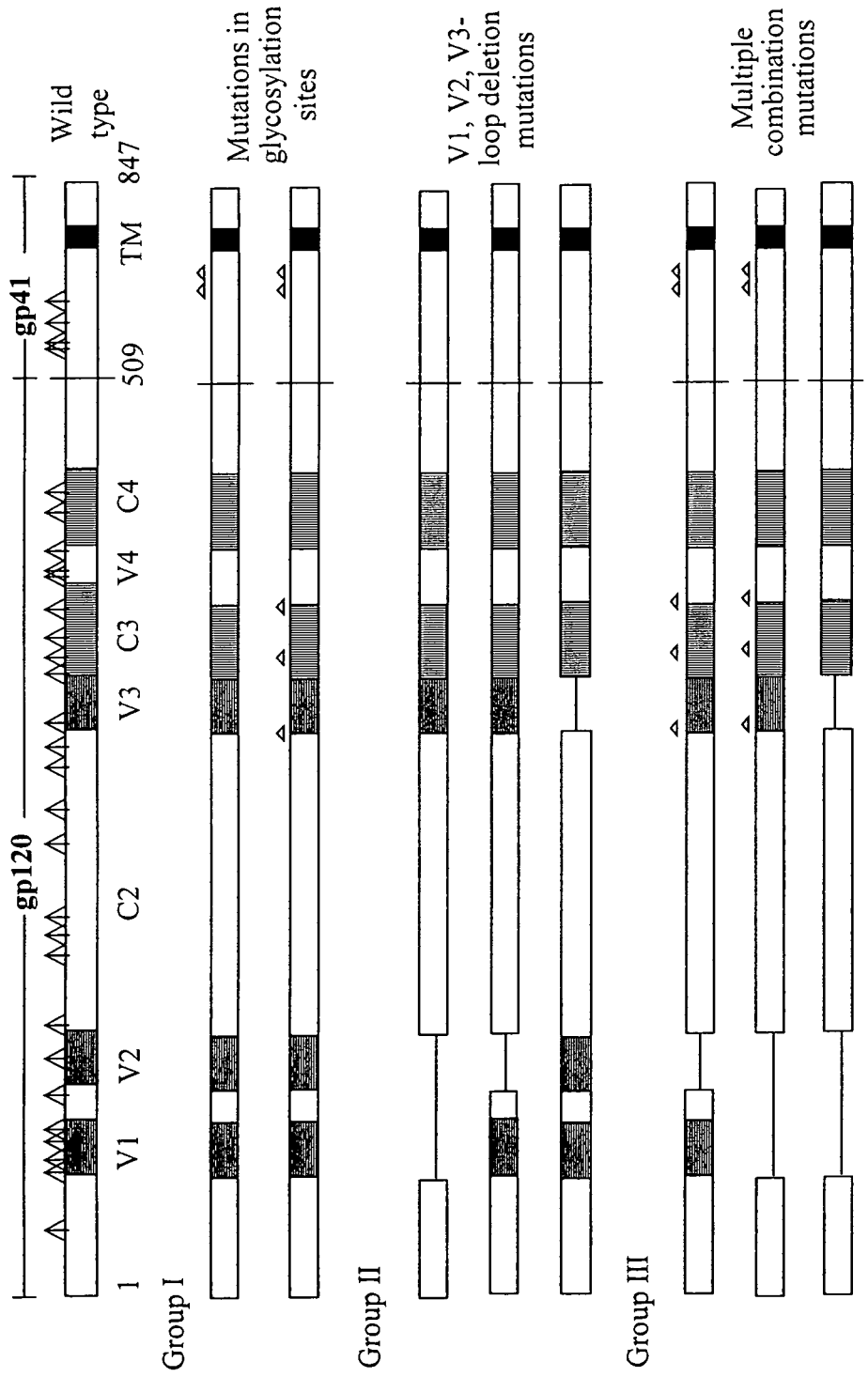
FIG. 2 illustrates some representative structural changes that can be made to a representative viral surface envelope glycoprotein.

FIG. 2 illustrates some representative structural changes that can be made to the HIV 89.6 envelope glycoprotein (GenBank serial number AAA81043, SEQ ID NO: 3). The arrows in FIG. 2 indicate the N-glycosylation motifs in the HIV 89.9 viral surface envelope glycoprotein as well as the V1 (amino acids 128-164 of SEQ ID NO: 3) loop, V2 (amino acids 164-194 of SEQ ID NO: 3) loop, and V3 (amino acids 298-329 of SEQ ID NO: 3) loop domains. Deletions of the loops is shown by removing the corresponding sequence in the HIV 89.6 envelope glycoprotein shown in FIG. 2. When the loop is deleted, a 3 amino acid linker (GAG) is inserted into the loops former position in the sequence. The glycosylation motifs mutated are denoted by triangles. Three glycosylation motif mutations of Asn to Gln in the V3/C3 (amino acids 298-402 of SEQ ID NO: 3) domains are performed on amino acids 301, 341, and 362. In the gp41 domain (amino acids 509-853 of SEQ ID NO: 3), the glycosylation motif mutations are performed on Asn in amino acid position 623 and 635. TM denotes the transmembrane domain (amino acids 681-7033 of SEQ ID NO: 3). In FIG. 2, Group I illustrates the glycosylation motif mutations in gp41, the V1 loop domains, the V2 loop domain, and the V3-C3 loop domain. Group II illustrates variable loop (V1, V2, and/or V3) deletion mutations, while Group III illustrates representative multiple combination mutations.

For example, mutations of glycosylation sites in gp41 can be performed to enhance the immunogenic properties of a VLP incorporating the HIV envelope glycoprotein. Although most of gp41 appears to be completely occluded in the HIV-1 envelope spike, recent studies indicate that regions of gp41 close to the transmembrane domain are accessible to neutralizing antibodies (Abs). Several mAbs (2F5, Z13, 4E10), which neutralize a broad range of primary HIV-1 isolates, are known to bind to the extracellular domain of gp41. However, attempts to elicit antibodies having these properties by immunization with linear peptide epitopes or with other carrier proteins containing peptide epitopes have not been successful (Coeffier et al., Vaccine, 19, 684-693, (2000); Eckhart, L., et al., J. Gen. Viro., 77 (Pt. 9), 2001-2008, (1996); and Liang, X., et al., Vaccine, 17, 2862-2872, (1999)). These studies indicate that the introduction of neutralizing antibodies against gp41 epitopes may be dependent on the native form of trimeric gp120-gp41 and that these epitopes may not be immunodominant, possibly due to the presence of N-glycans. As shown in FIG. 2, the gp41 domain in the HIV-1 envelope glycoprotein contains four conserved glycosylation motifs (#22 (amino acids 608 of SEQ ID NO: 3), #23 (amino acids 613 of SEQ ID NO: 3), #24 (amino acids 622 of SEQ ID NO: 3), and #25 (amino acids 634 of SEQ ID NO: 3), and viruses with single or double mutations in these glycosylation sites replicated in both human and monkey T cell lines (Johnson, W. E., et al., J. Virol., 75, 11426-11436, (2001), which is hereby incorporated by reference herein). Removing the glycosylation motifs #24 (amino acid 622 of SEQ ID NO: 3) and #25 (amino acid 634 of SEQ ID NO: 3) near the neutralizing epitopes may increase the exposure of these epitopes and thus, enhance the induction of neutralizing antibodies against the gp41 domain (numbering glycosylation motifs from the N-terminus of the HIV 89.6 envelope glycoprotein).

It should also be noted, that upon binding of the HIV envelope glycoprotein to its receptor molecules or the shedding of its surface subunit (gp120), its transmembrane subunit (gp41) converts into a six-helix bundle configuration, which is highly immunogenic but only present non-neutralizing epitopes (Kim, P. S., Annual Reviews of Biochemistry, 70, 777-810, (2001)). The use of a peptide containing the amino acid sequence corresponding to a segment of the gp41 (amino acid 629 to 664 of the SEQ ID NO: 1) can effectively block the transition into the undesirable six-helix bundle configuration. Therefore, treatment of VLPs with such a peptide can help to preserve the HIV envelope glycoprotein on the surface of the VLP to retain its native configuration for more efficient exposure of neutralizing epitopes and thus the induction of neutralizing antibodies. Such structural features are common to the envelope glycoproteins of many viral families, including, but not limited to, the envelope glycoproteins of retrovirus, influenza virus, and parainfluenza virus. Thus, such a VLP treatment approach can be applied to a variety of VLP vaccines.

In another example, the V1 loop, the V2 loop, and the V3 loop can be deleted to enhance the immunogenic properties of VLPs. Deletion of individual V1 or V2 loops does not reduce the potential of the virus to replicate in PBMCs or alter the co-receptor binding of the viral surface envelope glycoprotein (Stamatatos, L., et al., Aids Res. Hum. Retroviruses, 14, 1129-1139, (1998)). HIV-1 mutants lacking the V1 and V2 loops in gp120 exhibited increased sensitivity to neutralization by antibodies directed against V3 and a CD4-induced epitope on gp120, and by sera collected from patients infected with clades B, C, D, and F HIV-1 primary isolates (Cao, J., et al., J. Virol., 71, 9808-9812, (1997) and Stamatatos, L., and C. Cheng-Mayer, J. Virol., 72, 7840-7845, (1998)). These studies suggest that the V2 loop or V2 together with the V1 loop shields some important neutralization epitopes with an overall structure that appears to be conserved among different HIV-1 primary isolates. Thus, deleting the V1-V2 loop or V2 loop may expose hidden neutralizing epitopes. Such mutant glycoproteins can be incorporated into VLP vaccines.

The V3 loop of the HIV envelope glycoprotein is highly variable and also constitutes a dominant epitope for the antibody response. Although neutralizing antibodies against this region are frequently detected, they are often strain-specific (Sattentau, Q. J., et al., Virol., 206(1), 713-7, (1995) and D'Souaza, M. P., et al., Aids, 9, 867-874, (1995)). Furthermore, deletion of the V3 loop has also been shown to increase the exposure of epitopes induced by sCD4 binding (Sanders, R. W., et al., J. Virol., 74, 5091-5100, (2000)). Lu et al. (Aids Res. Hum. Retroviruses, 14, 151-155, (1998)) compared antibody induction by gene-gun immunization of rabbits with DNA vectors expressing HIV-1 IIIB Gp160, Gp140, Gp120 and their corresponding V1/V2/V3 triple loop deletion mutants. These results showed that deletion of variable loops induced higher ELISA antibody responses but not neutralizing antibody responses. Such mutant glycoproteins can also be incorporated into VLP vaccines.

In another study, Garrity et al. (J. Immunol., 159, 279-289, (1997)) showed that immunization of guinea pigs using recombinant vaccinia virus followed by protein boosting with mutant viral surface envelope glycoprotein 120, in which glycosylation sites were introduced to mask the immunodominant domain in the V3 loop, was more effective in inducing cross-reactive neutralizing antibodies against a divergent strain of the same subtype. Thus, eliminating the immunodominant epitopes in the V3 loop may enhance induction of cross-reactive antibodies. Furthermore, Kiszka et al. (J. Virol., 76, 4222-4232, (2002)) reported that immunization of mice using DNA vaccines encoding HIV envelope glycoproteins with V3 loop deletions induced broader cellular immune responses to subdominant epitopes and was more effective in conferring protection against challenge with recombinant vaccinia virus expressing heterologous HIV envelope glycoproteins, indicating that deletion of the V3 loop may also be advantageous in inducing broader cellular immune response. Such a deletion mutant glycoprotein can be incorporated into VLP vaccines.

In another embodiment, the RVFV envelope glycoprotein can include, but is not limited to, a RVFV GC envelope glycoprotein (SEQ ID NO: 4) and a RVFV GN envelope glycoprotein (SEQ ID NO: 5). The RVFV GC and GN envelope glycoproteins can be modified to enhance the immunogenic properties of the VLP 10. For example, the RVFV GC and GN envelope glycoproteins can be modified by truncating the cytoplasmic domain for the RVFV GC (amino acids 492-507 of SEQ ID NO: 4) and GN envelope glycoproteins (amino acids 458-527 of SEQ ID NO: 5).

Figure 3:
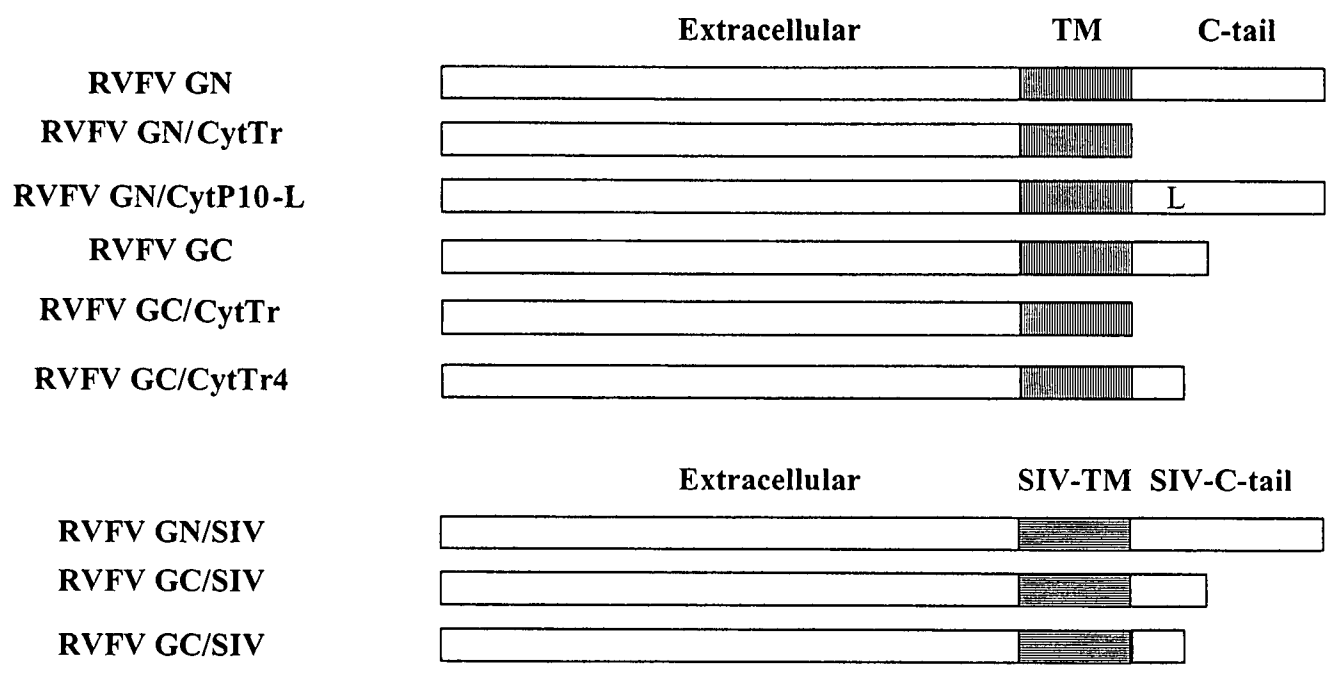

FIG. 3 illustrates some representative structural changes that can be made to the RVFV GN and GC envelope glycoproteins. For example, the RVFV GC and GN envelope glycoproteins can be modified by truncating the cytoplasmic domain for the RVFV GC (amino acids 492-507 of SEQ ID NO: 4) and GN envelope glycoproteins (amino acids 458-527 of SEQ ID NO: 5). In addition, the RVFV GN envelope glycoprotein can mutated by replacing the proline residue (amino acid 537 of SEQ ID NO: 5) from the cytoplasmic domain (conserved between RVFV and PTV GN envelope glycoprotein) with a leucine residue. Such modifications should increase levels of surface expression of the RVFV envelope glycoproteins and therefore increase their incorporation into VLPs. Thus, the effectiveness of the VLPs to elicit immune response against RVFV envelope glycoproteins may be enhanced since the VLPs may contain more RVFV envelope glycoproteins per unit amount.

Furthermore, the RVFV GC and GN envelope glycoproteins can be modified by replacing the transmembrane domain and/or the cytoplasmic tails of the RVFV GC and GN envelope glycoproteins with the transmembrane domain and the cytoplasmic tail of the SIV envelope glycoprotein. Studies on retrovirus assembly have shown that efficient incorporation of viral surface envelope glycoproteins may involve specific interaction between viral Gag proteins and the cytoplasmic domain of the viral surface envelope glycoprotein (Cosson, P., et al., *EMBO J.*, 15, 5783-5788, (1996); Vincent, M. J., et al., *J. Virol.*, 73, 8138-44, (1999); and Wyma, D. J., et al., *J. Virol.*, 74, 9381-7, (2000)). Therefore, replacing the transmembrane domain and cytoplasmic tails of RVFV GN and GC envelope glycoproteins with those of the HIV or SIV envelope glycoprotein (SEQ ID NO: 6) or cytoplasmic tails (SEQ ID NO: 8) may produce chimeric proteins with increased cell surface expression and more efficient incorporation into SIV VLPs.

In previous studies, SIV envelope glycoproteins containing this truncated cytoplasmic domain yielded high levels of cell surface expression and more efficient incorporation into SIV VLPs in comparison to the SIV envelope glycoprotein with a full length cytoplasmic domain of over 150 amino acids (Vzorov, A. and Compans, R. W., *J. Virol.*, 74, 8219-25, (2000)). Furthermore, the cytoplasmic domain of the SIV envelope glycoprotein contains a Tyr-based endocytosis signal, which has been shown to induce rapid endocytosis of the SIV envelope glycoprotein and lead to reduced surface expression (Labranche, C. C., et al., *J. Virol.*, 69, 5217-5227, (1995)). Thus, attaching a truncated SIV envelope glycoprotein cytoplasmic domain to the RVFV envelope glycoproteins that are expressed on cell surface may produce enhanced incorporation into VLPs.

In addition, Tyr residue can be replaced by Cys in the attached SIV cytoplasmic domain sequence (amino acid 16 of SEQ ID NO: 8) to further augment surface expression of designed chimeric proteins. This design for chimeric proteins can be applied to both RVFV GN and GC envelope glycoproteins. Such modifications may increase levels of surface expression of the RVFV envelope glycoproteins and therefore increase their incorporation into VLPs. Thus, the effectiveness of the VLPs to elicit immune response against RVFV envelope glycoproteins may be enhanced, since the VLPs contain more RVFV envelope glycoproteins per unit amount.

The adjuvant molecule 16, or at least a portion of the adjuvant molecule 16, is disposed (e.g., expressed) on the surface of the VLP 10. The adjuvant molecule 16 can interact with other molecules or cells (e.g., mucosal surfaces having sialic acid residues disposed thereon and antigen-presenting cells such as dendritic cells and follicular dendritic cells).

The adjuvant molecule 16 can include, but is not limited to, an influenza hemagglutinin (HA) molecule (GenBank access number J02090), a parainfluenza hemagglutinin-neuraminidase (HN) molecule (GenBank access number z26523 for human parainfluenza virus type 3 HN sequence information), a Venezuelan equine encephalitis (VEE) adjuvant molecule (GenBank access number nc001449), a fms-like tyrosine kinase ligand (Flt3) adjuvant molecule (GenBank access number NM013520), a C3d adjuvant molecule (GenBank access number nm009778 for mouse C3 sequence and access number nm000064 for human C3 sequence), a mannose receptor adjuvant molecule, a CD40 ligand adjuvant molecule (GenBank access number m83312 for mouse CD40), and combinations thereof. The adjuvant molecule 16 can also include membrane anchored forms of a mammalian toll-like receptor (TLR) ligand molecule, a MIP-1α molecule, a RANTES MIP-1β molecule, a GM-CSF molecule, a Flt3 ligand molecule, a CD40 ligand molecule, an IL-2 molecule, an IL-10 molecule, an IL-12 molecule, an IL-15 molecule, an IL-18 molecule, and an IL-21 molecule, and combinations thereof. Examples of membrane-anchored forms of mammalian TLR ligand molecules include, but are not limited to, ligands listed in Akira, S. and Takeda, K. Toll-Like Receptor Signalling. *Nature Reviews/Immunology*, 4: 499-511 (2004), which is incorporated by reference herein. In particular, exemplary TLR ligand molecules include glycoproteins from *Prevotella intermedia*, Respiratory syncytial virus protein F, fibronectin A domain, fibrinogen, flagellin, a measles virus HA protein, and Pam2Cys lipoprotein/lipopeptide (MALP-2).

In general, the adjuvant molecule 16 sequence and the corresponding polynucleotide sequence can be found in GenBank and the access numbers can be obtained online at the NCBI. In addition, the sequences identified for the adjuvant molecules 16 above are only illustrative examples of representative adjuvant molecules 16. Further, variants that are substantially homologous to the above referenced adjuvant molecules 16 and adjuvant molecules 16 having conservative substitutions of the above referenced adjuvant molecules 16 can also be incorporated into VLPs 10 of the present disclosure to enhance the immunogenic characteristics of VLPs.

Mucosal immunity is important for prevention of infection by aerosolized virus because mucosal antibodies can neutralize the virus and/or block virus attachment of the virus to the mucosal cells with secreted antibodies. However, little success has been documented for eliciting strong mucosal immune responses by non-replicating vaccines against viruses other than influenza, which is attributed, at least in part, to the difficulty of targeting the antigens to mucosal sites. In contrast, inactivated influenza virus has been shown to induce strong mucosal immune responses when administered mucosally, which may be the result of the strong binding affinity of the HA adjuvant molecule for sialic acid residues that are abundant at mucosal surfaces. Therefore, the affinity of HA adjuvant molecule for sialic acids may be utilized for targeting VLPs to mucosal surfaces. As discussed in more detail below, HA/SHIV VLPs are highly effective in eliciting strong mucosal immune responses against SHIV antigens when administered intranasally to mice. Thus, incorporating HA adjuvant molecules into VLPs may enhance the immunogenic properties of VLPs.

The following is a non-limiting illustrative example of an embodiment of the present disclosure that is described in more detail in (Guo et. al., "Enhancement of Mucosal Immune Responses by Phenotypically Mixed Influenza HA/SHIV Virus-Like Particles", (2003), 313 (2): 502-513, which is incorporated herein by reference. This example is not intended to limit the scope of any embodiment of the present disclosure, but rather is intended to provide specific experimental conditions and results. Therefore, one skilled in the art would understand that many experimental conditions can be modified, but it is intended that these modifications be within the scope of the various embodiments of this disclosure.

Mucosal immune responses against HIV play an important role in prevention of HIV infection and transmission, as the mucosal surface is the major site for initial HIV infection. Being the first line of defense, mucosal immunity is critical for prevention of infection by neutralizing virus and/or blocking virus attachment with secreted antibodies. However, little success has been documented for eliciting strong mucosal immune responses against HIV, which is attributed at least in part to the difficulty of targeting the antigens to mucosal sites. In contrast, inactivated influenza virus has been shown to induce strong mucosal immune responses when administered mucosally, a likely result of the strong binding affinity of its HA adjuvant molecule for sialic acid residues that are abundant on mucosal surfaces. Therefore, VLPs incorporating the HA adjuvant molecule may be suited to target mucosal surfaces since the HA adjuvant molecule has an affinity for sialic acid.

To enhance mucosal immune responses using SHIV VLPs as a mucosal AIDS vaccine, phenotypically mixed influenza HA/SHIV virus-like particles (HA/SHIV 89.6 VLPs) were produced and used to intranasally immunize C57B/6J mice. Production of phenotypically mixed HA/SHIV 89.6 VLPs, which possess both biologically active HIV envelope glycoproteins and influenza HA adjuvant molecules, may be important in elicitation of enhanced immune responses against HIV envelope proteins. Therefore, baculovirus-derived SHIV 89.6 VLPs and HA/SHIV 89.6 VLPs were produced through co-infection of insect cells with rBV SIV Gag, rBV HIV envelope glycoprotein, both with and without rBV HA adjuvant molecule.

Figure 4:
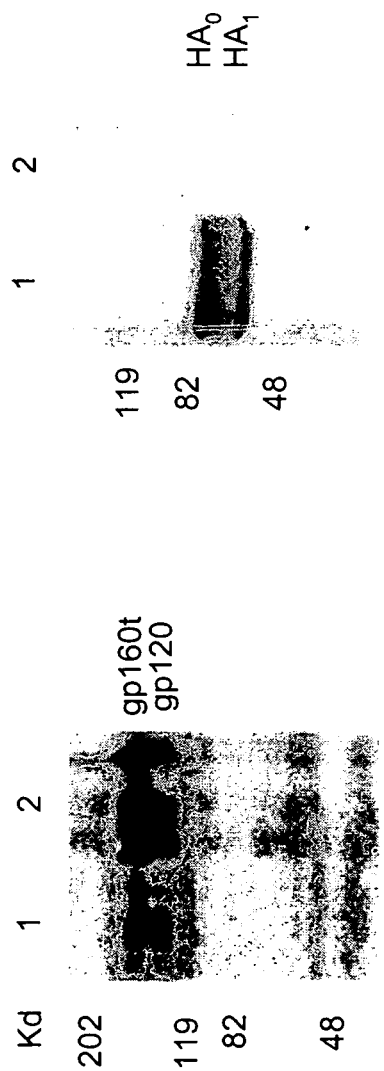
FIGS. 4A and 4B illustrate western blots of representative VLPs incorporating HIV envelope glycoproteins into SHIV VLPs (FIG. 4A) and influenza HA adjuvant molecules into SHIV VLPs (FIG. 4B).

FIGS. 4A and 4B illustrate that both HIV envelope glycoproteins and influenza HA adjuvant molecules can be detected in HA/SHIV 89.6 VLPs by using Western Blot analysis blotting with antibody against HIV envelope glycoproteins (FIG. 4A) or influenza HA adjuvant molecules (FIG. 4B), respectively. Both HIV envelope glycoprotein and influenza HA adjuvant molecule are partially cleaved into their active state gp120 and HA1. In addition, the ability of chimeric VLPs to induce hemagglutination (HA) was examined, a functional property of influenza HA. HA titers of chimeric VLPs were determined by incubating equal volumes of serial two-fold dilutions of HA/SHIV VLPs in PBS-def (PBS deficient in $Mg^{2+}$ and $Ca^{2+}$) with chicken red blood cells (final concentration 0.5%) for 1 hour (h) at room temperature. The HA titer of HA/SHIV 89.6 chimeric VLPs were found to be as high as 1:4000, whereas SHIV 89.6 VLPs showed negative in HA titer.

Figure 5:
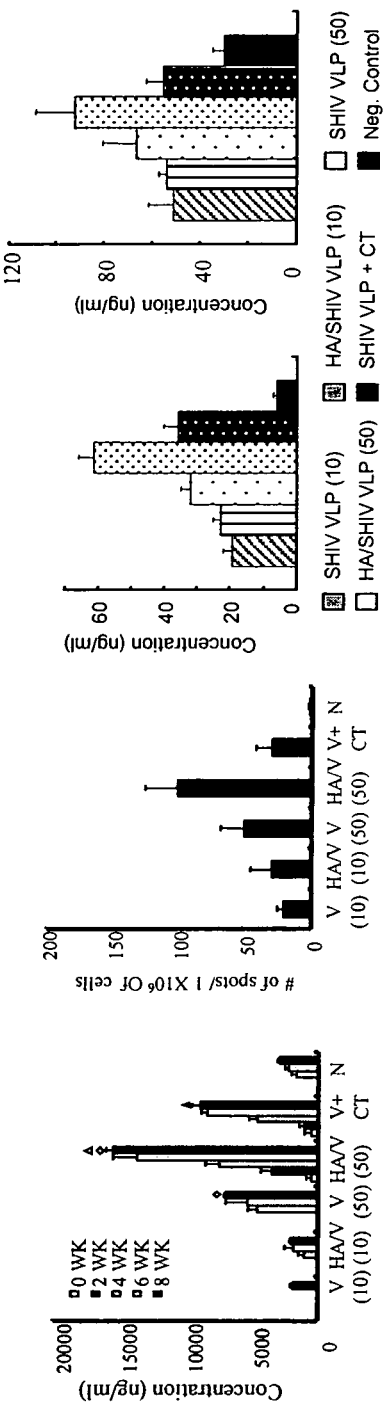

FIGS. 5A through 5B illustrate graphs measuring various characteristics of a number of VLPs that were intranasally introduced into mice. In FIGS. 5A through 5D, "V" represents SHIV VLPs, "HA/V" represents HA/SHIV VLPs, "V+CT" represents SHIV VLPs (10 µg)+cholera toxin (CT) (10 µg), and "N" represents a negative control (PBS). In addition, the number in parentheses indicates the "µg's" of VLPs used for immunization of the mice.

FIG. 5A is a graph measuring serum IgG levels specific to HIV envelope glycoproteins. FIG. 5B is a graph measuring splenocytes producing IFN-γ determined by ELISPOT assay. FIG. 5C is a graph measuring HIV envelope glycoprotein-specific IgA in vaginal wash. FIG. 5D is a graph measuring HIV envelope glycoprotein-specific IgA in fecal extracts.

In particular, systemic and mucosal antibody responses, as well as cytotoxic T cell (CTL) responses, of mice immunized with SHIV 89.6 VLPs or HA/SHIV 89.6 VLPs are shown in FIGS. 5A through 5D. Intranasal immunizations were given with VLPs either with or without addition of CT. The level of serum IgG production to HIV envelope glycoprotein was found to be highest in the group immunized with phenotypically mixed HA/SHIV 89.6 VLPs. Similarly, mucosal IgA production was also found to be enhanced in the group immunized with HA/SHIV VLP mucosally. Analysis of the IgG1/IgG2a ratio indicated that a Th1-oriented immune response resulted from these VLPs immunizations. HA/SHIV VLP-immunized mice also showed significantly higher CTL responses than those observed in SHIV VLP-immunized mice. Furthermore, a MHC class I restricted T cell activation ELISPOT assay showed elevated IFN-γ, IL-2, and IL-12 production in HA/SHIV VLP-immunized mice, indicating that phenotypically mixed HA/SHIV VLPs can enhance both humoral and cellular immune responses at multiple mucosal sites. Thus, a heterologous adjuvant molecule, the HA adjuvant molecule, can be coexpressed with retrovirus proteins in infected cells resulting in its efficient incorporation into retroviral VLPs in a biologically active form. In addition, the resultant VLPs exhibit enhanced immunogenicity, especially when delivered by a mucosal route. These results demonstrate the feasibility of construction of a range of VLPs containing heterologous surface molecules for possible use as improved vaccine antigens. Therefore, chimeric HA-containing VLPs may be used for the mucosal immunization against HIV.

The possibility of pre-existing immunity to the influenza HA protein is a factor that should be considered in the evaluation of HA-VLP vaccines. However, it is uncertain that the existence of such preexisting immunity would negatively impact the immune responses to the VLPs (in marked contrast to immunization using replicating vectors). It is in fact possible that preexisting antibodies would lead to production of immune complexes would enhance targeting of VLPs to follicular dendritic cells and thus result in stimulation of B cell responses.

Nevertheless, alternative approaches can be applied for mucosal targeting of VLPs. One possibility is to utilize influenza HA adjuvant molecules from other influenza virus species to which there is no preexisting immunity in the human population. There are about 15 such non-cross reactive serotypes of HA adjuvant molecules, which have been identified, which are antigenically non-overlapping based on tests with polyclonal immune sera. The 15 non-cross reactive serotypes of HA viruses and their replication are described in the following publications: Lamb, R. A. and Krug, R. M., *Orthomyxoviridae*, (1996) and Fields, B. N., et. al., Editors, *Field's Virology*, Lippincott-Raven Publishers, Philadelphia, Pa., 1353-1395, (1996). Thus, VLPs can be produced containing one or more of these alternative HA adjuvant molecule subtypes, therefore avoiding a possible affect of preexisting anti-HA immunity on induction of immune responses against VLP antigens. It should be noted that some influenza HA adjuvant molecules from other species may bind preferentially to sialic acid linkages not found on human cells. This property, however, can be modified by mutation of specific HA amino acids (Vines, A., et al., *J. Virol.*, 72, 7626-7631, (1998)).

An alternative approach to using HA adjuvant molecules is the production of VLPs containing parainfluenza virus HN adjuvant molecules. Like HA adjuvant molecules, the HN adjuvant molecules attach specifically to the sialic acid residues at mucosal surfaces. Therefore, chimeric VLPs containing HN adjuvant molecules should have similar mucosal targeting properties as the HA adjuvant molecules. However, immune responses to the proteins of human parainfluenza viruses are of relatively short duration, and reinfections with the same viral serotypes are known to occur (Glezen, W. P., et al., *J. Infect. Dis.*, 150, 851-857, (1984)). Thus, as compared with HA, it is less likely that preexisting immunity to the HN adjuvant molecules of a parainfluenza virus would affect mucosal delivery of a VLP vaccine.

HN-VLPs may be easier to produce in modified vaccinia Ankara expression systems rather than HA-VLPs. This is because the release of HA chimeric VLPs from mammalian cells would require addition of exogenous neuraminidase (Bosch, V., et al., *J. Gen. Virol.*, 82, 2485-2494, (2001)) since sialic acid would be added to the envelope glycoproteins as a terminal sugar and lead to aggregation of VLPs at the cell surface (which does not occur in the insect cell-produced VLPs). In contrast, HN carries its own neuraminidase. Studies of viral pseudotypes have shown that the glycoproteins of parainfluenza viruses including the HN adjuvant molecule can be assembled into virions of retroviruses, indicating that this type II membrane protein can be incorporated into VLPs (Spiegel, M. et al., *J. Virol.*, 72, 5296-5302, (1998)). Thus, incorporating HN adjuvant molecules into VLPs may enhance the immunogenic properties of VLPs.

Antigen presenting cells can be targeted by VLPs by including one or more of the following adjuvant molecules on the surface of the VLP: the VEE adjuvant molecule, the Flt3 ligand molecule, the mannose adjuvant molecule, the CD40 adjuvant molecule, and the Cd3 ligand molecule. In particular, the VEE adjuvant molecule, the Flt3 adjuvant molecule, the mannose receptor adjuvant molecule, and the CD40 adjuvant molecule can be used to target dendritic cells, while the Cd3 ligand molecule can be used to target follicular dendritic cells.

Dendritic cells (DCs) are very efficient antigen presenting cells involved in priming native CD4 and CD8 T cells, thus inducing primary immune responses and permitting establishment of immunological memory (Inaba, K., et al., *J. Exp. Med.*, 166:182-194, (1987) and Inaba, K., et al., *J. Exp. Med.*, 172:631-640, (1990)). Antigens taken up by DCs are expressed at the cell surface in the form of peptides associated with MHC class II, which stimulates CD4 Th cells. For induction of CD8 T cells, MHC class 1 associated peptides are derived from endogenously synthesized proteins as well as from some exogenous antigens (e.g., infectious agents, dying cells, proteins associated with inert particles, and immune complexes) by DC endocytosis (Heath, W. R. and F. R. Carbone, *Curr. Opin. Immunol.*, 11:314-318, (1999); Reimann, J. and R. Schirmbeck, *Immunol. Rev.*, 172; 131-152, (1999); Regnault, A., et al., *J. Exp. Med.*, 189:371-380, (1999); and Machy, P., et al., *Eur. J. Immunol.*, 30:848-857, (2000)). DCs harboring immune complexes also stimulate naïve B cells (Wykes, M., *J. Immunol.*, 161, 1313-1319, (1998) and Dubois, B., et al., *Biol.*, 70, 633-641, (2001)). The highly developed Ag-presenting capacity of DCs has led to their study of cellular vaccine adjuvants for the immunotherapy of cancer (Schuler, G. and R. M. Steinman, *J. Exp. Med.*, 1986: 1183-1187, (1997) and Baggers, J., et al., *J. Clin. Oncol.*, 18:3879-3882, (2000)). HIV and SIV virions interact with DCs via DC-SIGN and/or CD4 receptors; however, this interaction appears to preferentially result in infection of the DCs as well as transmission to other target cells rather than potentiation of an immune response (Geijtenbeek, T. B., et al., *Cell*, 100: 587-597, (2000) and Geijtenbeek, T. B., et al., *Immunol. Lett.* 79:101-107, (2001)). On the other hand, inert particulate antigens like VLPs are very attractive target for antigen presenting cells, particularly DCs (Bachmann, M. F., et al., *Eur. J. Immunol.*, 26:2595-2600, (1996); Ruedl, C., et al., *Eur. J. Immunol.*, 32:818-825, (2002) and Da Silva, D. M., et al., *Int. Immunol.*, 13:633-641, (2001)). Therefore, the interaction of VLPs with DCs may result in potentiating DCs to initiate T cell activation.

The possible advantage of targeting vaccine antigens to DCs is indicated by the extremely small number of DCs in peripheral tissues and in blood, where DCs represent less than 1% of total cell number. Flt3 ligand (FL) adjuvant molecule (GenBank access number NM013520) is a hematopoietic growth factor that has the unique ability to expand the number of both CD8α– and CD8α+ DC subsets (Lyman, S. D., et al., *Cell*, 75:1157-1167, (1993); Maraskovsky, E, et al., *J. Exp. Med.*, 184:1953-1962, (1996); Maraskovsky, E, et al., *Blood*, 96:878-884, (2000) and Pulendran, B., et al., *J. Immunol.*, 159:222-2231, (1997)). Such expansion of DCs in mice resulted in dramatic increases in Ag-specific B and T cell responses (Pulendran, B., et al., *J. Exp. Med.*, 188, 2075-2082, (1998)), enhanced T-cell mediated immune responses (Pisarev et al., *Int J Immunopharmacol*, 11, 865-76, (2000)), and protective immunity to *Listeria monocytogenes* (Gregory, S. H., et al., *Cytokine*, 13:202-208, (2001)). It is suggested that FL treatment increases the capacity of DCs as antigen presenting cells by up-regulating MHC and costimulatory molecules (CD40, CD86), and by inducing production of cytokines (IFN-γ, IL-2, IL-12 or IL-4) (Pulendran, B., et al., *J. Exp. Med.*, 188, 2075-2082, (1998) and Pulendran, B., et al., *Proc. Natl. Acad. Sci., U.S.A.* 96, 1036-1041, (1999)). Therefore, incorporation of FL adjuvant molecules into VLPs may enhance the immunogenic properties of the VLPs.

The VLP can be produced to include the FL adjuvant molecule by PCR-amplifying and cloning the whole FL gene including the signal sequence and transmembrane (TM) domain into rBV transfer vector pc/pS1. To construct a rBV expressing FL, Sf9 insect cells can be co-transfected with Baculogold DNA (available from PharMingen, Inc.) and the pc/pS1 transfer vector containing the FL gene.

The incorporation of the FL adjuvant molecule into VLPs can be enhanced by modifying the FL adjuvant molecule. In particular, the extracellular coding domain of the FL gene (from the end of signal peptide to the start of the TM segment) (SEQ ID NO: 7) can be fused to the N-terminus of the SIV Env glycoprotein-41 TM domain (SEQ ID NO: 6) and the tPA signal peptide can be fused to the N-terminus of the FL-chimeric protein (SEQ ID NO: 9). An alternative approach is to produce a glycosyl-phosphatidylinositol (GPI)-anchored form the FL adjuvant molecule (designated as FL-GPD using a pcDNA3-GPt cassette (GenBank access number x52645), which was previously used to produce GM-CSF in an active membrane-bound form (Poloso, N. J., et al., *Mol. Immunol.*, 38:803-816, (2002)). GPI-anchored proteins preferentially associate with lipid rafts, which are used as sites for virus assembly (Nguyen, D. H. and J. E. Hildreth; *J. Virol.*, 74:3265-3272, (2000)). These chimeric FL constructs can be cloned into pc/pS1 and used to produce rBVs expressing FL fusion proteins.

VEE is a member of the family Togaviridae and is typically transmitted by mosquitoes to humans or other animals, in which it causes fever and encephalitis. Following inoculation into the footpad of mice, the virus was observed to be rapidly transported to the draining lymph nodes. Recent studies have shown that dendritic cells in the lymph nodes are the primary target of VEE infection, and VEE replicon particles were observed to be localized in Langerhans cells, dendritic cells of the skin, following subcutaneous inoculation (Macdonald, G. H., and Johnston, R. E., *J. Virol.*, 74(2), 914-22, (2000)). These investigators also showed that the targeting of VEE adjuvant molecules to DCs was dependent upon the specific amino acid sequence of the viral envelope glycoprotein E2. Therefore, VLPs incorporating VEE adjuvant molecules may be used to target dendritic cells.

Dendritic cells use the mannose receptor (MR) as the major receptor for endocytosis of antigens (Sallusto, F., et al., *J. Exp. Med.*, 192(2), 389-400, (1995)). This receptor is a 175 kD protein containing eight carbohydrate recognition domains with high affinity for mannose-rich glycoproteins (Stahl, P. D., *Curr Opin Immunol.*, 4(1), 49-52, (1992) and Ezekowitz, R. A., et al., *J. Exp. Med.*, 172(6), 1785-94, (1990)). Following endocytosis, the MR releases its ligand at low pH and it recycles to the cell surface, thus having the capacity to interact with ligands in multiple rounds (Stahl, P., et al.; *Cell,* 19(1), 207-15, (1980)). It has been suggested that the MR may provide a mechanism for distinguishing self from non-self antigens on the basis of glycosylation patterns since, in higher eukaryotes, mannose residues are usually buried within the carbohydrate moieties of envelope glycoproteins and therefore not available for binding to MR (Sallusto, F., et al., *J. Exp. Med.* 192(2), 389-400, (1995)). Thus, it may be possible to target VLPs to dendritic cells on the basis of distinct oligosaccharide profiles.

Once dendritic cells take up antigens, immature dendritic cells need to differentiate into professional antigen presenting cells in response to maturation signals. As dendritic cells mature, expression of co-stimulatory molecules and MHC-peptide complexes increase and cytokines are produced (Banchereau, J. & I Steinman, R. M., *Nature,* 392, 245-52, (1998) and Pierre, P., Turley, et al., *Nature,* 388, 787-92, (1997)). Interaction between CD40 expressed on antigen presenting cells including dendritic cells and CD40L on activated Th cells is important for T cell dependent B cell activation and isotype switching (Rousset, F., et al., *J. Exp. Med.,* 173,705-10, (1991)). CD40 ligation with a cell line expressing CD40L activates Langerhans cell-derived dendritic cells, and induces high level expression of MHC II and accessory molecules such as CD80 and CD86 (Caux, C., et al., *J. Exp. Med.,* 180, 1263-1272, (1994)). Cross-linking CD40 with anti-CD40 antibodies play a role in ablating the tolerogenic potential of lymphoid dendritic cells (Grohmann U., et al., *J. Immunol.* 166, 277-83, (2001)). It is also shown that signaling through CD40 on the antigen presenting cells can replace the requirement for "help" from CD4 Th cells in inducing CTL activities (Bennett, S. R., et al., *Nature,* 393, 478-480, 1993 and Schoenberger, S. P., et al., *Nature,* 393, 480-483, (1998)). In anti-tumor pre-clinical model studies, it is indicated that the main mediator for dendritic cell activation is CD40 receptor engagement (Ribas, A., et al., *Cancer Res.*, 61, 8787-8793, (2001) and Ridge, J. P., et al., *Nature,* 393, 474-478, (1998)). These studies suggest that CD40L seem to provide important maturation signals for dendritic cells. Therefore, VLPs incorporating CD40L adjuvant molecules may be used to target dendritic cells.

Follicular dendritic cells (FDCs) play an important role in germinal centers, where antibody-forming cells are generated. Recent studies have indicated that FDCs play an important co-stimulatory role in the enhancement of antibody responses (Qin, D., et al. *J. Immunol.,* 161, 4549-4554, (1998); Fearon, D. T. and Carroll, M. C.; *Annu. Rev. Immunol.,* 18, 393-422, (2000); Fakher, M., et al., *Eur. J. Immunol.,* 31, 176-185, (2001) and Tew, J. G., et al., *Trends Immunol.,* 22, 361-367, (2001)). During HIV infection, immune complexes containing virions are found in association with FDCs (Hlavacek, W. S., et al.; *Philos. Trans. R. Soc. Lond B Biol. Sci.,* 355, 1051-1058, (2000); Rosenberg, Y. J., et al., *Dev. Immunol.,* 6, 61-70, (1998); Smith, B. A. et al.; *J. Immunol.,* 166, 690-696, (2001)), and such complexes could play a significant role in effective antigen presentation to B cells for induction of neutralizing antibody as observed during HIV infection in vivo. Because of their close similarity to virions, VLPs may mimic such immune complexes much more closely than soluble antigens.

The FDCs interact with components of the complement system including C3d, and it was recently demonstrated that recombinant proteins containing a segment of the C3d adjuvant molecule fused (amino acids 1024 to 1320 of SEQ ID NO: 11) to an antigen resulted in a striking increase in the efficiency of the antibody response (Dempsey, P. W., et al., *Science,* 271, 348-350, (1996)). Complement is a plasma protein system of innate immunity that is activated by microorganisms in the absence of antibody (Fearon, D. T. and Austen, K. F., *N. Engl. J. Med.,* 303, 259-263, (1980)). Upon activation, C3d fragment binds to its receptor, CR2 (CD21) which is primarily expressed on B cells and FDCs (Fearon, D. T. and Carter, R. H.; *Annu. Rev. Immunol.,* 13:17-149, (1995)). The presence of C3d adjuvant molecules on the surfaces of the VLPs may result in their enhanced interaction with FDCs and B cells, and thus stimulation of the antibody responses to viral surface envelope glycoproteins contained in the VLP structure.

Because of the relatively large size of the C3d adjuvant molecule fragment, which is about 300 amino acids in length, two factors may affect its function: 1) its proper exposure for interaction with CR2 on FDC; and 2) its potential interference with the proper folding of the protein antigen. Two alternative approaches can be used to incorporate the C3d fragment into VLPs in order to elucidate antibody responses against viral surface glycoproteins incorporated into the VLPs.

First, the C3d adjuvant molecule fragment (amino acids 1024 to 1320 of SEQ ID NO: 11) can be fused to the N-terminus of the selected viral surface envelope glycoprotein and a signal peptide can be introduced at the N-terminus of the viral surface envelope glycoprotein. Second, a signal peptide, such as the tPA signal peptide (SEQ ID NO: 9), can be fused to the N-terminus of the C3d adjuvant molecule and a membrane anchoring sequence (TM domain of viral glycoproteins, example SIV envelope TM (SEQ ID NO: 6), or the GPI-anchoring sequence (GenBank access number x52645, SEQ ID NO: 10)) can be fused to the C-terminus of the C3d adjuvant molecule.

VLPs can be produced by in vitro cell culture expression systems such as, but not limited to, recombinant baculovirus expression system (BEVS) (Yamshchikov, G. V., Ritter, G. D., Vey, M., and Compans, R. W. *Virology,* 214, 50-58, (1995). Assembly of SIV virus-like particles containing envelope proteins can be performed using expression systems, such as, but not limited to, a baculovirus expression system (Yamshchikov, G. V., Ritter, G. D., Vey, M., and Compans, R. W., *Virology,* 214, 50-58, (1995)), recombinant poxvirus expression system (MVA) (Wyatt L S, et. al., *Vaccine,* 15, 1451-8, (1996)), recombinant VSV, recombinant adenovirus, and recombinant DNA expression vectors. Preferably, the VLPs are produced using recombinant BEVS and recombinant poxvirus expression systems.

In general, VLPs can be produced by simultaneously introducing into a cell a viral protein expression vector, a viral surface envelope glycoprotein expression vector, and/or an adjuvant molecule expression vector. The expressed viral core protein self-assembles into a VLP that incorporates the viral surface envelope glycoprotein and/or the adjuvant molecule. The viral surface envelope glycoprotein and/or the adjuvant molecule are expressed on the VLP surface. Thereafter, the cell produces the VLP (e.g., Vero cells, chimeric and/or phenotypically mixed VLPs). The cells can include, but are not limited to, insect cells (e.g., *spodopera frugiperda* Sf9 cells and Sf21 cells) and mammalian cells (e.g., EL4 cells and HeLa cells). The elements for expressing the viral core protein, viral surface envelope glycoprotein, and adjuvant molecule can also be included together in a single expression vector, or can be included in two or more expression vectors.

In general, the viral protein expression vector can be produced by operably linking a coding sequence for a viral protein of a virus to an appropriate promoter (e.g., an early promoter, late promoter, or hybrid late/very late promoter). The viral protein expression vector can also be modified to form a viral protein expression construct. In addition, the viral surface envelope glycoprotein expression vector can be produced by operably linking a coding sequence for a viral surface envelope glycoprotein of a virus to an appropriate promoter (e.g., early promoter, late promoter, or hybrid late/very late promoter). The viral surface envelope glycoprotein expression vector can be modified to form a viral surface envelope glycoprotein expression construct. Similarly, the adjuvant molecule expression vector can be produced by operably linking a coding sequence for an adjuvant molecule to an appropriate promoter (e.g., early promoter, late promoter, or hybrid late/very late promoter). The adjuvant molecule expression vector can be modified to form an adjuvant molecule expression construct.

In other embodiments, polynucleotide sequences encoding for a viral core protein, at least one viral surface envelope glycoprotein, and at least one adjuvant molecule can be included in a single expression vector, or in two or more expression vectors. The one or more expression vectors can be introduced into a host cell, the proteins can be expressed in the cell, whereby the cell forms the VLP. In embodiments, each of the polynucleotide sequences encoding for the viral core protein, the viral surface envelope glycoprotein, and the adjuvant molecule is operably linked to an appropriate promoter (e.g., a baculovirus promoter, a recombinant Modified Vaccinia Ankara (MVA) promoter, a CMV promoter, an EF promoter, an adenovirus promoter, a recombinant VSV promoter, a recombinant adenovirus promoter, a recombinant alphavirus promoter, and a recombinant DNA expression vector). Appropriate promoters include, but are not limited to, a constitutive or inducible promoter; an early, late or hybrid late/very late promoter.

Additional embodiments also include methods of immunizing a host by expressing a viral core protein, at least one viral surface envelope surface glycoprotein, and at least one adjuvant molecule in one or more host cells (e.g., via use of one or more expression vectors). The viral core protein, at least one viral surface envelope glycoprotein, and at least one adjuvant molecule thus expressed by the host cell(s), assemble to form a VLP. The VLP elicits an immune response from the host, thereby providing future protection from infection by a pathogen corresponding to the proteins expressed by the VLP.

In the case of where the adjuvant molecule is mannose, the adjuvant molecular expression construct is not needed because the mannose molecules can be chemically added to VLPs after the VLPs are produced.

The term "host" includes humans, mammals (e.g., cats, dogs, horses, and cattle), and other living species that are in need of treatment. Hosts that are "predisposed to" condition(s) can be defined as hosts that do not exhibit overt symptoms of one or more of these conditions but that are genetically, physiologically, or otherwise at risk of developing one or more of these conditions.

The term "treat", "treating", and "treatment" are an approach for obtaining beneficial or desired clinical results. For purposes of embodiments of this disclosure, beneficial or desired clinical results include, but are not limited to, alleviation of symptoms, diminishment of extent of disease, stabilization (e.g., not worsening) of disease, preventing spread of disease, delaying or slowing of disease progression, amelioration or palliation of the disease state, and remission (partial or total) whether detectable or undetectable. In addition, "treat", "treating", and "treatment" can also mean prolonging survival as compared to expected survival if not receiving treatment.

The term "condition" and "conditions" denote a state of health that can be related to infection by a virus. The infections that are discussed herein are to be included as conditions that can be treated by embodiments of the present disclosure.

"Polypeptide" refers to peptides, proteins, glycoproteins, and the like, of the present disclosure comprising two or more amino acids joined to each other by peptide bonds or modified peptide bonds, (e.g., peptide isosteres). "Polypeptide" refers to both short chains, commonly referred to as peptides, oligopeptides, or oligomers, and to longer chains, generally referred to as proteins. "Polypeptides" may contain amino acids other than the 20 gene-encoded amino acids. "Polypeptides" include amino acid sequences modified either by natural processes, such as post-translational processing, or by chemical modification techniques, which are well known in the art. Such modifications are described in basic texts and in more detailed monographs, as well as in a voluminous research literature.

Modifications may occur anywhere in the polypeptides of the present disclosure, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched, and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (Proteins-Structure and Molecular Properties, 2nd Ed., T. E. Creighton, W.H. Freeman and Company, New York, 1993; Wold, F., Post-translational Protein Modifications: Perspectives and Prospects, pgs. 1-12 in Post-translational Covalent Modification of Proteins, B. C. Johnson, Ed., Academic Press, New York, 1983; Seifter, et al., *Meth. Enzymol.*, 182: 626-646, (1990), and Rattan, et al., *Ann NY Acad. Sci.*, 663: 48-62, (1992)).

"Variant" refers to polypeptides of the present disclosure that differ from a reference polynucleotide or polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also includes the degree of sequence relatedness between polypeptide or polynucleotide sequences, as the case may be, as determined by the match between strings of such sequences. "Identity" and "similarity" can be readily calculated by known methods, including, but not limited to, those described in *Computational Molecular Biology*, Lesk, A. M., Ed., Oxford University Press, New York, (1988); *Biocomputing: Informatics and Genome Projects*, Smith, D. W., Ed., Academic Press, New York, (1993); *Computer Analysis of Sequence Data, Part I*, Griffin, A. M., and Griffin, H. G., Eds., Humana Press, New Jersey, (1994); *Sequence Analysis in Molecular Biology*, von Heinje, G., Academic Press, 1987; and *Sequence Analysis Primer*, Gribskov, M. and Devereux, J., Eds., M Stockton Press, New York, (1991); and Carillo, H., and Lipman, D., *SIAM J Applied Math.*, 48, 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (*J. Mol. Biol.*, 48, 443-453, (1970)) algorithm (e.g., NBLAST, and XBLAST). The default parameters are used to determine the identity for the polynucleotides and polypeptides of the present disclosure.

By way of example, the polypeptide sequences of the present disclosure may be identical to one or more of the reference sequences described above, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "substantially homologous" is used herein to denote polypeptides of the present disclosure having about 50%, about 60%, about 70%, about 80%, about 90%, and preferably about 95% sequence identity to the sequences discussed above. Percent sequence identity is determined by conventional methods as discussed above.

In general, homologous polypeptides of the present disclosure are characterized as having one or more amino acid substitutions, deletions, and/or additions.

In addition, embodiments of the present disclosure include polynucleotides that encode polypeptides having one or more "conservative amino acid substitutions" of the wild type sequence as well as polynucleotides that encode polypeptides that are "functional variants" of the wild type sequence. "Functional variants" includes polypeptides (and polynucleotides encoding such polypeptides) that may have substations, deletions or insertions of more than one amino acid (e.g., substitution of an entire peptide domain or fragment thereof, such as a signal peptide domain, transmembrane domain or cytoplasmic tail domain, of a protein or peptide) but which retains the essential functions of the original, or wild type, protein or peptide.

"Conservative amino acid substitutions" can be based upon the chemical properties of the amino acids. Variants can be obtained that contain one or more amino acid substitutions of the sequences discussed above, in which an alkyl amino acid is substituted for an alkyl amino acid in a polypeptide, an aromatic amino acid is substituted for an aromatic amino acid in a polypeptide, a sulfur-containing amino acid is substituted for a sulfur-containing amino acid in a polypeptide, a hydroxy-containing amino acid is substituted for a hydroxy-containing amino acid in a polypeptide, an acidic amino acid is substituted for an acidic amino acid in a polypeptide, a basic amino acid is substituted for a basic amino acid in a polypeptide, or a dibasic monocarboxylic amino acid is substituted for a dibasic monocarboxylic amino acid in a polypeptide.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. Other conservative amino acid substitutions include amino acids having characteristics such as a basic pH (arginine, lysine, and histidine), an acidic pH (glutamic acid and aspartic acid), polar (glutamine and asparagine), hydrophobic (leucine, isoleucine, and valine), aromatic (phenylalanine, tryptophan, and tyrosine), and small (glycine, alanine, serine, threonine, and methionine).

Polypeptides having amino acid variants can also comprise non-naturally occurring amino acid residues. Non-naturally occurring amino acids include, without limitation, trans-3-methylproline, 2-4-methanoproline, cis-4-hydroxyproline, trans-4-hydroxyproline, N-methyl-glycine, allo-threonine, methylthreonine, hydroxyethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations are carried out in a cell-free system comprising an *E. coli* S30 extract and commercially available enzymes and other reagents. Proteins are purified by chromatography. (Robertson, et al., *J. Am. Chem. Soc.*, 113, 2722, (1991); Ellman, et al., *Methods Enzymol.*, 202, 301, (1991); Chung, et al., *Science,* 259, 806-9, (1993); and Chung, et al., *Proc. Natl. Acad. Sci. USA,* 90, 10145-9, (1993)).

In a second method, translation is carried out in *Xenopus* oocytes by microinjection of mutated mRNA and chemically aminoacylated suppressor tRNAs (Turcatti, et al., *J. Biol. Chem.,* 271, 19991-8, (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.,* 33, 7470-6, (1994)). Naturally occurring amino acid residues can be converted to non-naturally occurring species by in vitro chemical modification. Chemical modification can be combined with site-directed mutagenesis to further expand the range of substitutions (Wynn, et al., *Protein Sci.,* 2, 395-403, (1993)).

A "chimeric" VLP, as used herein, can be defined as a VLP having at least one viral surface envelope glycoprotein incorporated into the VLP, wherein the viral core protein and at least one viral surface envelope glycoprotein are from different viruses. A chimeric VLP, as used herein, may include additional viral surface envelope glycoproteins that are from the same or different virus as the viral core protein, so long as at least one is different.

A "phenotypically mixed" VLP, as used herein, can be defined as a VLP having at least two different surface molecules (e.g., surface envelope glycoproteins and/or adjuvant molecules) incorporated into the VLP. A phenotypically mixed VLP, as used herein, may include additional surface molecules that are from the same or different source as the viral core protein, so long as at least one is different.

"Expressed", as used herein, can be defined as being a molecule disposed, or a portion of the molecule disposed, upon the surface of the VLP.

An "expression construct" is an expression vector containing a coding sequence for a recombinant protein.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under-expressed or not expressed at all.

The term "operably linked" refers to the arrangement of various nucleotide sequences relative to each other such that the elements are functionally connected to and are able to interact with each other. Such elements may include, without limitation, one or more promoters, enhancers, polyadenylation sequences, and transgenes. The nucleotide sequence elements, when properly oriented, or operably linked, act together to modulate the activity of one another, and ultimately may affect the level of expression of the transgene. The position of each element relative to other elements may be expressed in terms of the 5' terminus and the 3' terminus of each element, and the distance between any particular elements may be referenced by the number of intervening nucleotides, or base pairs, between the elements.

A "vector" is a genetic unit (or replicon) to which or into which other DNA segments can be incorporated to effect replication, and optionally, expression of the attached segment. Examples include, but are not limited to, plasmids, cosmids, viruses, chromosomes and minichromosomes. Exemplary expression vectors include, but are not limited to, baculovirus vectors, modified vaccinia Ankara (MVA) vectors, plasmid DNA vectors, recombinant poxvirus vectors, bacterial vectors, recombinant baculovirus expression systems (BEVS), recombinant rhabdovirus vectors, recombinant alphavirus vectors, recombinant adenovirus expression systems, recombinant DNA expression vectors, and combinations thereof.

A "coding sequence" is a nucleotide sequence that is transcribed into mRNA and translated into a protein, in vivo or in vitro.

"Regulatory sequences" are nucleotide sequences, which control transcription and/or translation of the coding sequences, which they flank.

"Processing sites" are described in terms of nucleotide or amino acid sequences (in context of a coding sequence or a polypeptide). A processing site in a polypeptide or nascent peptide is where proteolytic cleavage occurs, where glycosylation is incorporated or where lipid groups (such as myristoylation) occurs. Proteolytic processing sites are where proteases act.

"Virus-like particles" (VLPs) are membrane-surrounded viral core structures having viral envelope proteins expressed on the VLP surface. In addition, adjuvant molecules can be expressed on the VLP. Further, viral core proteins are located within the membrane of the VLP. Additional components of VLPs, as known in the art, can be included within or disposed on the VLP. VLPs do not contain intact viral nucleic acids, and they are non-infectious. Desirably, there is sufficient viral surface envelope glycoprotein and/or adjuvant molecules expressed, at least in part, on the surface of the VLP so that when a VLP preparation is formulated into an immunogenic composition and administered to an animal or human, an immune response (cell-mediated or humoral) is raised.

A "truncated" viral surface envelope glycoprotein is one having less than a full length protein (e.g., a portion of the cytoplasmic domain has been removed), which retains surface antigenic determinants against which an immune response is generated, preferably a protective immune response, and it retains sufficient envelope sequence for proper membrane insertion. The skilled artisan can produce truncated virus envelope proteins using recombinant DNA technology and virus coding sequences, which are readily available to the public.

As used herein "chimeric" viral surface glycoproteins are ones that contain at least a portion of the extracellular domain of a viral surface glycoprotein of one virus and at least a portion of the transmembrane and/or cytoplasmic domains and/or signal peptide sequence of a different transmembrane glycoprotein from a different virus or other organism. Such chimeric proteins retain surface antigenic determinants against which an immune response is generated, preferably a protective immune response, and retain sufficient envelope sequence for proper precursor processing and membrane insertion. The operably linked transmembrane and/or cytoplasmic domains will serve to preferentially interact with the desired viral core protein components in VLP assembly, and thus increase the levels of viral surface glycoprotein in VLPs. The skilled artisan can produce chimeric viral surface glycoproteins using recombinant DNA technology and protein coding sequences, techniques known to those of skill in the art and available to the public. Such chimeric viral surface glycoproteins may be useful for increasing the level of incorporation of viral glycoproteins in VLPs for viruses that may naturally have low levels of incorporation.

For instance, HIV-1 is known to contain a low level of Env (7-14 trimers per virion). Thus, approximately only 1.5% of total proteins of the virion are Env proteins. Other enveloped viruses incorporate relatively much higher levels of viral glycoproteins into their virions. For example, the type B retrovirus mouse mammary tumor virus (MMTV) contains up to 58% of envelope protein, and the Pichinde virus, an arenavirus, contains up to 27% of envelope glycoprotein.

Figure 7:
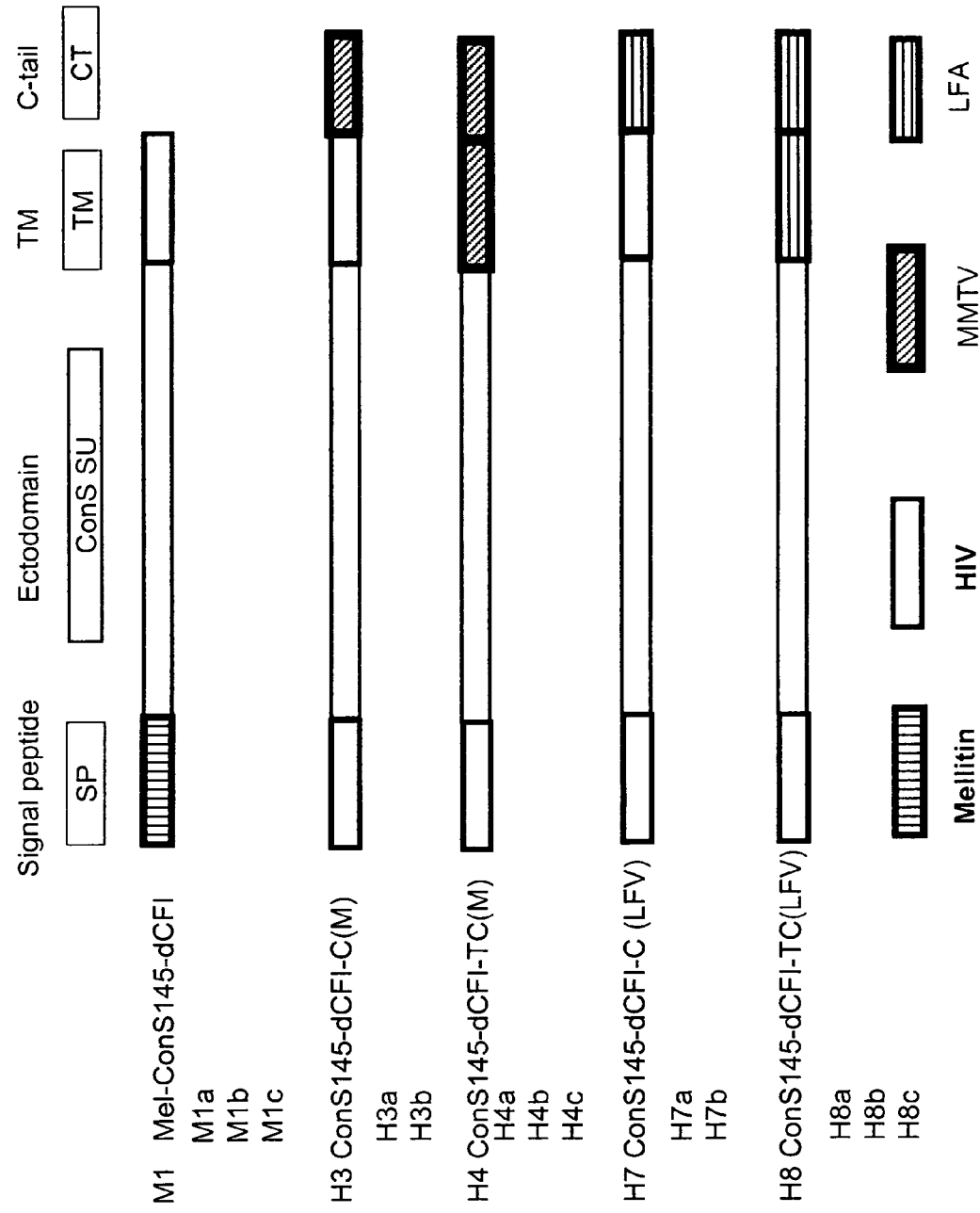
FIG. 7 illustrates a schematic diagram of modified HIV envelope glycoproteins having the transmembrane and/or cytoplasmic domains of the HIV envelope glycoprotein replaced with the transmembrane and/or cytoplasmic domains of the envelope glycoprotein of MMTV or LFV.

One factor governing the levels of viral envelope protein incorporated into virions may be the transmembrane (TM) and cytoplasmic tail (C-tail) domain. To enhance the level of HIV Env into VLPs, novel chimeric HIV Env (H3, H4, H7, H8) were constructed by replacing the transmembrane and/or cytoplasmic domains of the HIV envelope glycoprotein with the TM and/or C-tail domains of the mouse mammary tumor virus envelope glycoprotein (MMTV), the baculovirus glycoprotein Gp64 (Gp64), the Lassa Fever virus glycoprotein (LFV), or the influenza surface glycoprotein HA (HA), as illustrated in FIGS. 6 and 7.

Another factor in the level of incorporation of Env proteins in a virion is the signal sequence. The HIV-1 env gene, with its natural signal sequence expressed in any prokaryotic or eukaryotic expression system, showed low levels of synthesis. The signal sequences from honeybee mellitin is known to facilitate the intracellular transport of glycoproteins to the cell surface. Thus, the natural signal peptide (SP) of HIV-1 Env was replaced with the mellitin SP, as illustrated in FIG. 7 (top) to further enhance the expression of HIV-1 Env on the cell surface, so that more efficient incorporation of HIV Env into VLPs would be achieved.

VLPs based on cloned viral surface envelope glycoproteins, and further comprising core proteins from the same or different viruses, can be readily produced without the expense of undue experimentation by the ordinary skilled artisan using the teachings of the present application taken with vectors as described herein and what is well known to and readily accessible in the art.

In another embodiment, polyclonal and/or monoclonal antibodies capable of specifically binding to the VLP are provided. The term "antibody" is used to refer both to a homogenous molecular entity, or a mixture such as a serum product made up of a plurality of different molecular entities. Monoclonal or polyclonal antibodies, which specifically react with the VLPs of the present disclosure, may be made by methods known in the art. (e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1987)). Also, recombinant immunoglobulin may be produced by methods known in the art, including but not limited to, the methods described in U.S. Pat. No. 4,816,567, which is hereby incorporated by reference herein.

Antibodies specific for VLPs and viral surface envelope glycoproteins of viruses may be useful, for example, as probes for screening DNA expression libraries or for detecting the presence of the cognate virus in a test sample. Frequently, the polypeptides and antibodies will be labeled by joining, either covalently or noncovalently, a substance that provides a detectable signal. Suitable labels include, but are not limited to, radionuclides, enzymes, substrates, cofactors, inhibitors, fluorescent agents, chemiluminescent agents, magnetic particles and the like. United States Patents describing the use of such labels include, but are not limited to, U.S. Pat. Nos. 3,817,837; 3,850,752; 3,939,350; 3,996,345; 4,277,437; 4,275,149; and 4,366,241, which are hereby incorporated by reference herein.

Antibodies specific for VLPs and retroviral surface envelope glycoproteins may be useful in treating animals, including humans, suffering from cognate viral disease. Such antibodies can be obtained by the methods described above and subsequently screening the viral surface envelope glycoproteins-specific antibodies for their ability to inhibit virus uptake by target cells.

Compositions and immunogenic preparations of the present disclosure, including vaccine compositions, comprising the VLPs of the present disclosure and capable of inducing protective immunity in a suitably treated host and a suitable carrier therefor are provided. "Immunogenic compositions" are those which result in specific antibody production or in cellular immunity when injected into a host. Such immunogenic compositions or vaccines are useful, for example, in immunizing hosts against infection and/or damage caused by viruses, including, but not limited to, HIV, human T-cell leukemia virus (HTLV) type I, SIV, FIV, SARS, RVFV, Filovirus, Flavivirus, arenavirus, bunyavirus, pararnyxovirus, influenza virus, cytomegalovirus, herpesvirus, alphavirus, and flavivirus.

The vaccine preparations of the present disclosure can include an immunogenic amount of one or more VLPs, fragment(s), or subunit(s) thereof. Such vaccines can include one or more viral surface envelope glycoproteins and portions thereof, and adjuvant molecule and portions thereof on the surfaces of the VLPs, or in combination with another protein or other immunogen, such as one or more additional virus components naturally associated with viral particles or an epitopic peptide derived therefrom.

By "immunogenic amount" is meant an amount capable of eliciting the production of antibodies directed against the virus, in the host to which the vaccine has been administered. It is preferred for HIV and HTLV, among others, that the route of administration and the immunogenic composition is designed to optimize the immune response on mucosal surfaces, for example, using nasal administration (via an aerosol) of the immunogenic composition.

Immunogenic carriers can be used to enhance the immunogenicity of the VLPs from any of the viruses discussed herein. Such carriers include, but are not limited to, proteins and polysaccharides, microspheres formulated using (e.g., a biodegradable polymer such as DL-lactide-coglycolide, liposomes, and bacterial cells and membranes). Protein carriers may be joined to the proteinases, or peptides derived therefrom, to form fusion proteins by recombinant or synthetic techniques or by chemical coupling. Useful carriers and ways of coupling such carriers to polypeptide antigens are known in the art.

The immunogenic compositions and/or vaccines of the present disclosure may be formulated by any of the methods known in the art. They can be typically prepared as injectables or as formulations for intranasal administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes.

The active immunogenic ingredients are often mixed with excipients or carriers, which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable, aerosol or nasal formulations is usually in the range of about 0.2 to 5 mg/ml. Similar dosages can be administered to other mucosal surfaces.

In addition, if desired, the vaccines may contain minor amounts of auxiliary substances such as wetting or emulsifying agents, pH buffering agents, and/or other agents, which enhance the effectiveness of the vaccine. Examples of agents which may be effective include, but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. The effectiveness of the auxiliary substances may be determined by measuring the amount of antibodies (especially IgG, IgM or IgA) directed against the immunogen resulting from administration of the immunogen in vaccines which comprise the adjuvant in question. Additional formulations and modes of administration may also be used.

"Pharmaceutically acceptable salts" include, but are not limited to, the acid addition salts (formed with free amino groups of the peptide) which are formed with inorganic acids (e.g., hydrochloric acid or phosphoric acids) and organic acids (e.g., acetic, oxalic, tartaric, or maleic acid). Salts formed with the free carboxyl groups may also be derived from inorganic bases (e.g., sodium, potassium, ammonium, calcium, or ferric hydroxides), and organic bases (e.g., isopropylamine, trimethylamine, 2-ethylamino-ethanol, histidine, and procaine).

The immunogenic compositions and/or vaccines of the present disclosure can be administered in a manner compatible with the dosage formulation, and in such amount and manner as will be prophylactically and/or therapeutically effective, according to what is known to the art. The quantity to be administered, which is generally in the range of about 1 to 1,000 micrograms of viral surface envelope glycoprotein per dose and/or adjuvant molecule per dose, more generally in the range of about 5 to 500 micrograms of glycoprotein per dose and/or adjuvant molecule per dose, depends on the subject to be treated, the capacity of the hosts immune system to synthesize antibodies, and the degree of protection desired. Precise amounts of the active ingredient required to be administered may depend on the judgment of the physician or veterinarian and may be peculiar to each individual, but such a determination is within the skill of such a practitioner.

The vaccine or immunogenic composition may be given in a single dose; two dose schedule, for example two to eight weeks apart; or a multiple dose schedule. A multiple dose schedule is one in which a primary course of vaccination may include 1 to 10 or more separate doses, followed by other doses administered at subsequent time intervals as required to maintain and/or reinforce the immune response (e.g., at 1 to 4 months for a second dose, and if needed, a subsequent dose(s) after several months). Humans (or other animals) immunized with the VLPs of the present disclosure are protected from infection by the cognate virus.

It should also be noted that the vaccine or immunogenic composition can be used to boost the immunization of a host having been previously treated with a vaccine such as, but not limited to, DNA vaccine and a recombinant virus vaccine.

Except as noted hereafter, standard techniques for peptide synthesis, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) Experiments in Molecular Genetics, Cold Spring Harbor Laboratory, Cold Spring Harbor, N.Y., Old Primrose (1981) *Principles of Gene Manipulation*, University of California Press, Berkeley; Schleif and Wensink (1982) *Practical Methods in Molecular Biology*; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) *Genetic Engineering: Principles and Methods*, Vols. 1-4, Plenum Press, N.Y.

Abbreviations and nomenclature, where employed, are deemed standard in the field and commonly used in professional journals such as those cited herein.

All publications, including, but not limited to, patents, patent applications, and papers, cited in this specification are herein incorporated by reference as if each individual publication were specifically and individually indicated to be incorporated by reference herein as though fully set forth.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

EXAMPLES

Now having described the VLPs of the present disclosure in general, the examples below describe some embodiments of the VLPs. While embodiments of VLPs are described in connection with the following examples and the corresponding text and figures, there is no intent to limit embodiments of the VLPs to these descriptions. On the contrary, the intent is to

Example 1

Immune Responses Against VLPs Containing Modified HIV Envelope Proteins

Within the last decade, several vaccine approaches have been shown to be promising for induction of strong cellular immune responses controlling simian human immunodeficiency virus (SHIV) infection and replication upon subsequent pathogenic virus challenge. Among those the most effective immunogens are live attenuated viruses, recombinant viral vectors, DNA vaccines, or combinations of these components. However, some of these vaccine components may have serious potential safety concerns such as induction of chromosomal rearrangements or deletions in the host cell and a risk to immunodeficient recipients, which will be possible limitations on their approval for use in humans.

One of the major obstacles in developing effective HIV vaccines is the extreme difficulty in inducing neutralizing antibodies that are broadly reactive against many HIV-1 isolates. Several properties of HIV Env contribute to the difficulty of inducing neutralizing antibodies. HIV-1 Env, the main neutralizing target, is highly variable among isolates with five hyper-variable regions (V1-V5) which induce strain specific antibodies. Antibodies against these epitopes show little cross-reactivity. HIV Env is also extensively glycosylated, with 23 to 27 N-linked glycosylation sites which accounts for half of the total protein mass. Extensive glycosylations and highly variable loops may enable HIV-1 to evade host immune recognition by shielding some conserved neutralizing epitopes, such as regions of HIV-1 Env that bind to cellular receptors and coreceptors.

In attempts to expose conserved epitopes of HIV-1 Env, several strategies have been explored. These include the use of CD4-independent HIV Env, variable-loop deleted HIV Env, and glycosylation site mutants. HIV-1 mutants containing N-linked glycosylation site modifications located around the variable loops or deletions of the V1-V2 or V2 loops showed an increased susceptibility to neutralization by certain monoclonal antibodies or by patient sera. Changes in viral neutralization sensitivity indicate that such Env modifications may increase the availability and/or exposure of neutralization epitopes within the oligomeric viral Env protein. However, the effects of these modifications, deletions, or a combination of both mutations presented in the native oligomeric form of HIV-1 Env on inducing immune responses are not well understood. When the gag and env genes of HIV or simian immunodeficiency virus (SIV) are co-expressed in cells, these proteins are able to assemble on the plasma membrane to form virus-like particles (VLPs) containing viral core and Env proteins. The self-assembled macrostructure of VLPs presents conformational epitopes to the immune system, which are comparable to those of live virions. Enhanced binding of broadly neutralizing monoclonal antibodies to mutated HIV-1 Env expressed on cell surfaces has been demonstrated. The representative mutants of HIV Env with higher binding capability contained glycosylation site modifications around the receptor binding domain (3G), V1-V2 variable loop deletions (dV1V2), and a combination of both types of mutations (3G-dV2-1G). The present example demonstrates the immunogenicity of mutant HIV Env presented on VLPs, including induction of neutralizing antibodies against homologous and heterologous strains. The possible mechanism for inducing strong humoral and cellular immune responses after immunization with SHIV VLPs containing the mutated HIV Env is also discussed.

Methods

Cells, Proteins, and Antibodies

*Spodoptera frugiperda* Sf9 cells were maintained in suspension in serum-free SF900 II medium (GIBCO-BRL) and CV-1 cells in DMEM with 10% fetal calf serum (FCS) at 37° C. with $CO_2$. HIV 89.6 Env protein was partially purified from CV-1 cell lysates infected with a recombinant vaccinia virus expressing HIV 89.6 Env (rVV-HIV 89.6) using a lectin column as described previously (Jones et al., 1994, Kang et al., 2004). Purified mouse IgG, IgG1, IgG2a, IgG2b, IgG3, IgA, and goat antimouse-HRP for ELISA were purchased from Southern Biotechnology Associates (Birmingham, Ala.).

Production of SHIV VLPs

The construction and characterization of recombinant baculoviruses (rBV) expressing mutant Env were previously described (Kang et al., 2005). To produce SHIV VLPs, SF9 insect cells were coinfected with rBVs expressing the SIV Gag and mutant HIV Env at an MOI of 2 and 5, respectively. On day 3 postinfection, the culture medium was collected and centrifuged at 1,500×g for 20 min to remove cells and cellular debris. VLPs in the supernatant were pelleted at 28,000 rpm for 1 h using a SW28 rotor (Beckman). The pelleted VLPs were suspended in phosphate buffered saline (PBS), loaded on 60%, 35%, and 20% sucrose step gradients and centrifuged at 28,000 rpm for 60 min. The VLP band located between the 60% and 35% layers was collected, dialysed overnight against PBS, and stored at 4° C. for further analysis. Incorporation of HIV Env into VLPs was confirmed by Western blot using monkey anti-SHIV 89.6 sera (Dr. Patricia Fultz, University of Alabama at Birmingham). To determine the amount of HIV Env incorporated into VLPs, VLPs were lysed by RIPA buffer (0.1% NP40, 0.5% deoxycholic acid, 0.1% SDS, 150 mM NaCL, and 50 mM Tris, pH 8), serially diluted, and added to the ELISA plates coated with purified sheep antibody specific to the C5 domain (APTKAKRRV-VQREKR, aa 488-502 of SEQ. ID. NO: 1) of HIV (BH-10) Env (5 µg/ml) (CLINIQA, Fallbrook, Calif.). Purified HIV-1 gp120 protein (NIH AIDS reagent program, cat no. 7363) was used as a standard. The amount of HIV Env captured onto the ELISA plate was estimated using pooled HIV patient sera (NIH AIDS reagent program, cat no. 3957). Total protein concentration of VLPs was determined by the detergent compatible Bio-Rad protein assay kit.

Immunizations and Blood Sample Collection

Female inbred BALB/c mice (Charles River) aged 6 to 8 weeks were used. Each group consisted of six mice. The individual mouse was immunized subcutaneously with 50 µg VLP in 100 µl of PBS. Blood samples were collected by retro-orbital plexus puncture before immunization and 2 weeks after every immunization. After clotting and centrifugation, serum samples were collected and stored at −20° C. prior to antibody titration.

ELISA

All sera were individually collected, and IgG, IgG1, IgG2a, IgG2b, IgG3, and IgA antibody titers to HIV Env were determined by enzyme-linked immunosorbent assay (ELISA) as described previously (Kang, S. M. and Compans, R. W. Enhancement of mucosal immunization with virus-like particles of simian immunodeficiency virus. *J Virol* 77, 3615-23 (2003), which is incorporated by reference hererin). Briefly, 96-well microtiter plates (Nunc-Immuno Plate MaxiSorp™) were coated with 100 µl/well of partially purified HIV 89.6

Env protein (4 µg/ml) or the V3 loop peptide (IGPGRAF-YAR, amino acids 309 to 318 of SEQ ID NO. 3, 4 µg/ml) in coating buffer (0.1 M Sodium carbonate, pH 9.5) at 4° C. overnight. After blocking, 100-fold diluted sera were added to the wells and incubated at 37° C. for 1.5 hrs. Horseradish peroxidase-labeled goat anti-mouse IgG, IgG1, IgG2a, IgG2b, IgG3, and IgA, and the substrate O-Phenylenediamine (OPD) (Zymed, San Francisco, Calif.) were used to develop color. Optical density was read at 450 nm.

ELISPOT and Cytokine ELISA

Spleens were collected from individual mice at 2 weeks after the final immunization and single cell suspension was prepared, and used for enzyme-linked immunospot (ELISPOT) and cytokine ELISA as described (Kang & Compans, 2003). Briefly, anti-mouse IFN-γ, IL-2, IL-4 and IL-5 antibodies (BD-PharMingen) were used to coat Multiscreen 96-well filtration plates (Millipore) at 4° C. overnight and freshly isolated splenocytes ($1.5 \times 10^6$ cells) were added to each well. H2-Dd restricted HIV 89.6 Env peptide, IGPGRAFYAR (amino acids 309 to 318 of SEQ ID NO. 3) (Takahashi, H. et al. An immunodominant epitope of the human immunodeficiency virus envelope glycoprotein gp160 recognized by class I major histocompatibility complex molecule-restricted murine cytotoxic T lymphocytes. *Proc Natl Acad Sci USA* 85, 3105-9 (1988)) or wild type SHIV VLPs were added at a concentration of 2 µg/ml, and plates were incubated for 36 h at 37 with 5% $CO_2$. Biotinylated anti-mouse cytokine antibodies, streptavidin-HRP, and stable diaminobenzidine (Invitrogen, Carlsbad, Calif.) were used to develop spots. Spots were counted by an ImmunoSpot ELISPOT reader (Cellular Technology, Ltd.). Cytokine ELISA was performed as described previously (Quan, F. S., Cho, S. W. & Joo, K. H. Proliferation and cytokine production of lymphocytes from Clonorchis sinensis-infected rats in response to stimulators in vitro. *Zhongguo Ji Sheng Chong Xue Yu Ji Sheng Chong Bing Za Zhi* 20, 136-40 (2002), which is incorporated by reference herein). Briefly, spleen lymphocytes ($1.5 \times 10^6$ cells/well) were cultured in the presence of 5 µg of peptide or VLP stimulator as described above. The T-cell mitogen concanavalin A (5 µg/ml) was added to positive control wells. The culture supernatants were harvested on day 3 after stimulation. Cytokines were determined by following the manufacture's procedures (eBioscience, San Diego, Calif.).

Neutralization Assay

Figure 8:
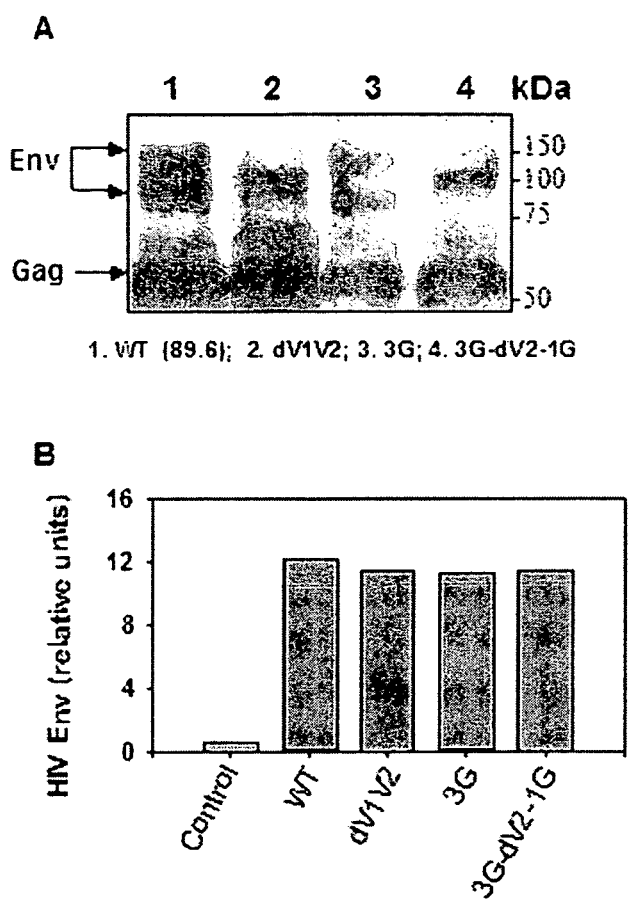
FIGS. 8A and 8B illustrate incorporation of wild type and mutant HIV Env into VLPs.

A neutralization assay was performed as described previously (Chackerian, B., N. L. Haigwood, and J. Overbaugh 1995, Characterization of a CD4-expressing macaque cell line that can detect virus after a single replication cycle and can be infected by diverse simian immunodeficiency virus isolates. Virology 213:386-94; Kang, S. M., F. S. Quan, C. Huang, L. Guo, L. Ye, C. Yang, and R. W. Compans 2005, Modified HIV envelope proteins with enhanced binding to neutralizing monoclonal antibodies. Virology 331:20-32, which are incorporated by reference herein). JC 53 BL cells were used for live HIV-1 89.6, IIIB virus or pseudovirion of non-T-cell line primary isolate YU2. Use of pseudovirions to assess neutralizing activities of HIV-1 has been described (Derdeyn, C. A., J. M. Decker, J. N. Sfakianos, X. Wu, W. A. O'Brien, L. Ratner, J. C. Kappes, G. M. Shaw, and E. Hunter. 2000, Sensitivity of human immunodeficiency virus type 1 to the fusion inhibitor T-20 is modulated by coreceptor specificity defined by the V3 loop of gp120. J. Virol. 74:8358-8367; Wei, X., J. M. Decker, H. Liu, Z. Zhang, R. B. Arani, J. M. Kilby, M. S. Saag, X. Wu, G. M. Shaw, and J. C. Kappes. 2002, Emergence of resistant human immunodeficiency virus type 1 in patients receiving fusion inhibitor (T-20) monotherapy. Antimicrob Agents Chemother 46:1896-905, which are incorporated by reference herein). In brief, plasmid pHIVSG3 containing the entire virus genome with a deleted 155 156 env gene (Dr. Beatrice Hahn, University of Alabama at Birmingham) was mixed with the plasmid containing HIV 157 158 env gene YU2 (NIH AIDS reagent program), transfected into 293T cells using calcium phosphate precipitation, and then pseudovirion particles were prepared as described (Bartz, S. R. & Vodicka, M. A. Production of high-titer human immunodeficiency virus type 1 pseudotyped with vesicular stomatitis virus glycoprotein. *Methods* 12, 337-42 (1997), which is incorporated by reference herein). Serum samples were heat inactivated (56° C., 30 min), 30 μl of diluted sera were mixed with 30 μl of diluted virus stock containing approximately 50 to 100 infectious particles for 1 hr at 37° C., and added to the cells. The neutralization activity was expressed as the percentage inhibition (%) in infectious spots and normalized by those of pre-immune sera.

Labeling of VLPs and FACS Staining

To label VLPs, 200 μg of VLPs were mixed with 2 μl of 10 mM of carboxylfluorescein succinimidyl ester (CFSE) in 1 ml of PBS and incubated in the dark for 10 min at 37° C. The labeled VLPs were extensively washed with PBS twice by ultracentrifugation through 20% sucrose cushion. For FACS staining, 10 μg labeled VLPs were mixed with dendritic cell (DC) enriched splenocytes ($1\times10^6$ cells) (Sailaja, G., S. Husain, B. P. Nayak, and A. M. Jabbar 2003, Long-term maintenance of gp120-specific immune responses by genetic vaccination with the HIV-1 envelope genes linked to the gene encoding Flt-3 ligand. J Immunol 170:2496-507.) The mixture of VLPs and cells were incubated for 20 min at 37° C., and stained with PE conjugated CD11c and PerCP conjugated B220 antibodies and analyzed as described (Kang, S. M., F. S. Quan, C. Huang, L. Guo, L. Ye, C. Yang, and R. W. Compans. 2005, Modified HIV envelope proteins with enhanced binding to neutralizing monoclonal antibodies. Virology 331:20-32, which is incorporated by reference herein).

Statistical Analysis

Serum antibody levels were recorded for individuals within all groups. Statistical comparisons of these data were carried out using the ANOVA and Npar1-way Kruskal-Wallis test of the PC-SAS system. A value of $P<0.05$ was considered significant.

Results

Production of SHIV VLPs with Mutated Env.

The antigenicity of a series of HIV Env mutant proteins expressed on the cell surface using broadly neutralizing monoclonal antibodies was recently reported (Kang et al., 2005). The N-linked glycosylation motif modification which contained mutations of Asn to Gln at aa 304, 341, and 363 in the V3/C3 domains of HIV-1 gp120 CD4 binding site (3G) was found to bind to a panel of broadly neutralizing monoclonal antibodies at higher levels as compared to the wild type control. Also, mutants with a deletion of both the V1 and V2 loop domains (dV1V2) or with a combination of both types of mutations (3G-dV2-1G: 3G and V2 loop deletion plus a mutation of Asn to Gln at an aa 635 in gp41) also bonded to the neutralizing monoclonal antibodies at high levels.

The present example demonstrates the immunogenicity of these mutant Env presented in a VLP form. The rBV expression system yields high expression levels of recombinant proteins allows the subsequent large scale manufacturing of a vaccine. To produce VLPs containing mutated HIV-1 Env, Sf9 insect cells were co-infected with rBVs expressing either HIV-1 wild type or mutant env genes (dV1V2, 3G, 3G-dV2-1G) (Kang et al., 2005) and an rBV expressing SIV Gag (Yamshchikov et al., 1995), and VLP in the culture supernatants were collected and purified (FIG. 8). The presence of wild type or mutant HIV Env and SIV Gag in the released VLPs was analyzed by Western blots and all HIV Env were found to be incorporated at high levels. To quantify the amounts of HIV Env incorporated into VLPs, HIV Envs in VLPs were captured onto an ELISA plate coated with a constant domain C5 specific monoclonal antibody and the captured HIV Env were determined using patient sera. HIV Env mutants were found to be incorporated into VLPs at equivalent levels as wild type (FIG. 8B).

Antibody Responses after Immunization with VLPs Containing HIV Env Mutants

Figure 9:
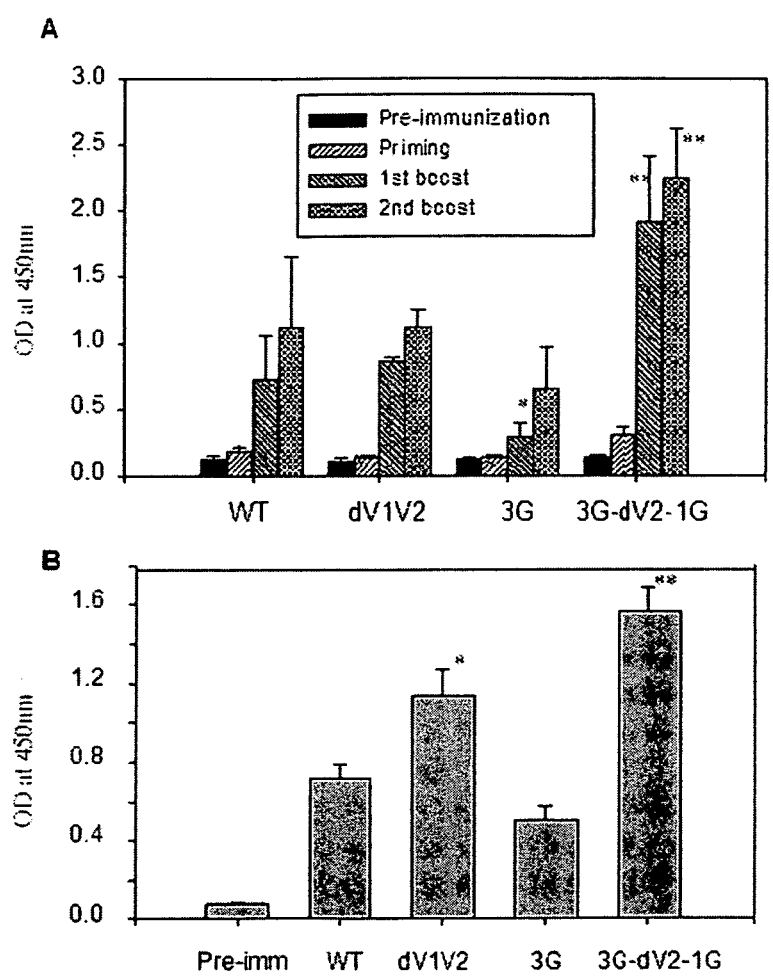
FIGS. 9A and 9B illustrate IgG antibody responses against HIV Env after immunization with SHIV VLPs.

Serum samples were collected after each immunization, and HIV Env-specific total IgG antibody levels were determined by ELISA using lectin-affinity column purified HIV Env 89.6 as a coating antigen (FIG. 9A). The levels of HIV Env specific IgG were found to be significantly increased after the first boost (P<0.0001) and were highest after the second boost in all groups.

Mice immunized with SHIV VLPs containing a combination of glycosylation and variable loop deletion (3G-dV2-1G) showed the highest level of IgG binding to HUV Env. IgG levels induced in the group of mice immunized with SHIV VLPs containing the mutant dV1V2 were similar to those induced in wild type SHIV VLPs. Antibody levels induced by the 3G mutant VLPs were lower than the wild type control after the $1^{st}$ boost (p<0.05) but differences were not statistically significant after the $2^{nd}$ boost. The Gag group of mice immunized with the Env-negative SIV Gag VLPs showed similar levels of antibody responses as pre-immune sera (data not shown).

To determine the antibody response to the V3 loop peptide, a strain specific neutralizing epitope, antibody levels were analyzed using ELISA plates coated with the 89.6 V3 loop peptide. It is interesting to note that levels of V3-loop binding antibodies were significantly higher in mice immunized with dV1V2 mutant VLPs than with wild type although both groups were similar in levels of antibody binding to the whole HIV Env antigen (FIG. 9B). These results indicate that SHIV VLPs with modified Env protein are as immunogenic as wild type SHIV VLPs in inducing antibody responses binding to the HIV Env antigen and that VLPs are strong immunogens even in the absence of adjuvant.

Figure 10:
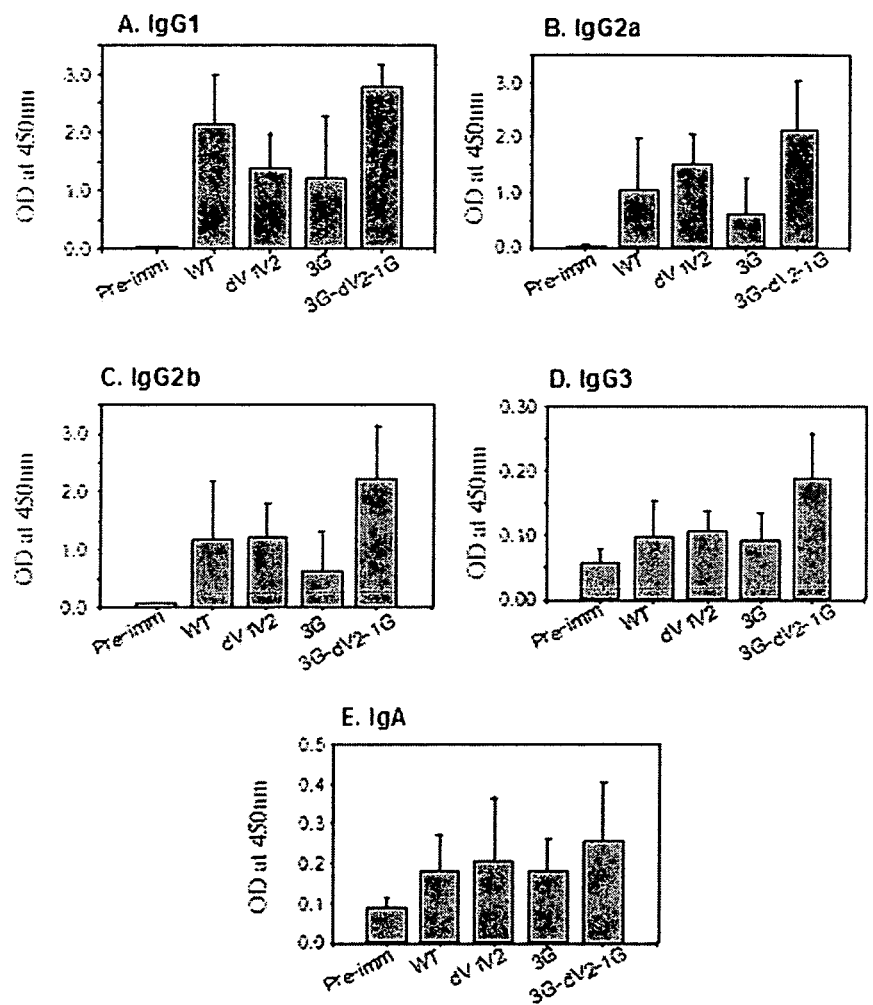
FIGS. 10A-E illustrate a comparison of serum IgG isotype antibody responses against HIV Env. The production of isotype antibodies against the HIV Env protein after the $2^{nd}$ boost was measured by an ELISA. Results are expressed as the arithmetic mean±SD from 6 mice per group. Error bars indicate standard deviation (SD).

To further characterize antibody production, serum IgG subtypes IgG1, IgG2a, IgG2b, IgG3 and IgA were determined after the second boost as shown in FIG. 10. All isotype antibodies binding to the HIV Env antigen were observed in all groups of mice immunized with wild type or mutant SHIV VLPs. Various isotype antibodies were induced at higher levels in the 3G-dV2-1G group than other groups although the differences between wild type and mutants were not statistically significant. When comparing the serum IgG1 and IgG2a antibody levels specific to HIV Env, IgG1 levels were found to be higher than those of IgG2a, except for the dV1V2 group which showed similar levels of both isotypes. These results suggest that SHIV VLPs induce mixed subtypes of IgG antibody responses, indicating that Th1- and Th2-like helper cell responses are elicited.

Neutralization Activities

Figure 11:
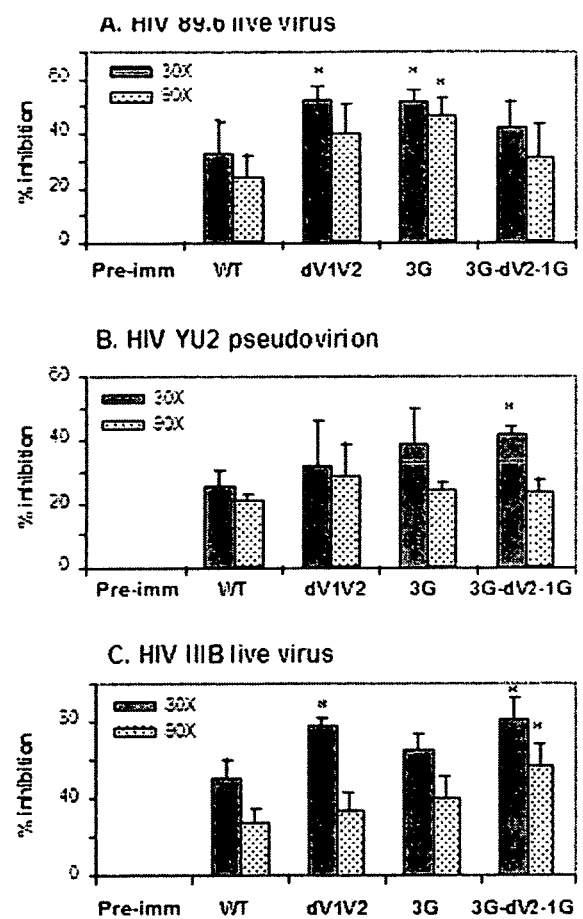
FIGS. 11A and 11C illustrate neutralization activities in sera of mice immunized with VLPs. To compare the neutralization activities in immune sera from groups, individual serum samples (six samples per group) after the $2^{nd}$ boost were diluted to 30 (30×) and 90 times (90×). The neutralization activity was expressed as the percentage (%) of inhibition in infectivity and normalized as compared to those of preimmune samples. The activity of individual samples was determined as average from three independent experiments. Results are expressed as the arithmetic mean±SD from 6 mice per group. Error bars indicate the standard deviation (SD). Statistically significant differences are indicated; between WT and mutants as * ($P<0.05$).
FIG. 11B: illustrates neutralization activity against HIV YU2 pseudovirions.

First, neutralizing activities against the homologous strain, HIV 89.6 virus were determined. Using luciferase reporter viruses pseudotyped with a specific HIV Env or live virus, normal mouse serum exhibited 20 to 50% background neutralization activities compared to immune sera. Similarly, relatively high background neutralizing activity in pre-immune sera was observed, and thus, neutralizing activities represented as percentiles of infectivity inhibition in immune sera were normalized based on those in pre-immune sera (FIG. 11). The 3G mutant SHIV VLPs induced the highest level of neutralization activities resulting in over 50% reduction in infectivity, which is a significant increase compared to VLPs containing wild type Env (P<0.05) (FIG. 11A). SHIV VLPs with a dV1V2 mutation also showed significantly higher neutralization activity than the wild type SHIV VLPs (P<0.05). The combination mutant, 3G-dV2-1G also induced neutralization activity.

Neutralization activities were also determined using SG3 virions pseudotyped with YU2, a primary isolate using CCR5 as a coreceptor (Li, A., H. Katinger, M. R. Posner, L. Cavacini, S. Zolla-Pazner, M. K. Gorny, J. Sodroski, T. C. Chou, T. W. Baba, and R. M. Ruprecht. 1998, Synergistic neutralization of simian-human immunodeficiency virus SHIV-vpu+ by triple and quadruple combinations of human monoclonal antibodies and high-titer anti-human immunodeficiency virus type 1 immunoglobulins. J Virol 72:3235-40.) Immune sera from mutants 3G and dV1V2 VLPs showed slightly higher neutralizing activities against the YU2 strain compared to that obtained with the wild type SHIV VLPs although statistically not significant (FIG. 11B). The 3G-dV2-1G mutant VLP-immune sera also showed high neutralization activity against the YU2 infectivity. In case of the laboratory-adapted, T cell tropic 111B strain virus using CXCR4 as a coreceptor (FIG. 11C), mutant dV1V2 sera showed the highest neutralizing activity with up to 80% reduction against the 111B strain. Neutralizing activity against 111B virus of the 3G-dV2-1G mutant immune sera was higher than that of wild type sera (FIG. 11C). Overall, these results indicate that immunization with SHIV VLPs in the absence of adjuvant can induce neutralizing activities against homologous as well as heterologous strains and that mutated HIV Env containing variable loop deletions or reduced glycosylations presented in VLPs can further enhance these neutralizing activities.

Cytokine Responses Induced by Immunization with SHIV VLPs

Figure 12:
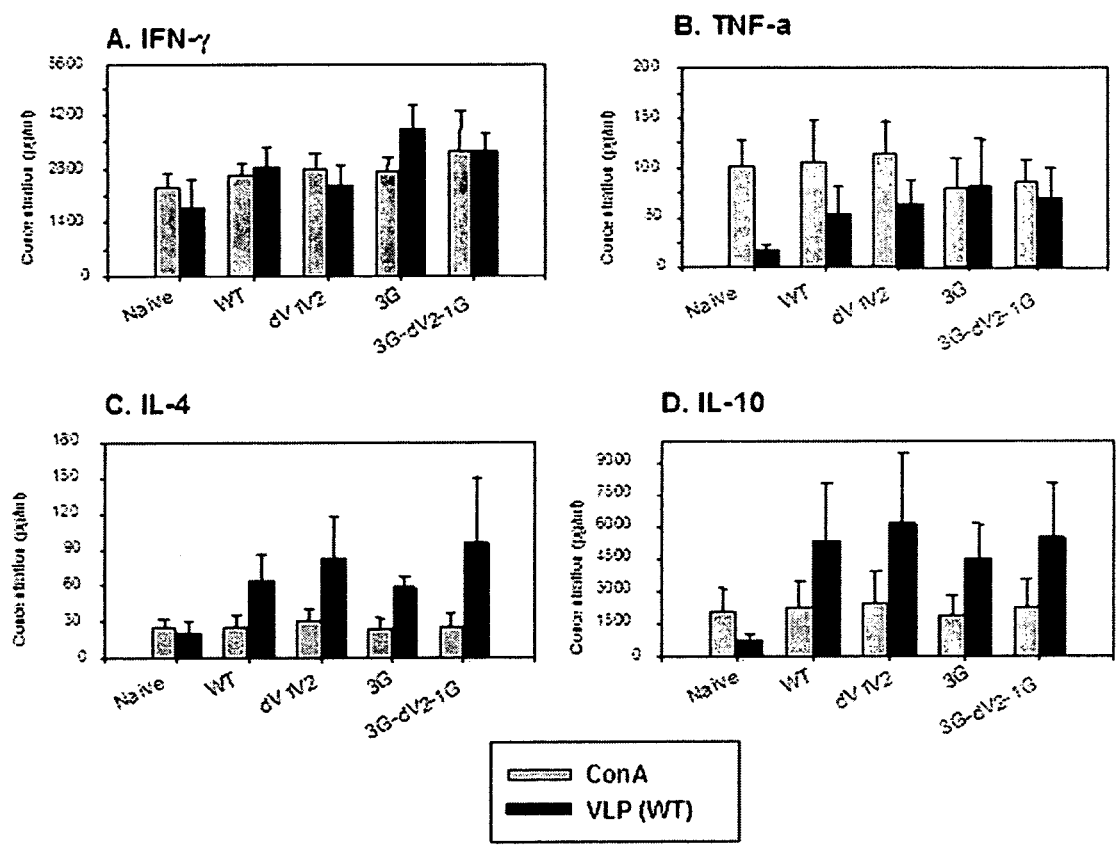
FIGS. 12A-12D illustrate cytokine production in responses to VLP stimulation. Spleen cells from mice immunized with SHIV VLPs or from naïve mice were incubated with VLPs. Bars indicate standard deviations from six mice per group.

To evaluate cellular immune responses, the levels of a series of cytokines (IFN-γ, TNF-α, IL-4, and IL-10) produced by splenocytes from immunized mice were determined. Cytokine responses stimulated using SHIV VLPs, a multi-epitope antigen, and Con A, a strong T cell stimulator as a positive control were compared. Con A stimulated splenocytes to secrete cytokines equally well from immunized and naïve mice, whereas stimulation with wild type SHIV VLPs resulted in differential effects on splenocytes in immunized and naïve mice (FIG. 12). The differences between immunized groups were not statistically significant. IFN-γ was observed at moderately higher levels in mice immunized with VLPs containing the 3G or 3G-dV2-1G mutants (FIG. 12A). Cytokines TNF-α, IL-4, and IL-10 were produced at 4 to 10-fold higher levels in SHIV VLP immunized mice than in naïve mice (FIG. 12B, C, D). Interestingly, SHIV VLP stimulated splenocytes to secrete IL-4 and IL-10 at significantly higher levels than Con A, while other cytokines (IFN-γ, TNF-α) were produced at similar levels by both stimulators (FIG. 12). These results indicate that SHIV VLPs are a strong stimulator for inducing cytokine production.

HIV Env Peptide Specific Cytokine Responses

Figure 13:
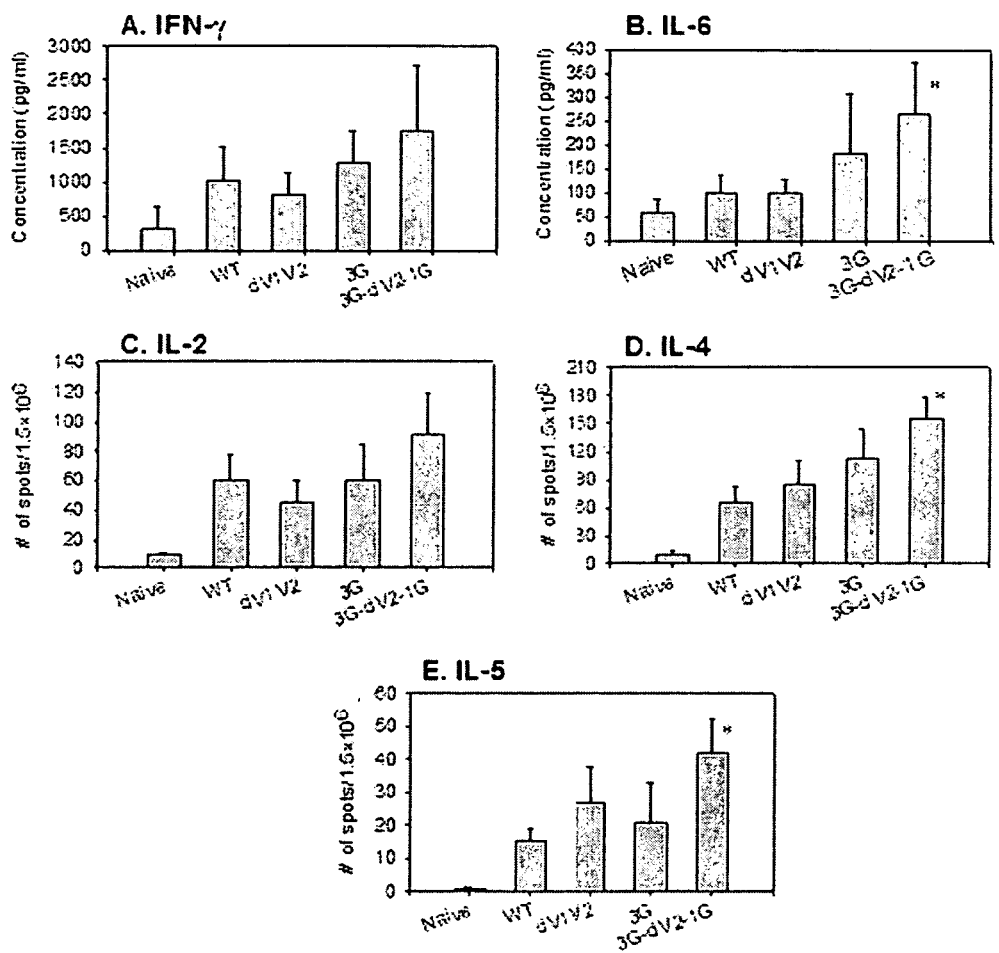
FIGS. 13A-13E illustrate concentrations of HIV Env peptide specific cytokines produced by spleen cells.

To evaluate HIV Env peptide specific cytokine production, splenocytes from immunized or naïve mice were cultured in the presence of HIV Env 89.6 derived-peptide as described in Methods. Depending on the types of cytokines, either ELISA (IFN-γ, IL-6) or ELISPOT (IL-2, 4, 5) assays were used (FIG. 13). Approximately 4 to 5-fold increases in IFN-γ and IL-6 levels were observed from the 3G or 3G-dV2-1G groups compared to the naïve group (FIGS. 13A and 13B). The dV1V2 group showed a similar level of IFN-γ and IL-6 as the wild type VLPs, which was 2 to 3 fold higher than the naïve group. All VLP-immunized groups showed over a 10-fold increase in numbers of cytokine (IL-2, 4, 5) secreting cells compared to the naïve mice (FIGS. 13C, 13D, and 13E). Mutant 3G-dV2-1G groups increased IL-4, IL-5, and IL-6 secreting cells by over 2-fold compared to the wild type group (FIGS. 13 B, 13D, and 13E), which is statistically significant ($p<0.05$). No significant differences between groups in the IL-2 level were observed. Thus, these results indicate that SHIV VLPs can induce both Th1 and Th2 types of cellular immune responses, and that mutations in HIV Env affect the levels of cellular immune responses.

SHIV VLPs Interact with Antigen Presenting Cells

To analyze the mechanism by which VLPs function as a strong immunogen inducing both humoral and cellular immune responses in the absence of adjuvant, the phenotypes of cells binding to VLPs were determined. CFSE-labeled wild type or mutant SHIV VLPs were incubated with dendritic cell (DC)-enriched splenocytes, extensively washed to remove unbound VLPs, and then splenocytes were stained with PE-conjugated CD11c antibody, a marker for DC populations.

Figure 14:
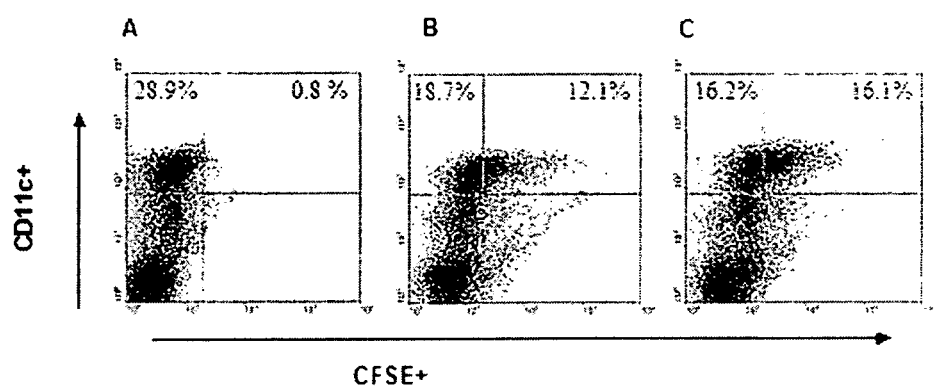
FIGS. 14A-14C illustrate that VLPs bind to dendritic (DCs) and B cells. For FIGS. 14 A to C, in vivo DC-enriched splenocytes were incubated with CFSE-labeled VLPs for 20 min at 37° C., washed, and then stained with PE-conjugated CD11c+ antibody. $CD11c^+CFSE^-$ and $CD11c^+CFSE^+$ populations are represented as percentages among the total lymphocytes analyzed.

DC-enriched splenocytes obtained by an injection of Flt3 ligand encoding DNA (as described in Sailaja, G., S. Husain, B. P. Nayak, and A. M. Jabbar. 2003, Long-term maintenance of gp120-specific immune responses by genetic vaccination with the HIV-1 envelope genes linked to the gene encoding Flt-3 ligand. J Immunol 170:2496-507, which is hereby incorporated by reference herein) showed approximately 30% CD11c+ cells in the gated lymphocytes (FIG. 14). $CD11c^+CFSE^+$ populations in the gated lymphocytes were 12.1% when cells were incubated with the CFSE-labeled wild type SHIV VLPs (FIG. 14B). The CFSE-labeled 3G-dV2-1G SHIV VLPs were associated with 16.1% of the gated lymphocytes (FIG. 14C), whereas other mutants (dV 1V2, 3G) including the Gag alone VLPs showed a similar level of $CD11c^+CFSE^+$ populations as wild type VLPs (data not shown). When stained with B220 antibody, a B cell marker, $B220^+CFSE^+$ populations were found to be 15 to 17% of gated lymphocytes representing approximately 30% of total B cells, and no significant differences were observed among the different VLPs (data not shown). Thus, the results indicate that VLPs interact with DCs and B cells, both of which are antigen-presenting cells.

Discussion

The current example explored the immunogenicity of modified HIV Env presented by VLPs, and particularly investigated the possibility of improving the induction of broadly reactive neutralizing antibodies. The HIV Env mutants studied include a deletion of the V1-V2 loops (dV1V2), reduced glycosylations around the receptor binding domain (3G), and a combination of both types of mutations. All immunizations were performed in the complete absence of adjuvants. Higher neutralizing activities against the homologous strain 89.6 and a heterologous strain IIIB were observed in sera from immunizations with mutants dV1V2 and 3G VLPs. VLPs containing a combination mutant (3G-dV2-1G) showed the highest levels of binding antibodies including all IgG isotypes, neutralizing activity against the heterologous primary isolate YU2, and cellular immune responses as determined by cytokine productions. In addition, VLPs were found to directly bind to DCs.

Induction of broadly reactive neutralizing antibodies against various HIV-1 strains by vaccination is known to be extremely difficult, which is a major obstacle in developing effective vaccines against HIV-1. The present example shows that the dV1V2 HIV Env on VLPs induced higher levels of antibodies binding to the V3 loop peptide antigen, and moderately enhanced neutralizing activity against the homologous strain 89.6 and the heterologous strain IIIB compared to the VLPs containing unmodified 89.6 Env. The V3 loop region of HIV-1 Env is directly involved in the binding of gp120 to chemokine receptors. HIV-1 neutralizing antibodies against the V3 loop are thought to prevent the binding of gp120 to either CCR5 or CXCR4, thus abolishing viral fusion with its target cell (Sirois, S., Sing, T. & Chou, K. C. HIV-1 gp120 V3 loop for structure-based drug design. *Curr Protein Pept Sci* 6, 413-22 (2005)). Monoclonal antibody 447-52D was shown to neutralize 35 out of 38 primary isolates carrying the GPGR V3 motif regardless of whether the viruses belonged to clades A, B, F, or H (Zolla-Pazner, S., P. Zhong, K. Revesz, B. Volsky, C. Williams, P. Nyambi, and M. K. Gorny. 2004, The cross-clade neutralizing activity of a human monoclonal antibody is determined by the GPGR V3 motif of HIV type 1. AIDS Res Hum Retroviruses 20:1254-8).

The present results also suggest that deletion of the V1-V2 loops may play a role in exposing the V3 loop, resulting in enhancement of antibodies against the V3 loop peptide, which may contribute to enhancing neutralizing activities. N-linked glycosylations on HIV Env are known to be engaged in shielding some important neutralizing epitopes. Elimination of the highly conserved glycans within and adjacent to the V3 loop can render mutants with modified HIV-1 Env more susceptible to neutralization by antibodies against the CD4 binding site and CD4-induced epitopes, and to modulate chemokine receptor bindings. Macaques infected with V3 loop glycan-deficient viruses can elicit broadly neutralizing antibodies at higher levels than those with wild type virus. The present example demonstrates that 3G VLPs elicited higher levels of neutralizing activity against the homologous HIV-1 89.6 strain. VLPs containing a combination mutant, 3G-dV2-1G, exhibited significantly enhanced neutralizing activity against the heterologous strains (YU2, IIIB). This may be due to high levels of binding antibodies coating the virion.

The trimeric form of HIV Env represents the major target for neutralizing antibody induction. Monomeric HIV Env protein exposes immunogenic but silent non-neutralizing domains which would not be seen in the native oligomeric form. It was reported that immunizing mice with a recombinant vaccinia virus expressing a V1-V2 loop-deleted HIV-1 gp160 and boosting with the same mutant protein did not increase neutralizing activity compared to the wild type immunogen (Kim, Y. B., D. P. Han, C. Cao, and M. W. Cho. 2003, Immunogenicity and ability of variable loop-deleted human immunodeficiency virus type 1 envelope glycoproteins to elicit neutralizing antibodies. Virology 305:124-37). In contrast, immunization with oligomeric HIV-1 Env with a deletion of V2 loop or DNA/recombinant adenovirus expressing V1 V2 deletion constructs significantly increased neutralizing antibody responses (Barnett, S. W., S. Lu, I. Srivastava, S. Cherpelis, A. Gettie, J. Blanchard, S. Wang, I. Mboudjeka, L. Leung, Y. Lian, A. Fong, C. Buckner, A. Ly, S. Hilt, J. Ulmer, C. T. Wild, J. R. Mascola, and L. Stamatatos. 2001, The ability of an oligomeric human immunodeficiency virus type 1 (HIV-1) envelope antigen to elicit neutralizing antibodies against primary HIV-1 isolates is improved following partial deletion of the second hypervariable region. J. Virol. 75:5526-5540; Yang, Z. Y., B. K. Chakrabarti, L. Xu, B. Welcher, W. P. Kong, K. Leung, A. Panet, J. R. Mascola, and G. J. Nabel. 2004, Selective modification of variable loops alters tropism and enhances immunogenicity of human immunodeficiency virus type 1 envelope. J Virol 78:4029-36). An advantage of using VLPs as vaccine candidates is the incorporation of oligomeric HIV-1 Env proteins into VLPs Thus, the present results indicate that presenting mutant HIV-1 Env on VLPs could be used for inducing neutralizing antibodies against both homologous and heterologous HIV strains.

Soluble recombinant viral proteins frequently exhibit poor immunogenicity and inability to stimulate cellular immune responses. Purified gp120 soluble protein vaccines failed to prevent HIV-1 infections in human trials and also did not induce neutralizing antibodies to primary isolates. The co-administration of adjuvants is needed to initiate effective immune responses against soluble immunogens. Unfortunately, many adjuvants (cholera toxin, monophosphoryl lipid A, CpG oligonucleotides) have potential side effects such as toxicity or inflammation, and thus are not currently licensed for use in human vaccines. This example demonstrated that VLPs containing HIV Env could induce humoral and cellular immune responses without use of adjuvants. The present example also demonstrates that VLPs stimulated lymphocytes to secrete various cytokines (IFN-γ, TNF-α, IL-4, IL-10) as strong as Con A, a well-known T lymphocyte stimulator. Interestingly, a combination mutant 3G-dV2-1G VLPs induced higher levels of certain cytokines (IL-4, IL-5, IL-6) in responses to HIV Env peptide stimulation than the wild type Env VLPs.

To better understand the possible underlying mechanism of immunogenicity of VLP antigens, the phenotypes of immune cells interacting with VLPs were investigated; in vivo DC-enriched splenocytes were incubated with CFSE-labeled VLPs. These studies demonstrated, for the first time, that enveloped VLPs interact with CD11c+DC populations as well as B220+B cells. These results suggest that VLP-loaded DCs play a role as an antigen presenting cells stimulating lymphocytes (data not shown), which may be a reason for VLPs being strong immunogens.

In summary, the present example demonstrates that design of VLPs containing modified HIV Env can be an effective strategy to develop vaccines inducing neutralizing activity as well as cellular immune responses against HIV-1. Also, identifying immune cells interacting with HIV VLP antigens provides insight for better understanding of VLP-induced immune responses and designing effective HIV immunogens.

Example 2

Production and Characterization of Chimeric RVFV GP-SIV Gag VLPs

The genes for RVFV glycoprotein GN and GC subunits were cloned into the recombinant baculovirus (rBV) transfer vector pC/pS1 under a pPol/pCap hybrid promoter and rBVs expressing RVFV GN (rBV-GN), and GC (rBV-GC) proteins were generated following established procedures. Expression of GN and GC proteins by rBVs in Sf9 insect cells was verified by radioactive labeling coupled with immunoprecipitation using a hyper-immune mouse sera against RVFV.

To determine whether the RVFV glycoproteins can be incorporated into chimeric SIV Gag VLPs, Sf9 cells were infected by rBV-GN and rBV-GC at an MOI of 5 for each along with rBV-SIV Gag at an MOI of 2. At 60 hs post infection, the cell culture medium was collected and clarified by centrifugation at 6000 rpm for 20 min, and the VLPs released into the medium were concentrated by centrifugation at 28000 rpm. The pellet was resuspended in PBS and the VLPs were purified by centrifugation through a sucrose gradient (10-50%). The band containing VLPs was collected, diluted in PBS, and VLPs were pelleted by centrifugation at 30000 rpm and resuspended in PBS. Protein concentration in the VLP preparation was determined and the VLPs was adjusted to a final protein concentration of 1 mg/ml. The VLP preparations were stored in aliquots at −80° C. and used for VLP characterization as well as immunization studies as described below.

Figure 15:
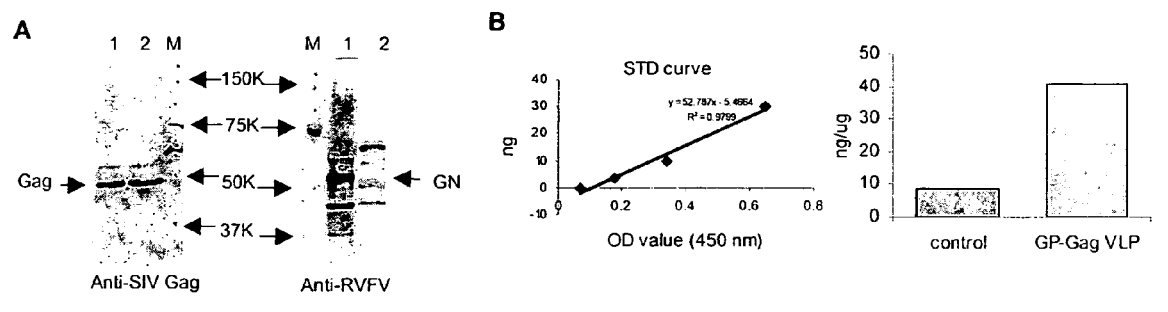

The presence of SIV Gag and RVFV glycoproteins in VLP preparations were analyzed by SDS-PAGE (5 µg per lane) followed by Western blot using antibodies against SIV Gag or a mixture of monoclonal antibodies against the RVFV GN protein respectively. As shown in FIG. 15A below, the SIV Gag proteins were detected in VLPs produced in rBV-SIV Gag infected Sf9 cells (lane 2), while both the RVFV GN and the SIV Gag proteins were detected in VLPs produced in Sf9 cells infected with rBV-SIV Gag plus rBV-GN and rBV-GC (lane 1). The amount of RVFV glycoproteins in VLP preparations was determined by ELISA. Recombinant vaccinia virus expressing RVFV GN-Histag in which a Histag (6-His) was fused to the C-terminus of the GN extracellular domain and the GN-Histag proteins were expressed in HeLa cells and purified using a histag-protein purification kit (Qiagen). A standard curve was constructed by coating the microtiter plate with serial dilutions of purified GN-Histag proteins mixed with the control SUV Gag VLPs. As shown in FIG. 15B, the amounts of RVFV glycoproteins in GP-SIV-Gag VLP preparations are about 4% of the total protein in the VLP preparation, with a calculated concentration of about 40 ng/ug in the VLP preparation.

Figure 16:
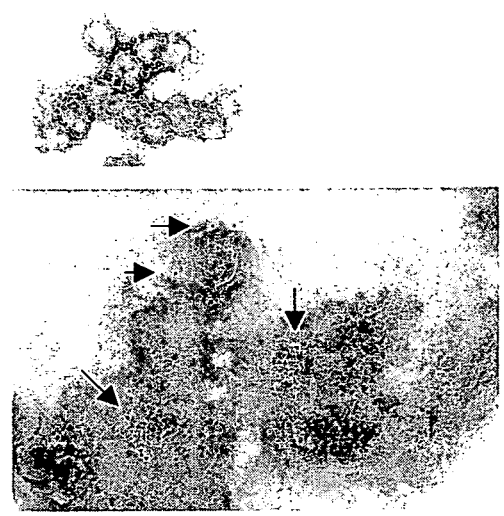
FIG. 16 illustrates an EM examination of chimeric RVFV GP-SIV Gag VLPs.

To investigate whether the RVFV glycoproteins are released in the form of VLPs, the GP-SIV-Gag VLP preparations were examined by electron microscopy. As shown in FIG. 16A, VLPs with uniform morphology were observed in the chimeric GP-SIV-Gag preparations (FIG. 16B), which are similar in size and morphology to SIV Gag VLPs. Furthermore, as shown in FIG. 16B, the RVFV glycoproteins were found to be incorporated into SIV Gag VLPs as detected by immune-gold labeling.

Figure 17:
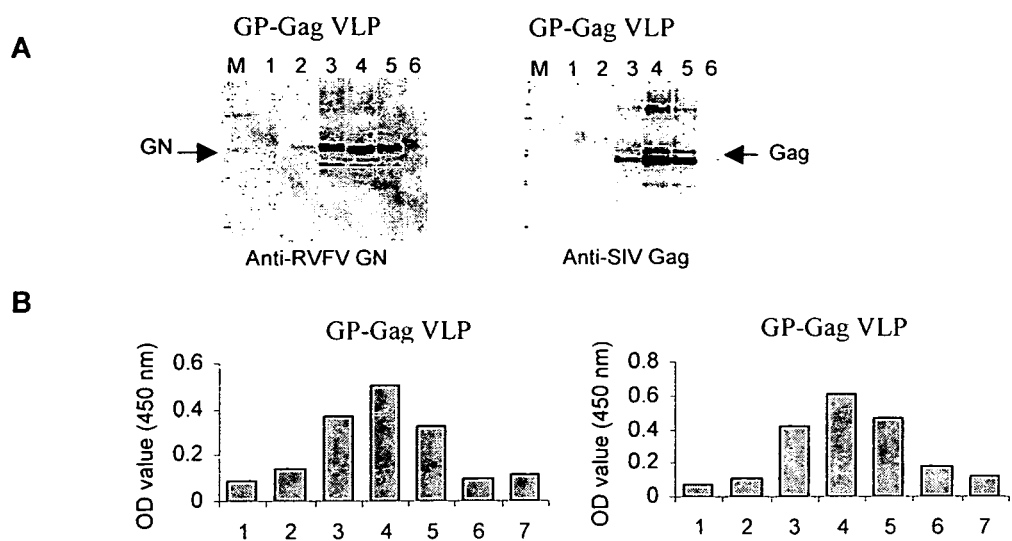
FIGS. 17A-17B illustrate the co-localization of RVFV GP with the SIV Gag proteins in sucrose gradients. The purified RVFV GP-Gag VLPs (100 ug VLPs dissolved in 500 ul PBS) were overlaid onto the top of a discontinuous sucrose gradient (2 ml of 10%, 20%, 30%, 40%, 50%, and 60% sucrose) and centrifuged in a SW41 rotor at 30000 rpm at 4° C. for 2 hr. After centrifugation, the six sucrose gradient layers were carefully collected and the proteins in each fraction were pelleted by centrifugation at 35000 rpm for 1 hr and the pellets were resuspended in 60 ul of PBS.

To determine the levels of RVFV glycoproteins associated with SIV Gag VLPs in the GP-SIV Gag VLP preparations, the GP-SIV-Gag VLPs were fractionated by centrifugation through a discontinuous sucrose gradient and the presence of RVFV glycoproteins as well as SIV Gag proteins in different sucrose fractions were determined by Western blot and ELISA. As shown in FIG. 17, after centrifugation through a sucrose gradient, the majority of RVFV glycoproteins in GP-SIV Gag VLPs co-localized with the SIV Gag proteins in the middle fractions (fractions 3 to 5, 30-50%). These results show that a significant amount of RVFV glycoproteins is incorporated into the SIV Gag VLPs.

To determine their potential for use as a vaccine antigen, immunogenicity of VLPs was evaluated in mice. Balb/c mice (groups of 6) were immunized by intramuscular injection with GP-Gag VLPs containing 2 ug of RVFV glycoproteins (about 50 ug total protein as determined by ELISA). The control group mice were immunized with 50 ug of SIV Gag VLPs. Mice were boosted at 3 and 6 weeks after priming with the same VLP preparations at the same dose. Blood was collected by retro-orbital bleeding at two weeks after each immunization and serum samples were heat-inactivated and stored at −80° C. until analysis.

Figure 18:
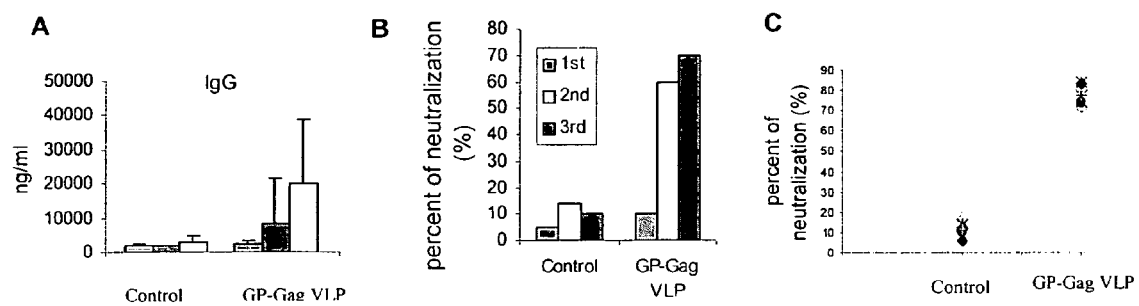
FIGS. 18A-18C illustrate the analysis of antibody response induced by immunization with chimeric RVFV VLPs as described in Example 2. Mice were immunized with GP-Gag VLPs or SIV Gag VLPs (Control) as described in the text. Blood samples were collected two weeks after each immunization, heat inactivated, and then analyzed for antibodies to RVFV. For FIG. 18A, microtiter plates were coated with purified RVFV GN-Histag proteins (0.4 ug per well) and the levels of antibodies against GN were determined by ELISA following standard procedures. A standard curve was generated by coating the wells with serial dilutions of purified mouse IgG with known concentrations as described in previous studies for calculating the concentrations of GN-specific antibodies in serum samples. Numbers 1, 2, and 3 indicate the serum samples collected after first, second, and third immunizations respectively. Error bars indicated standard variations in each group. For FIG. 18B, MP12 virus (an attenuated RVFV) was neutralized by sera from immunized mice after each immunization. MP12 (100 pfu) was incubated with serum samples (pooled for each group after each immunization) at 1:40 dilution in DMEM at 37° C. for 1 hr. The virus-serum mixtures were then added to VERO E6 cells seeded in a 12-well plate and tittered by a plaque assay. MP12 virus incubated with DMEM was used as controls. The neutralizing activity of serum samples was calculated as the percentage of plaque number reduction as compared to the control wells (Percentage of neutralization).

The levels of antibodies specific for the RVFV glycoprotein GN in mouse sera were determined by ELISA using purified GN-Histag proteins as coating antigens. As shown in FIG. 18A, immunization with GP-Gag VLPs induced significant levels of antibodies against the RVFV GN. The neutralizing activity of sera samples from immunized mice against RVFV were determined by a neutralization assay against RVFV MP12 (obtained from the US Army Medical Research Institute), an attenuated RVFV strain that can be used under BSL-2 containment. MP12 was grown in VERO E6 cells and viruses released into the medium was harvested 72 hr post infection, clarified of cell debris by centrifugation at 1200 rpm for 10 min, and stored at −80° C. in aliquots, and the titers of MP12 virus stocks determined by a plaque assay. Typically, a titer of 2 to 5×10$^8$ pfu/ml is obtained. To assess the neutralizing activity of serum samples from immunized mice, MP12 (100 pfu) was added to sera samples diluted in DMEM (at 1:40 dilution) in duplicates. Virus added to DMEM without serum was used as control. After 1 hr incubation at 37° C., the virus-serum mixture (in serial 3-fold dilutions) was added to VERO E6 cells seeded in a 12-well plate to determine the residual virus titer by plaque assay. The neutralizing activity of serum samples was calculated as the percentage of plaque number reduction in comparison to control wells (virus incubated with DMEM only) using the formula: (the average number of pfu in control well—the average plaque of pfu in sample well)/the average number of pfu in control well× 100%. As shown in FIG. 18B, pooled serum samples from mice immunized with GP-Gag VLPs exhibited higher levels of neutralizing activity after the second immunization. Also, as shown in FIG. 18C, the neutralizing activity of individual sera samples collected from each group showed that the serum samples from GP-Gag VLP immunized mice exhibit significantly higher levels of neutralizing activity than the serum samples from the control SIV Gag-VLP immunized mice.

In summary, co-expression of RVFV glycoproteins with the SIV Gag protein led to the release of chimeric VLPs containing RVFV glycoproteins (GP-SIV Gag VLPs). The chimeric VLP preparations were found to induce high levels of antibodies against RVFV glycoproteins that neutralize RVFV infectivity. These results demonstrate the potential of the chimeric VLPs formed by SIV Gag core protein with Rift Valley Fever virus glycoproteins for the development of an effective vaccine.

Example 3

VLPs with Chimeric RVFV GN and GC Proteins with the MuLV Cytoplasmic Tail

This example illustrates the enhanced release of RVFV glycoproteins by co-expression of MuLV Gag proteins with chimeric RVFV GN and GC proteins containing the MuLV Env cytoplasmic tail. The use of SIV Gag for the development of a human vaccine against RVFV may raise concerns for public acceptance due to the association of SUV with HIV. Therefore, the Gag protein of murine leukemia virus (MuLV), a murine type C retrovirus may be used for the RVFV VLP vaccine development. The gene of the MuLV Gag protein (Moloney strain) was cloned into the rBV transfer vector pC/pS1, and rBV-MuLV Gag was generated following established protocols. To enhance the levels of RVFV glycoprotein incorporation into MuLV Gag VLPs, genes for chimeric GN and GC proteins were constructed by replacing their cytoplasmic tail with the cytoplasmic tail of the MuLV Env protein, designated as GN-MuC and GC-MuC respectively (FIG. 19A), and rBVs expressing these chimeric proteins were generated.

Figure 19:
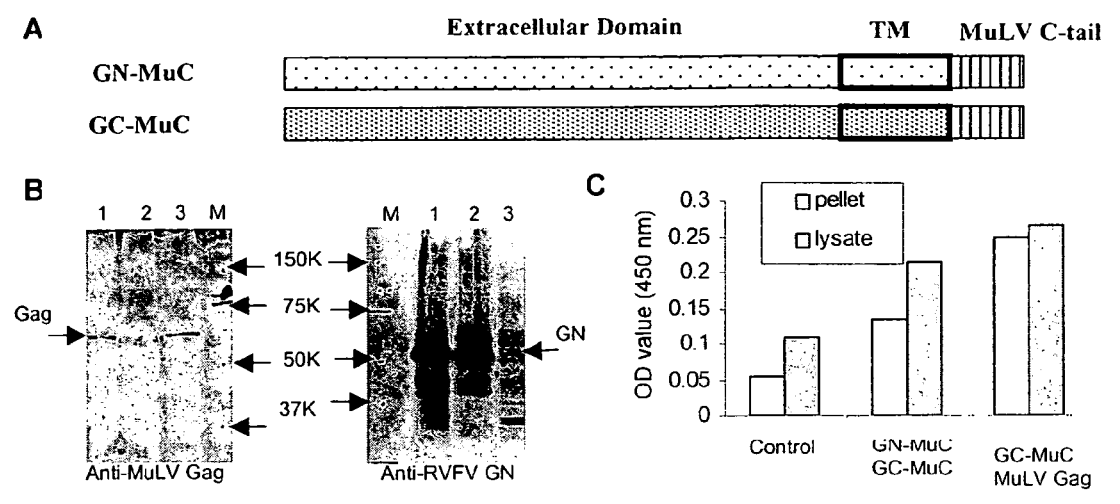

Expression and release of MuLV Gag and chimeric GN-MuC and GC-MuC proteins in Sf9 cells by recombinant baculoviruses were analyzed by Western blot and ELISA using antibodies against MuLV Gag or RVFV glycoproteins. Sf9 cells (10-7) were infected by rBV-GN-MuC and rBV-GC-MuC at the MOI of 5 with or without r BV-MuLV Gag at the MOI of 2 as indicated. Sf9 cells infected by rBV-MuLV Gag at the MOI of 2 were used as the control. At 60 hr post infection, the cell medium was collected, clarified of cell debris by centrifugation at 1200 rpm for 10 min, and the proteins in the medium were pelleted by centrifugation at 35000 rpm in a SW41 rotor then dissolved in 60 ul of lysis buffer. The Gn-MuC and GC-MuC chimeric proteins and the MuLV Gag protein released into the medium were detected by SDS-PAGE (10 ul per lane) followed by Western blot using antibodies against the MuLV Gag protein or monoclonal antibodies against the RVFV GN protein. As shown in FIG. 19B, the MuLV Gag protein (65 Kd in molecular weight) is released into the medium from Sf9 cells infected with rBV-MuLV Gag alone (lane 3) or together with rBV-GN-MuC and rBV-GC-MuC (lane 1). Similarly, the GN-MuC and GC-MuC chimeric proteins were also released into the medium when expressed with the MuLV Gag (lane 1) or without the MuLV Gag (lane 2).

The levels of chimeric GN-MuC and GC-MuC proteins in cell lysate and in the medium were compared by ELISA. The infected Sf9 cells were lysed by 100 ul of lysis buffer. The cell lysates and the lysed pellets were coated onto a Microtiter plate (10 ul per well) and the levels of RVFV glycoproteins in cell lysates and released protein pellets were compared by ELISA using mouse sera against RVFV as the primary antibody and HRP-conjugated Rabbit-anti-mouse lgG as the secondary antibody. As shown in FIG. 19C, similar levels of chimeric RVFV glycoproteins (GN-MuC and GC-MuC) were expressed in Sf9 cells infected with rBV-GN-MuC and rBV-GC-MuC or with rBV-GN-MuC and rBV-GC-MuC plus rBV-MuLV Gag. However, the levels of chimeric RVFV glycoproteins released into the medium increased by more than 60% when they are co-expressed with the MuLV gag protein. These results indicate that the chimeric proteins may interact with the MuLV Gag protein and are more efficiently incorporated into VLPs.

Therefore, having thus described the disclosure, at least the following is claimed:

1. A virus-like particle (VLP), comprising:
   a viral core protein that can self assemble into a VLP core, wherein the viral core protein is influenza M1 core protein;
   at least one viral surface envelope protein expressed on the surface of the VLP; and
   at least one adjuvant molecule expressed on the surface of the VLP, wherein at least one adjuvant is flagellin,
   wherein the VLP is nonreplicative and noninfectious, and wherein the VLP does not contain intact viral nucleic acids.

2. The VLP of claim 1, wherein the viral core protein and at least one viral surface envelope protein are from different viruses.

3. The VLP of claim 1, wherein the viral core protein and at least one viral surface envelope protein are from the same virus.

4. The VLP of claim 1, wherein the viral surface envelope protein is selected from: a retrovirus glycoprotein, a bunyavirus glycoprotein, a corona virus glycoprotein, an arenavirus glycoprotein, a filovirus glycoprotein, an influenza virus glycoprotein, a paramyxovirus glycoprotein, a rhabdovirus glycoprotein, an alphavirus glycoprotein, a flavivirus glycoprotein, a cytomeglavirus glycoprotein, and combinations thereof.

5. The VLP of claim 4, wherein the retrovirus glycoprotein is selected from: a human immunodeficiency virus (HIV) glycoprotein, a simian immunodeficiency virus (SIV) glycoprotein, a simian-human immunodeficiency virus (SHIV) glycoprotein, a feline immunodeficiency virus (FIV) glycoprotein, a feline leukemia virus glycoprotein, a bovine immunodeficiency virus glycoprotein, a bovine leukemia virus glycoprotein, an equine infectious anemia virus glycoprotein, a human T-cell leukemia virus glycoprotein, a mouse mammary tumor virus envelope glycoprotein (MMTV), and combinations thereof.

6. The VLP of claim 4, wherein the viral surface envelope surface protein is selected from: a Lassa Fever virus glycoprotein, an Ebola Virus glycoprotein, a VSV glycoprotein, a Hepatitis C Virus ~protein, a Herpes Virus glycoprotein, and combinations thereof.

7. An immunogenic composition, comprising the VLP of claim 1 and a pharmacologically acceptable carrier.

8. The VLP of claim 1, wherein at least one viral surface envelope protein is chimeric.

9. The VLP of claim 8, wherein the chimeric viral surface envelope protein comprises: at least a portion of the cytoplasmic domain of a viral surface envelope protein from a first virus, and at least a portion of one or more of a signal peptide domain, a transmembrane domain, or a C-tail domain of a peptide from a second virus.

10. An immunogenic composition, comprising the VLP of claim 8 and a pharmacologically acceptable carrier.

11. The VLP of claim 1, wherein the at least one adjuvant molecule is a glycosyl-phosphatidylinositol membrane-anchored form of an adjuvant molecule.

12. The VLP of claim 1, wherein the viral surface envelope protein is a glycoprotein.

13. A virus-like particle (VLP), comprising:
    a viral core protein that can self assemble into a VLP core, wherein the viral core protein is influenza M1 core protein;
    at least one viral surface envelope protein expressed on the surface of the VLP;
    at least one adjuvant molecule expressed on the surface of the VLP;
    wherein the VLP is nonreplicative and noninfectious; and
    wherein the adjuvant molecule is flagellin.

* * * * *